(12) United States Patent
Miller et al.

(10) Patent No.: US 11,857,337 B1
(45) Date of Patent: Jan. 2, 2024

(54) POWER MANAGEMENT FOR WEARABLE DEVICES

(71) Applicant: Tula Health, Inc., Kaysville, UT (US)

(72) Inventors: Devin W. Miller, Morgan, UT (US); David R. Miller, Morgan, UT (US)

(73) Assignee: Tula Health, Inc., Kaysville, UT (US)

( * ) Notice: Subject to any disclaimer, the term of this patent is extended or adjusted under 35 U.S.C. 154(b) by 0 days.

(21) Appl. No.: 18/062,606

(22) Filed: Dec. 7, 2022

Related U.S. Application Data

(63) Continuation of application No. 17/467,411, filed on Sep. 6, 2021, now abandoned, which is a continuation
(Continued)

(51) Int. Cl.
*H04B 7/00* (2006.01)
*A61B 5/00* (2006.01)
(Continued)

(52) U.S. Cl.
CPC .......... *A61B 5/4875* (2013.01); *A61B 5/0059* (2013.01); *A61B 5/0537* (2013.01); *A61B 5/1118* (2013.01); *A61B 5/1455* (2013.01); *A61B 5/14546* (2013.01); *A61B 5/6801* (2013.01); *A61B 5/681* (2013.01); *A61B 5/7221* (2013.01); *A61B 5/7278* (2013.01);
(Continued)

(58) Field of Classification Search
CPC .......... G06F 1/163; G06F 3/104; G06F 3/017; A61B 5/681; A61B 5/1118; H04W 52/0254; H04W 52/0261
See application file for complete search history.

(56) References Cited

U.S. PATENT DOCUMENTS

| 3,785,142 A | 1/1974 | Soguel |
| 5,372,136 A | 12/1994 | Steuer et al. |

(Continued)

OTHER PUBLICATIONS

Attas et al., Visualization of cutaneous hemoglobin oxygenation and skin hydration using near-infrared spectroscopic imaging, Skin Research and Technology 2001; 7; 238-245.
(Continued)

*Primary Examiner* — Tuan Pham
(74) *Attorney, Agent, or Firm* — Miller IP Law, LLC

(57) ABSTRACT

A method, system, apparatus, and/or device for adjusting a power consumption level of a device. The method, system, apparatus, and/or device may include: a first sensor interface, a second sensor interface, and a processing device coupled to the first sensor interface and the second sensor interface. The processing device may: measure a first physiological measurement via the first sensor interface within a first period of time; measure a second physiological measurement via the second sensor interface within the first period of time; adjust a power consumption level of the apparatus in view of at least one of the first physiological measurement or the second physiological measurement; measure the physiological measurement via the first sensor interface at the adjusted power consumption level within a second period of time; and measure a second physiological measurement via the second sensor interface at the adjusted power consumption level within the second period of time.

20 Claims, 20 Drawing Sheets

Related U.S. Application Data of application No. 17/023,235, filed on Sep. 16, 2020, now Pat. No. 11,109,805, which is a continuation of application No. 16/175,376, filed on Oct. 30, 2018, now Pat. No. 10,806,398, which is a continuation of application No. 14/957,330, filed on Dec. 2, 2015, now Pat. No. 10,154,460.

(60) Provisional application No. 62/192,932, filed on Jul. 15, 2015, provisional application No. 62/117,282, filed on Feb. 17, 2015.

(51) Int. Cl.
| | |
|---|---|
| *H04W 52/02* | (2009.01) |
| *A61B 5/0537* | (2021.01) |
| *A61B 5/145* | (2006.01) |
| *A61B 5/11* | (2006.01) |
| *A61B 5/1455* | (2006.01) |
| *A61B 5/0205* | (2006.01) |
| *A61B 5/318* | (2021.01) |
| *A61B 90/00* | (2016.01) |

(52) U.S. Cl.
CPC .......... *A61B 5/742* (2013.01); *H04W 52/0254* (2013.01); *H04W 52/0261* (2013.01); *A61B 5/0075* (2013.01); *A61B 5/02055* (2013.01); *A61B 5/318* (2021.01); *A61B 5/6803* (2013.01); *A61B 2090/064* (2016.02); *A61B 2560/0209* (2013.01); *A61B 2560/0252* (2013.01); *A61B 2560/0257* (2013.01); *A61B 2560/0456* (2013.01); *A61B 2560/0475* (2013.01); *A61B 2562/0219* (2013.01); *A61B 2562/0223* (2013.01); *A61B 2562/0261* (2013.01)

(56) References Cited

U.S. PATENT DOCUMENTS

| | | | |
|---|---|---|---|
| 6,442,408 B1 | 8/2002 | Wenzel et al. | |
| 6,687,519 B2 | 2/2004 | Steuer et al. | |
| 8,049,597 B1 | 11/2011 | Murakami et al. | |
| 8,174,482 B1 | 5/2012 | Yeung | |
| 8,406,865 B2 | 3/2013 | McKenna | |
| 8,517,912 B2 | 8/2013 | Clare | |
| 8,594,779 B2 | 11/2013 | Denison et al. | |
| 8,795,174 B2 | 8/2014 | Manicka et al. | |
| 9,402,545 B2 * | 8/2016 | Baker | A61B 5/0002 |
| 9,495,126 B2 | 11/2016 | Lang | |
| 2002/0007126 A1 | 1/2002 | Nissila | |
| 2003/0216663 A1 | 11/2003 | Jersey-Willuhn et al. | |
| 2003/0229455 A1 | 12/2003 | Bevilacqua et al. | |
| 2004/0015058 A1 | 1/2004 | Besson et al. | |
| 2005/0209512 A1 | 9/2005 | Heruth et al. | |
| 2008/0033315 A1 | 2/2008 | Kim et al. | |
| 2008/0039700 A1 | 2/2008 | Drinan et al. | |
| 2008/0146891 A1 | 6/2008 | Nang et al. | |
| 2008/0309481 A1 * | 12/2008 | Tanaka | A61B 5/0002 340/286.01 |
| 2009/0105560 A1 | 4/2009 | Solomon | |
| 2011/0092779 A1 | 4/2011 | Chang et al. | |
| 2011/0245633 A1 | 10/2011 | Goldberg et al. | |
| 2011/0245711 A1 | 10/2011 | Katra et al. | |
| 2012/0245439 A1 | 9/2012 | Andre et al. | |
| 2012/0271121 A1 | 10/2012 | Della Torre et al. | |
| 2013/0013327 A1 | 1/2013 | Horseman | |
| 2013/0119255 A1 | 5/2013 | Dickinson et al. | |
| 2013/0198694 A1 | 8/2013 | Rahman et al. | |
| 2013/0245487 A1 | 9/2013 | Aga | |
| 2014/0074824 A1 | 3/2014 | Rad et al. | |
| 2014/0114151 A1 | 4/2014 | Miller | |
| 2014/0127650 A1 | 5/2014 | Utter, II | |
| 2014/0207914 A1 | 7/2014 | Robinson | |
| 2014/0213863 A1 | 7/2014 | Loseu et al. | |
| 2014/0221792 A1 | 8/2014 | Miller et al. | |
| 2014/0275852 A1 | 9/2014 | Hong et al. | |
| 2014/0276192 A1 | 9/2014 | Stivoric et al. | |
| 2014/0278229 A1 | 9/2014 | Hong et al. | |
| 2014/0309789 A1 | 10/2014 | Ricci | |
| 2014/0309868 A1 | 10/2014 | Ricci | |
| 2014/0316297 A1 | 10/2014 | Mccaughan et al. | |
| 2014/0316305 A1 | 10/2014 | Venkatraman et al. | |
| 2014/0336493 A1 | 11/2014 | Kulach et al. | |
| 2014/0342836 A1 | 11/2014 | Pearce | |
| 2014/0361147 A1 | 12/2014 | Fei | |
| 2014/0372250 A1 | 12/2014 | Dugan | |
| 2015/0101053 A1 | 4/2015 | Sipple | |
| 2015/0164370 A1 | 6/2015 | Wabel et al. | |
| 2015/0220109 A1 * | 8/2015 | von Badinski | H02S 40/22 368/10 |
| 2015/0238140 A1 | 8/2015 | Labelle et al. | |
| 2015/0324564 A1 | 11/2015 | Sahu et al. | |
| 2016/0019813 A1 | 1/2016 | Mullen | |
| 2016/0192716 A1 | 7/2016 | Lee | |

OTHER PUBLICATIONS

Donoghue et al., "Heat exhaustion in a Deep Underground Metalliferous Mine", Occupational and Environmental Medicine, Mar. 2000; 57(3); 165-174.

Maattala et al., "Optimum Place for Measuring Pulse Oximeter Signal in Wireless Sensor-Belt or Wrist-Band", IEEE CCIT, 2007, pp. 1856-1861.

NIST, Summary of Basic Atomic Spectroscipic Data for Na and K, cross reference dated 1922, 1956, 1971.

* cited by examiner

610

Wireless Transfer Coil
620

Power Management Module
630

Batteries
640

FIG. 6

POWER MANAGEMENT FOR WEARABLE DEVICES

CROSS-REFERENCE TO RELATED APPLICATION

This application is a continuation of U.S. patent application Ser. No. 17/467,411, filed Sep. 6, 2021, which is a continuation of U.S. patent application Ser. No. 17/023,235, filed Sep. 16, 2020, which is a continuation of U.S. patent application Ser. No. 16/175,376, filed Oct. 30, 2018, and which is a continuation of U.S. patent application Ser. No. 14/957,330, filed Dec. 2, 2015. The '330 application claims priority to U.S. Provisional Application No. 62/117,282, filed Feb. 17, 2015, and claims priority to U.S. Provisional Application No. 62/192,932, filed Jul. 15, 2015. The entire contents of these aforementioned applications are incorporated herein by reference.

BACKGROUND

As portable devices and technology continue to expand and develop, individuals are increasingly searching for devices to measure and monitor various aspects of their lives. For example, wearable fitness monitors can enable users to measure how many steps an individual has taken over a period of time or an amount of time the individual is active over a period of time. Smart watches can enable users to execute applications, receive and send text messages, make phone calls, and so forth. Portable medical devices can enable a user to take medical measurements outside of a hospital environment. For example, a diabetic can use a portable insulin measurement device to monitor their blood sugar level.

Portable or mobile electronic devices use power to perform different functions. For example, wristwatches can be used to tell time, mobile phones can be used for communication, and tablet computers can be used for gaming. Portable or mobile electronic devices use a variety of different power sources, such as batteries, solar power, mechanical power, and so forth to provide power circuitry of the device to perform the different functions. Typically, portable or mobile devices may use batteries for increased power density and capacity. While power density and capacity of batteries continue to increase and batteries continue to be miniaturized, batteries deliver a limited amount of power before the batteries need to be replaced or recharged.

The portable or mobile electronic devices are limited in functionality and/or period of use in view of the type of energy storage device (such as a battery) and the capacity the energy storage device. For example, a mobile phone has a maximum period of time a user can use it to talk continuously before the battery of the mobile phone is exhausted. With a limit on an amount of energy a power source can deliver to a portable or mobile electronic device, power management can be used to extend a usable period of time of the portable or mobile electronic devices.

BRIEF DESCRIPTION OF THE DRAWINGS

Features and advantages of the disclosure will be apparent from the detailed description which follows, taken in conjunction with the accompanying drawings, which together illustrate, by way of example, features of the disclosure; and, wherein:

FIG. 6 illustrates a UMD or a base station according to one embodiment.

Figure 1A:
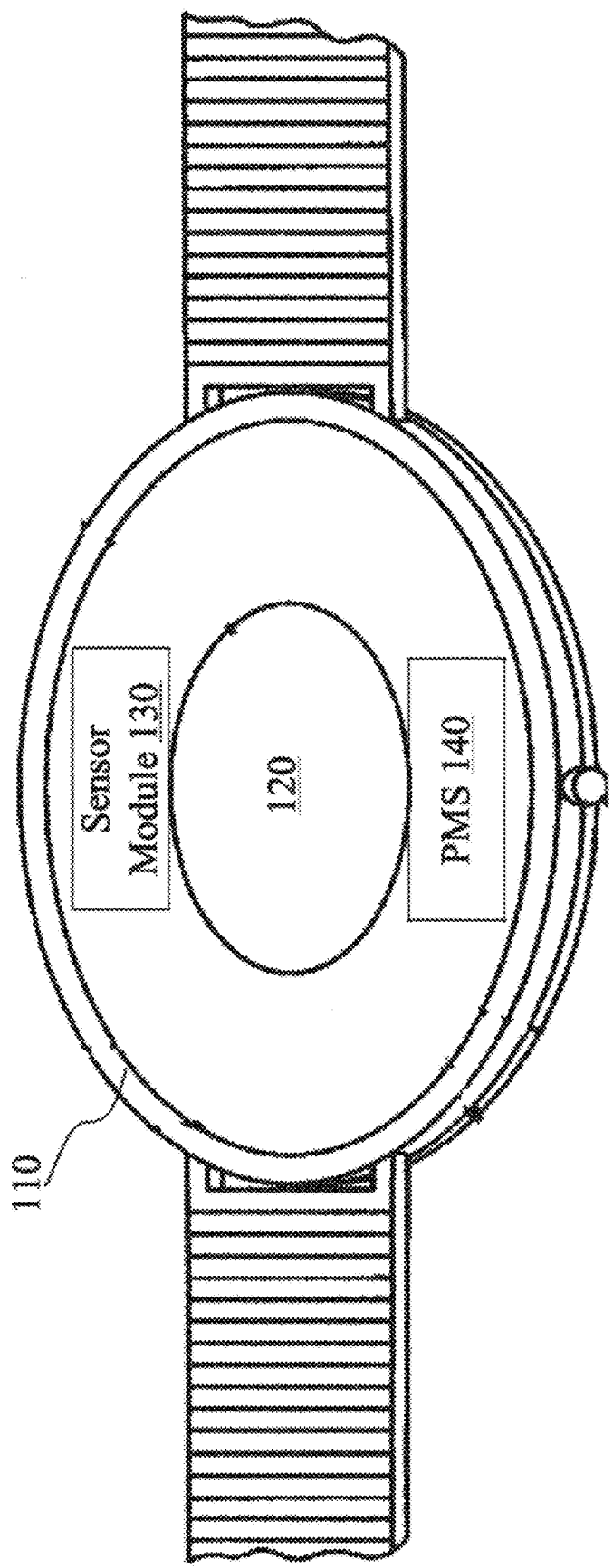
FIG. 1A illustrates a bottom view of the user measurement device (UMD), such as a wearable wristband, that can be used to take measurements using one or more sensors according to one embodiment.

Reference will now be made to the exemplary embodiments illustrated, and specific language will be used herein to describe the same. It will nevertheless be understood that no limitation of the scope of the invention is thereby intended.

DETAILED DESCRIPTION

As data becomes increasingly easier to access, individuals can increasingly desire to monitor, collect, and/or analyze various aspects of their environment and/or physiology. For example, a sport or fitness enthusiast may desire to monitor, collect, and/or analyze various aspects of the fitness routine (such as their heart rate, workout intensity, workout duration, and so forth) to determine how to improve and adjust their fitness routine to increase its efficacy. In another example, an asthmatic may desire to monitor, collect, and/or analyze environmental condition information (such as air quality, pollen count, and so forth) to determine and avoid conditions that may aggravate their condition.

Described herein are apparatuses and methods for power adjustments of user measurement device. In one apparatus, a processing element is coupled to a first sensor interface and a second sensor interface. The processing element measures a physiological measurement via the first sensor interface and measures an amount of activity of the apparatus via the second sensor interface. A physiological measurement may be any measurement related to a living body, such as a human's body or an animal's body. The physiological measurement is a measurement made to assess body functions. Physiological measurements may be very simple, such as the measurement of body or ambient temperature, or they may be more complicated, for example measuring how well the heart is functioning by taking an ECG (electrocardiograph). Physiological measurements may also include motion and/or movement of the body, including measures of speed, acceleration, position, absolute or relative location, or the like. In some cases, these physiological measurements may be taken to determine an activity level for power management, as described herein. The physiological measurements can be medical measurements, such as heart rate measurement data, hydration level measurement data, blood pressure measurement data, oxygenation level, and so forth; a representation of a set of environmental measurements for the individual, such as an ambient temperature of a location approximate the individual and a location of the individual; a representation of a trending of physiological and/or environmental information, such as increases or decreases in the physiological and/or environmental information; a representation of a performance of an individual; or a representation of the individual compared to the group overall. The processing element performs a power adjustment activity in view of the amount of activity. For example, the power adjustment activity may be to perform any one or more of the following: adjust a number of different physiological measurements to take; adjusting a frequency of taking physiological measurements; turning off one or more systems; adjusting a type, frequency, data rate, number of channels and/or power at which to communicate data. In another embodiment, the power management system described herein may adjust one or more sensors in view of a rate of change in the measurements of the one or more sensors.

Power management of portable or mobile electronic devices can be used to extend the useful engagement of the devices by reducing the duty cycle of the "on" time period for the device.

Rechargeable batteries often employ chemistries such as nickel cadmium (NiCd), nickel metal hydride (NiMH) and various forms of lithium-configurations. Conventionally, the rechargeable batteries are recharged by supplying electrical energy (e.g., current) through wires that are connected via the electronic device to the battery, such as through a battery management system (BMS). The electronic device may have external electrical contacts for receiving electrical energy from an external power supply to recharge the batteries. The external electrical contacts, however, may be prone to poor performance, or even failure, due to becoming dirty or corroded. Further, electrical contacts are undesirable for use with electronic devices where a possibility of electrical shorting may occur, such as when the device may be exposed to water. The exposed electrical contacts make the electronic device difficult to waterproof.

Alternatively, contact-less charging using induction has been used in electronic devices, such as motorized toothbrushes and cordless phones. An inductively-rechargeable electronic device may be placed on an inductive charger. The inductive charger includes a primary coil and the electronic device includes a secondary coil. Alternating current flows through the primary coil of the inductive charger, causing a varying magnetic field that is intersected by the secondary coil in the electronic device to receive energy. The energy received by the secondary coil can be used to charge the battery in the electronic device.

Although inductive charging obviates the need for contacts, inductive charging may not be practical for use with smaller electronic devices because the smaller devices do not have the volumetric space to accommodate a coil large enough to efficiently transfer energy to charge a battery. A smaller electronic device may be a device that is suitable to be worn by, or carried by, a person, such as a wearable device. Wearable devices may be attached directly to the person or may be attached to an article that can be attached, worn, or otherwise disposed on a person or equipment being used by a person. Further, the coil may interfere with the ability of the electronic device to communicate using radio frequency.

Power management of portable or mobile electronic devices can be used to extend the use period of the devices. While portable or mobile electronic devices' operational time may be limited by a volumetric or power density size of a battery coupled to the portable or mobile electronic devices, power management can be used to extend a period of time a user can use the portable electronic device or the amount of time the portable electronic device is powered on and available for use.

FIG. 1A illustrates a bottom view of the UMD 110. In one example the UMD 110 can be a wearable UMD, such as a wearable wristband, that can be used to take selected measurements using one or more sensors 120 according to one embodiment. In one embodiment, the one or more sensors 120 can be a bio-impedance sensor, an accelerometer, a three dimensional (3D) accelerometer, a gyroscope, a light sensor, an optical sensor, a spectroscopy sensor, a heart rate monitor, a blood pressure sensor, a pulse oximeter sensor, and so forth. In one example, the UMD 110 can include a sensor module 130 to receive measurement information from the one or more sensors 120 and analyze the measurement information to determine selected physiological information and/or medical information, such as a hydration level of the user, cardiac information of the user (e.g., blood pressure or heart rate), an blood oxygen level of the user, and so forth. In another example, the UMD 110 can include a power management system 140 to perform power management for the UMD 110. The power management system 140 may be hardware (circuitry, dedicated logic, etc.), software (such as is run on a general purpose computing system or a dedicated machine), firmware (embedded software), or any combination thereof. The power management system 140 is described in more detail below, including a power management module described below with respect to FIG. 11.

Figure 1B:
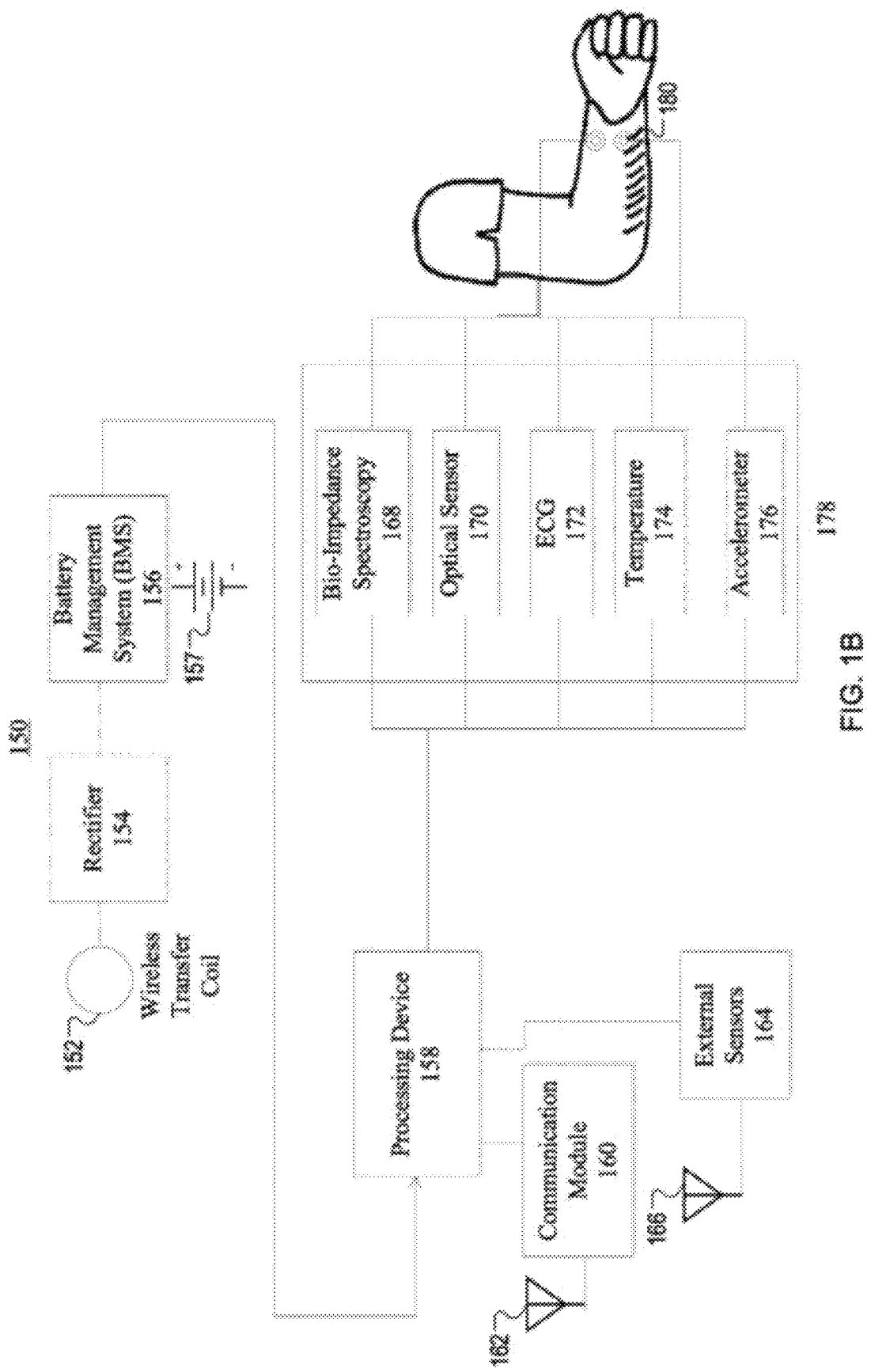
FIG. 1B illustrates a schematic view of the UMD according to one embodiment. The FIG. 2A shows a base station configured as a hook according to one embodiment.

FIG. 1B illustrates a schematic view of the UMD 150 according to one embodiment. The UMD 150 can include a wireless transfer coil 152 to receive wireless power from another wireless transfer coil of another device, such as a wireless charger. A rectifier or impedance matching device 154 can convert the wireless power into direct current (DC) power and transfer the DC power to a battery management system (BMS) 156. In one example, the BMS 156 can direct the DC power to a power storage device 157, such as a rechargeable battery, to replenish power to the power storage device 157 (e.g., recharge the rechargeable battery). In another example, the BMS 156 can direct the DC power to a processing device 158. In another example, the BMS 156 can direct power from the power storage device 157 to the processing device 158. The processing device 158 can include a processor, a memory storage device, an analog-to-digital converter, and/or a digital-to-analog converter. In one example, the processing device 158 can be coupled to a communication module 160 to communicate data with other devices using an antenna 162. The antenna 162 can be configured to communicate on a wireless network and/or a cellular network. In another example, the processing device 15 8 can be coupled to one or more external sensors. The external sensors 164 can be sensors that take measurements external to the user, such as non-physiological measurements or non-direct engagement measurements of the user. The external sensors 164 can include a global positioning system (GPS) device, a triangulation device, a humidity sensor, an altimeter, and so forth. In another example, the processing device 158 can be coupled to a sensor array 178. The sensor array 178 can include one or more sensors to engage a user of the UMD to take measurements. The sensor array 178 can include: a bio-impedance spectroscopy sensor 168, an optical sensor 170, an electrocardiogram (ECG) sensor 172, a temperature sensor 174 (such as a thermostat or thermistor), an accelerometer 176, and so forth.

The user monitoring system can also include an analysis tool that can analyze input data. In one example, the analysis tool can be integrated into the UMD or coupled to the UMD. In another example, the analysis tool can be integrated or coupled to a cloud-based computing system that can communicate with the UMD.

In one example, the analysis tool can receive input data for a memory of the UMD and/or the cloud-based computing system. In another example, the analysis tool can receive the input data can in real-time from the UMD and/or the cloud-based computing system.

The input data can include measurement data and/or user information. The measurement data can include information collected using one or more sensors in a sensor array of the UMD, environmental sensors, Newtonian sensors, third-party sensors or devices, and so forth (as discussed in the preceding and proceeding paragraphs). The input data can include profile information, such as: user profile information; group profile information; and so forth.

The analysis tool can determine a correlation between different data points or data sets of the input data (such as data collected from different sensors or devices). The analysis tool can determine different types of correlations of the data points or data sets. In one example, the analysis tool can use a Pearson product moment correlation coefficient algorithm to measures the extent to which two variables of input data may be related. In another example, the analysis tool can determine relations between variables of input data based on a similarity of rankings of different data points. In another example, the analysis tool can use a multiple regression algorithm to determine a correlation between a data set or a data point that may be defined as a dependent variable and one or more other data sets or other data points defined as independent variables. In another example, the analysis tool can determine a correlation between different categories or types of information in the input data.

In one example, when the analysis tool determines a correlation between the different data points or data sets, the analysis tool can use the correlation information to predict when a first event or condition may occur based on a second event or condition occurring. In another example, when the analysis tool determines a correlation between the different data points or data sets, the analysis tool can use the correlation information to determine a diagnosis or result data. In another example, when the analysis tool determines a correlation between the different data points or data sets, the analysis tool can use the correlation information to determine a cause of a condition and/or event.

In one example, the analysis tool can determine a correlation between physiological data and environmental data. For example, the input data can include hydration level data (physiological data) and ambient temperature data (environmental data). In this example, the analysis tool may identify a correlation between when the ambient temperature increases and a decrease in a hydration level of a user. The analysis tool may identify the correlation between the ambient temperature and the hydration level by using a regression algorithm with the ambient temperature as an independent variable and the hydration level as a dependent variable. When the analysis tool has identified the correlation between the ambient temperature and the hydration level, the analysis tool can predict a change in a hydration level of a user or a rate of change of a hydration level of a user based on the ambient temperature.

In another example, the analysis tool can determine a correlation between an altitude level and an oxygenation level of a user. For example, the analysis tool can determine a correlation between an increase in the altitude level and a decrease in the oxygenation level of the user. When the analysis tool determines the correlation between the altitude level and the oxygenation level, the analysis tool can predict a change in the oxygenation level of the user based on the altitude level the user may be at. The preceding examples are intended for purposes of illustration and are not intended to be limiting. The analysis tool can identify a correlation between various data points, data sets, and/or data types.

In one example, the analysis tool can identify a correlate between location information and physiological data of a user. For example, the analysis tool can determine a location of a user for at a period of time, such as by using GPS sensor data or triangulation sensor data. In this example, the analysis tool can receive physiological measurement data (such as heart rate measurement data, hydration level measurement data, blood pressure measurement data, and so forth). The analysis tool can correlate the location of the user with the physiological measurement data to increase an accuracy of data analysis, a diagnosis, or result data and/or provide additional details regarding a cause of physiological measurements.

In one example, the analysis tool can determine that a user is at work in an office location. When the analysis tool detects an increase in a heart rate or a blood pressure of a user, the analysis tool can correlate heart rate or blood pressure data with the location information to determine a cause of the increase in heart rate or blood pressure. For example, when a heart rate or blood pressure of an individual increases while at a work in an office, the analysis tool may determine that the heart rate or blood pressure increase may be due to psychological causes (such as stress) rather than physiological causes (such as exercising or working out) because the user is at a location where an individual is not likely to physically exert himself or herself.

In one example, the analysis tool can use the multiple regression algorithm to determine a correlation between a multiple physiological and/or environmental data points or data sets. For example, the analysis tool may receive heart rate data, skin temperature data, and hydration level data of a user. In this example, the analysis tool can determine a correlation between both a heart rate and skin temperature of an individual and a hydration level of the individual. For example, the analysis tool may determine that as the heart rate and the skin temperature of an individual increase, the hydration level of the individual may decrease.

In one example, the analysis tool can filter out a correlation determination (e.g., a determination that data points or data sets may be correlated) when the correlation level is below a threshold level. For example, when the analysis tool determines that there may be a 30 percent correlation between a skin temperature of an individual and a hydration level of an individual, the analysis tool may filter out the correlation information when determining a cause of a condition or event, a result of the data, or a diagnosis.

In another example, the analysis tool can discount or weight a correlation determination based on the correlation level of the correlation determination. For example, when the analysis tool determines that there may only be a 30 percent correlation between a skin temperature of an individual and a hydration level of an individual, the analysis tool may discount or assign a lower weight to the correlation determination (relative to a higher correlation percentage such as 90 percent) when determining a cause of a condition or event, a result of the data, or a diagnosis.

In one example, the analysis tool can assign weights to different factors, such as: physiological data, environmental data, time of day, and so forth. In one example, the analysis tool can assign a first weight to hydration level data of an individual and a second weight to heart rate data of an individual when determining a performance level of an individual, as discussed in the proceeding paragraphs. In this example, when determining a performance level, the analysis tool may assign a higher weight to the hydration level data relative to the heart rate data.

In one example, the analysis tool can use predetermined weights for the different physiological and/or environmental data. In another example, the analysis tool can receive user-defined or predefined weights from an input device indicating the weights for the different physiological and/or environmental data. In another example, the analysis tool can determine the weights to assign to the different physiological and/or environmental data based on correlation levels of the different physiological and/or environmental data. For example, when a correlation level between a humidity level and a heart rate of an individual may be relatively low over a threshold period of time and/or under a threshold number of different conditions, the analysis tool may assign a low weight to humidity level data when determining a cause of a change in heart rate of a user.

In one example, the analysis tool can assign different weights to physiological measurements based on environmental data. For example, based on a location of an individual, the analysis tool can assign a first weight to a heart rate measurement and a second weight to a respiration sensor measurement.

In another example, the analysis tool can assign weights to different causes, diagnosis, or results, such as: an exertion level (e.g., working out or sleeping), a stress level, an amount of time a user sleeps each day, and so forth.

In another example, the analysis tool can use environmental data to determine a cause of a physiological diagnosis. For example, when the user is located at a fitness facility, the analysis tool can increase a weight for physical exertion (e.g., working out) diagnosis as a cause of physiological measurements (such as an increase in a heart rate or decrease in a hydration level of a user). In another example, when a user is located at home in bed, the analysis tool can correlate a location of the user with physiological measurements of the user. In this example, the analysis tool can determine that a decrease in heart rate may be due to an individual going to sleep when a user is located in their bedroom for a threshold period of time.

The analysis tool can track, sort and/or filter input data. The input data can include: user schedule information, such as a daily schedule of the user; survey information, such as information received from surveys of individuals; research information, such as clinical research information or academic research information associated with one or more measurements of the UMD; and so forth.

The analysis tool can use scheduling information of the user in determining an expected or probable activity of a user. For example, when a user is a member of a sports team, the user's schedule may include practice schedule information and/or game schedule information. In this example, the analysis tool can use the schedule information to anticipate that the user may be participating in physical activity and provide recommendations to the user based on the physical activity. For example, the analysis tool can determine that the user may be practicing in 2 hours, can determine a current hydration level of the user, and can communicate a recommendation (such as via a sensory indicator of the UMD) to increase the hydration level of the user. A sensory indicator can include: a visual indication device, such as a display; an auditory indication device, such as a speaker; and/or touch indication device, such as a vibrator.

In another example, the analysis tool can use the scheduling information in correlation with a location of the user to determine an expected or probable activity. For example, the scheduling information may indicate that the user may be scheduled to attend a lecture at a physical fitness facility and the analysis tool can adjust a location-based recommendation in view of the scheduling information. In this example, while typically the analysis tool may recommend increasing a hydration level of the user in anticipation of physical activity based on the location information (e.g., the physical fitness facility), the analysis tool can adjust the recommendation in view of the scheduling information that the user may be attending a lecture rather than working out.

The analysis tool can store historical or previous input data of the user (as discussed in the proceeding and preceding paragraphs). In one example, the analysis tool can be integrated into the UMD and can store the historical information on a memory device of the UMD. In another example, the analysis tool can be integrated into the UMD and can use a communication module of the UMD to store the information on a memory device coupled to the UMD, such as a cloud-based storage device or a memory device of another computing device. In another example, the analysis tool can be part of a cloud-based system or the other computing device.

The analysis tool may filter and/or sort input data. In one example, the analysis tool can receive a filter or sort command from the UMD or an input device to filter and/or sort the input data. In another example, the filter or sort command can include filter parameters and/or sort parameters. The filter parameters and/or sort parameters can include: a time of day, a day of the week, group information, individual information, a measurement type, measurement duration, an activity type, profile information, injury information, performance level information, and so forth.

In another example, the analysis tool can sort and/or filter the input data based on a trending of input data. For example, the analysis tool can sort input data that may be trending in an increasing direction or a decreasing direction and can sort the input data based on the trending. In this example, different measurements for an individual may be trending in different directions, such as a hydration level of an individual may be trending towards a dehydrated level and an activity level of an individual may be stable or stagnant. The analysis tool can sort input data to display hydration level trending because the individual may be trending towards dehydration while filtering out the activity level information.

In one example, the analysis tool can sort or filter the input data on a group level. In another example, the analysis tool can sort or filter the input data on an individual level.

The analysis tool may receive survey information and/or research information from an input device. For example, the analysis tool may receive survey information that includes: gender information, age information, physical weight information, general health information, family information, fitness level information, and so forth. In one example, the analysis tool can determine a correlation between the survey information and the input data. For example, the analysis tool can correlate the age, weight, fitness level, and general health level of a user with survey information from other individuals to determine a correlation between the survey information for the individual and the other individuals. In this example, the analysis tool can set a baseline for a measurement of the UMD for the individual based on baselines for the other individuals with the same or similar survey information. In another example, the analysis tool can correlate the user information with research information (such as research papers, clinical studies, and so forth).

In one example, the analysis tool can communicate information to a display of the UMD. The information can include diagnosis information, recommended actions, trending information, raw data, and so forth. In another example, the analysis tool can communicate the information to another computing device or cloud-based server to display the information using a graphical user interface (GUI).

In one example, the UMD, the other computing device, the cloud-based server, and/or the analysis tool can aggregate data received from one or more UMD users. For example, members of a sports team can each use a UMD to collect information. Analysis tools of the UMDs can analyze and communicate information for each of the members of the sports team to the cloud-based server.

The GUI can provide a user with different representations of the data or information for display. In one example, the GUI can receive representation information indicating information to display via the GUI.

In one example, the representation information can include a group indicator, an individual indicator, and/or a detailed indicator. The group indicator can indicate to display the representation information in a group format, such as a team format for a sports team. The individual indicator can indicate to display the representation information in an individual format for one or more individuals, such as displaying individual team member information for a sports team. The detailed indicator can indicate to display the representation information in a detailed format for an individual, such as displaying greater detail in representation information for an individual team member.

In one example, the GUI can layer or overlay different levels of representation information in view of the group indicators, the individual indicators, and the detailed indicators. For example, the GUI can initially display the representation information in a group format (e.g., a first layer of information) such as displaying physiological information for a team (e.g., a group). When the GUI receives an individual indicator requesting to display information for an individual of the team, the GUI can display the individual's information in a layer above the group layer (e.g., a second layer of information). In one example, the second layer of information can be displayed in a box or field that is overlaid on top of at least part of the first layer of information. In one example, the second layer of information can be partially transparent or semi-transparent, e.g., a viewer can still see at least part of the first layer information beneath the second layer of information.

In another example, the GUI can receive the group indicators, the individual indicators, and the detailed indicators from an input device, such as a touch screen, a mouse, a stylus, a keyboard, and so forth. In one example, the input device can send the group indicators, the individual indicators, and/or the detailed indicators when a user clicks or selects on a selected area of the screen, such as selecting an individual of the team in the group layer. In another example, the input device can send the group indicators, the individual indicators, and/or the detailed indicators when a user hovers a pointer or selector (such as a cursor, an arrow, or a hand icon) over an individual of the group in the group layer. In this example, when the pointer hovers over the individual, the GUI can display the information of the individual in a second layer, and when the pointer is moved (e.g., no longer hovers over the individual) the second layer may no longer be displayed. An advantage of displaying the second layer (or other layers such as a third layer of detailed information) can be to enable the user to quickly and efficiently move between viewing different layers of information for one or more individuals or groups.

The group layer of information can be displayed when the group indicator may be selected and the GUI can display representation of group information including: a representation of different types of individual in a group or different locations of individual in the group, such as a locations or positions of different members on a team; a representation of information (such as input data) for the group as a whole; a representation of an aggregated health level of the group, such as an overall health score of the team; a representation of trending information for the group, such as trending information of the different measurements by the UMDs of the group; a representation of a threshold increase or decrease in measurement data, such as when an aggregation of measurements by the UMDs of the group exceeds or decreases below-defined threshold levels; a representation of a group performance indicator; a representation of multiple groups, such as a representation of a same type of measurement data for different teams of a sports association; a representation of one or more individual in the group versus one or more other individuals in the group, such as different team member of a group or team member that play the same position on the team.

The input data can include user profile data received at the UMD from an input device. The user profile data can include: dietary information of the user, ethnic or race information of the user, weight information of the user, gender information of the user, and so forth.

In one example, the analysis tool can determine a correlation between a hydration level of a user and physical performance of a user. In this example, the analysis tool can set the physical performance as a dependent variable and the hydration level of the user as an independent variable. The analysis tool can use the correlation between the hydration level and the physical performance to determine a physical performance of the user based on different hydration levels of the user.

In one example, the analysis tool can aggregate input data from different users and determine correlations between input data of the different users. In another example, the analysis tool can determine a correlation between current or real-time input data of a user and previous input data of a user.

The analysis tool can determine a baseline measurement for a user for one or more physiological measurements taken using the sensor array. In one example, the analysis tool can determine a baseline measurement for an individual by iteratively determining medium of a measurement, such as a heart rate measurement, over a period of time. For example, the UMD may measure a hydration level of a user using a bio-impedance sensor that measures bio-impedance in ohm (Q). A peak hydration level (e.g., over-hydrated) of the user may be at 5 Q and a minimum hydration level may be at 1 Q (e.g., dehydrated). In this example, the average hydration level of the user may be determined by taking a medium or average of the individual over a period of time. For example, while the user may have a peak hydration level at 5 Q and a minimum hydration level at 1 Q, the user may on average hydration level at 3.7 Q. As the user continues to use the UMD over a period of time, the analysis tool can monitor the hydration level of the individual to determine the average hydration level of the individual over the period of time. In this example, the average hydration level of the user may be at 3.7 Q even though the bio-impedance hydration level range spans from 1 Q to 5 n.

In one example, the analysis tool can determine a baseline range measurement of a user by determining a reoccurring or repetitive range of measurements of the user over a period of time. In this example, the bio-impedance Q measurement range of an individual may be between 1 Q and 5 Q. Over a period of time, the bio-impedance Q measurements may range between 1.7 Q and 2.2 Q. The analysis tool can determine that the baseline range for the user that indicates that the user may be hydrated can be measurements that are within the range of 1.7 Q and 2.2 Q.

In another example, the analysis tool can correlate different measurement ranges for different measurements and/or different diagnoses. For example, the analysis tool can determine that a first range can be when a user may be hydrated, a second range when a user may be dehydrated, and a third range when a user may be over-hydrated. In this example, the first range can be an average or medium range of measurement points over time, the second range can be a minimum range of measurement points over time, and the third range can be a maximum range of measurement points over time.

In another example, different ranges can be associated with different diagnoses. For example, a first range for bio-impedance may be associated with a hydration level of a user and a second range of bio-impedance may be associated with a glucose level. In another example, the first range for bio-impedance may be associated with a hydration level of the user and a second range of optical spectroscopy may be associated with a glucose level of the user.

The analysis tool can use different analysis algorithms when analyzing measurement data based on different activities of a user. In one example, the different activities can be different sports activities a user may be participating in. For example, the analysis tool can use a first analysis algorithm when a user is playing basketball and a second analysis algorithm when the user is playing football. In another example, the different activities can be different types of actions. The different types of actions can include: sleeping, sitting, walking, jogging, running, climbing, laying, standing, stepping, and so forth.

In one example, the UMD can use one or more of the sensors of the sensor array to determine the different activities. In another example, the UMD can receive user input, such as from a touch screen or an input device (e.g., a smartphone, tablet, computer, stylus, and so forth). In another example, the different activities can be associated with different criteria, such as a time of day, location, and so forth.

The analysis tool can use multiple measurements from different sensors to determine different diagnoses. The different measurements can include: hydration, skin temperature (Temp), heart rate (FIR), blood pressure (BP), oxygen saturation level (02), steps or mileage, sleep tracking, recovery tracking, and so forth.

The analysis tool can determine a performance metric of a user based on one or more measurements and/or one or more diagnosis of a user. In one example, the analysis tool can determine a diagnosis in one or more of multiple categories, including: hydration, skin temperature, heart rate, blood pressure, oxygen saturation, activity level, sleep activity, recovery activity, and so forth.

In one example, the diagnosis can have predetermined ranges for a user. In one example, the predetermined ranges can be defined by the user. In another example, the pre-defined ranges can be determined based on a user profile. For example, a hydration level can have multiple ranges such as a dehydrated range, a hydrated range, and an overhydrated range. The heart rate can have multiple ranges such as a slow range, a normal range, and a fast range. The oxygen saturated level can have multiple ranges such as a low range, a medium range, and a high range. In this example, the analysis tool can determine a fitness level of a user when a threshold number of ranges of the different diagnosis may be within the predetermined categories. For example, when a hydration diagnosis may be at a hydrated range, a heart rate diagnosis may be at a normal range, and an oxygen saturation diagnosis may be at a medium range, a user of the UMD may be at peak performance (such as a 100% performance level). In this example, when a hydration diagnosis may be at a dehydrated range, a heart rate diagnosis may be at a low range, and an oxygen saturation diagnosis may be at a low range, a user of the UMD by be at poor performance (such as a 65% performance level).

In one example, the analysis tool can determine a recovery rate of a user for an activity or event (e.g., an amount of time it may take the user to recover from an activity or event) based on measurements from the sensors in the sensor array.

In one example, the analysis tool can determine a recovery rate of a user based on a heart rate of the user. In this example, the analysis tool can identify a target or baseline heart rate of a user for an activity or event. The target or baseline heart rate can be a stable or steady heart rate of the individual after a period of time while the event or activity may be occurring. The analysis tool can monitor the heart rate of the user during the event and determine when the event or activity has finished. Upon completion of the activity, the analysis tool can take a first heart rate measurement. After a threshold period of time has passed, the analysis tool can take a second heart rate measurement. The analysis tool can then determine a difference between the first heart rate measurement and the second heart rate measurement. The analysis tool can then determine a rate at which the heart rate of the individual is slowing down or increasing to determine a recovery rate of the individual. For example, when the activity may be that the user is running, the analysis tool can take the first measurement when the user finishes their run and a second measurement 3 minutes after the first measurement. The analysis tool can determine a rate that the heart rate of the user is decreasing after the run to determine a recovery rate of the user. In this example, the greater the rate that the heart rate decreases the greater the recovery rate of the user. In another example, the analysis tool can take multiple different measurements at different times after the activity to increase an accuracy level of the recovery rate determination.

In another example, the analysis tool can use multiple sensors to take different measurements when determining the recovery rate.

In one example, the analysis tool can determine a sleep rate of a user based on one or more measurements of the user. For example, the analysis tool can receive a heart rate measurement, an activity level measurement, a body temperature, a blood pressure, and/or a blood oxygenation measurement. In this example, the analysis tool can determine that a user may be going to sleep based on a decrease in activity level and/or a decrease in heart rate. When the analysis tool has determined the user may be going to sleep, the analysis tool can switch to a sleep analysis mode. In the sleep analysis mode, the analysis tool can monitor the heart rate measurements, the activity level measurements, the body temperature measurements, the blood pressure measurements, and/or the blood oxygenation measurements of the user to determine different stages of sleep of the user and the period of time the user is in each stage of sleep. The different stages of sleep can include a nonrapid eye movement (NREM) sleep stage and a REM sleep stage. The analysis tool can determine when the user is in the NREM sleep stage based on the heart rate measurements, the activity level measurements, the body temperature measurement, the blood pressure measurement, and/or the blood oxygenation measurement being within a first range or at first level. The analysis tool can also determine when the user is in the REM sleep stage based on the heart rate measurements, the activity level measurements, the body temperature measurement, the blood pressure measurement, and/or the blood oxygenation measurement being within a second range or at a second level. For example, when a user switches from wakefulness to non-REM sleep the heart rate, blood pressure, activity level, body temperature, and blood pressure may decrease and blood oxygenation level may increase. When the user the transitions from NREM sleep to REM sleep the blood pressure, activity level, and heart rate may increase above an NREM level but below a wakeful level while the body temperature and blood oxygenation level may decrease below the NREM level. In this example, the analysis tool can use predefined ranges or levels to determine when the user enters each sleep stage. In another example, the analysis tool can monitor trending information or a change in measurement data to determine when the user enters each sleep stage. In another example, the analysis tool can set a range or level for each sleep stage (such as a predefined range or level) and can iteratively update the ranges or levels for each sleep stage as the analysis tool monitors the user over a period of time.

In another example, the analysis tool can determine when the user may be experiencing periods of sleep apnea. For example, the analysis tool can monitor for irregular or sudden changes in one or more of the measurements taken during the sleep stages. When there is a sudden change in one or more of the measurements, the analysis tool may determine that the user is experiencing a sleep apnea episode. For example, when the oxygenation level of the user decreases and the activity level, blood pressure, and heart rate increase, these changes can indicate that the user may be experiencing sleep apnea because the user may be more active and consume more oxygen during a sleep apnea episode.

Prolonged or extended high-stress levels of an individual or heavy physical training or exercise without adequate recovery can increase a risk of an injury for the individual. The analysis tool can forecast or estimate when a user may experience an injury and preventatively alert the user.

In one example, the analysis tool can monitor a heart rate, a change in heart rate, and/or heart rate variability (HRV) measurements to determine stress states of the user, such as when the body of a user is in a mental stress state, recovering or relaxation state, or a physical exercise state. Heart rate variability (HRV) can be a difference in times between successive heartbeats.

In one example, the analysis tool can determine an amount of time the user is in one or more stress states to forecast or estimate when an injury may occur. For example, when a user may be in physical exercise state and/or a mental stressed state for an extended period of time and has minimal time in a recovering or relaxing state, a risk of an injury occurring can increase as the body of the individual may not have adequate time to recover and regenerate. The analysis tool can forecast or estimate when an injury may occur based on an amount of time a user may be in one or more of the stress states.

In another example, the analysis tool can monitor the stress states in combination with monitoring other states of the user, such as sleep states. When a user's body does not receive a threshold amount of sleep and/or a threshold amount of a type of sleep (such as REM sleep), the body may have insufficient time to secretes hormones to build up an immune system of the user, increase muscle mass of the user, increase bone strength of the user, and increase an energy level of the user. Additionally, when the amount of sleep or stage of sleep the user enters is below a threshold amount, a user can experience muscle atrophy and a decrease in an ability to build and repair muscles. The analysis tool can also determine sleep latencies, sleep fragmentation, decreased sleep efficiency, and/or a frequency of sleep arousals.

The analysis tool can monitor an amount of time the user spends in a sleep state and/or the amount of time the user spends in different stages of sleep to determine an amount of sleep and/or stages of sleep of the user. Based on the amount of sleep and/or stages of sleep of the user, the analysis tool can forecast or estimate an increase in injury based on an amount of time the user's body has to recover. In one example, when the analysis tool determines that an injury risk level exceeds a threshold level, the analysis tool can send an alert to the user, via the UMD or another display device.

In another example, the analysis tool can forecast or estimate when an injury may occur in the future or may currently be occurring based on a change in intensity of physical activity and/or an amount of physical activity the user performs. For example, when the user historically performed a physical activity at an intensity level for a period of time and then decrease the intensity of the physical activity and/or the amount of time the physical activity may be performed, the analysis tool can determine that the user may be experiencing an injury or that a probability that an injury may occur can be increasing. In one example, the activity intensity can be measured based on acceleration during a run, deceleration during the run, speed of the run, jumping height, lateral movement or agility, heart rate, recovery rate, oxygenation level, and so on.

In one example, the analysis tool can predict when an injury may occur based on measurements that occurred during a previous injury. In this example, the analysis tool can maintain a database of measurements taken prior to the previous injury occurring, during the previous injury, and/or after the injury occurred. The analysis tool can compare current measurements of the user with the previous measurements to forecast or predict when another injury may occur based on a correlation or similarity of the measurements.

For example, a user may begin favoring one leg over the other when jumping, similarly to when a previous injury occurred. The analysis tool can use a sensor, such as an accelerometer or a gyroscope, to determine when a jumping movement may be similar to a previous injury and can forecast or predict when an injury may occur.

In another example, the analysis tool can weigh different measurements and/or user profile information when forecasting or predicting an injury. For example, the analysis tool can weight measurement data for a first individual differently than for the second individual based on an age, height, weight, injury history, nutrition level, and gender of the two individuals.

In another example, the analysis tool can determine a recovery of an individual from an injury based on similar measurements and/or analysis as discussed in the preceding paragraphs.

The analysis tool can determine a change in the activity (e.g., a suggested or recommended course of action) of the user based on the measurements discussed in the preceding and proceeding paragraphs. In one example, when the analysis tool determines that an injury risk level has increased above a threshold level, the analysis tool can determine a change in user activities to decrease the injury risk level. For example, when the analysis tool determines an increased injury risk level, the analysis tool can determine that the user can decrease an amount of physical activity and increase an amount of time the user sleeps or recovers. In another example, when the analysis tool determines that a heart rate or blood pressure of an individual exceeds a threshold amount, the analysis tool may determine a change in diet of the user to decrease the heart rate or blood pressure of the individual. The analysis tool may use a database or lookup table to determine a recommended course of action based on one or more measurements of the sensors of the UMD.

The analysis tool can recommend activities based on previous or historical measurement data and/or current measurement data. For example, the analysis tool can determine different measurements (a heart rate, a blood pressure, a hydration level change, and so forth) of a user for different activities. The analysis tool can compare the different measurements associated with the different activities to determine activities to increase a desired measurement of a user. For example, the analysis tool can identify an activity from multiple activities that may increase a heart rate of a user while not increasing a blood pressure level and dehydration level of the user. The analysis tool can communicate the identified activity to the user via a sensory indicator of the UMD or another computing device (such as a display).

The analysis tool can estimate or forecast measurement data of the user for different environments. In one example, a member of a sports team may have previously performed in a first environment (such as a relatively hot environment at a relatively high altitude) and may now be performing in a second environment (such as a relatively cold environment at a relatively low altitude). In this example, the analysis tool can determine a difference in the performance of the individual for the first and second environments. The analysis tool can then determine an adjustment value to adjust measurement data between the two environments. When the measurement data of the individual changes in the second environment, the analysis tool can convert the measurement data for the first environment.

In another example, the analysis tool can use the survey information or the profile information (as discussed in preceding and proceeding paragraphs) to determine the adjustment value. For example, a user may desire to estimate or forecast how the user's measurement data would change in an environment that the user has not taken measurement data at previously. In this example, the analysis tool can identify measurement data of another user that may have similar survey information or user profile information to the user. The analysis tool can then determine an adjustment value to adjust the user's measurement data based on the other user's measurement data. In another example, analysis tool can use environmental information to determine a similar environment to the environment of the user and convert the measurement data of the user selected environment based on an adjustment value for the similar environment.

In one example, the analysis tool can forecast or estimate an amount of fluid a user may intake and at what rate for the user to return to a hydrated level. The analysis tool can monitor a trending of a user's hydration level over a period of time as the hydration level of the individual decreases and increases. The analysis tool can determine the change in hydration level over time to determine a rate that the user may dehydrate at (e.g., a dehydration rate) and/or a rate that a user may rehydrate at (e.g., a rehydration rate). For example, the analysis tool can determine that the user may transition from a hydrated state to a dehydrated state over a period of 20 minutes when performing an activity (such as running) based on the trending information and may transition from a dehydrated state to a hydrated state over a period of 30 minutes when resting and drinking fluid.

In one example, the analysis tool can iteratively determine the dehydration rate and/or the rehydration rate. For example, the analysis tool can use an initial trending information of the transition from the hydrated state to a dehydrated state to set an initial dehydration rate. The analysis tool can then continue to monitor the user's transitions between hydrated and dehydrated states to iteratively update the dehydration rate. In one example, the analysis tool can take an average of the trending data and update a current dehydration rate with the current trending information. In another example, the analysis tool can assign weights the trending information, with the current trending information having a larger weight and the older trending data having successively smaller weight.

In one example, the analysis tool can track trending information of one or more measurements or diagnosis. In this example, based on the trending information, the analysis tool can determine when measurements or diagnoses of a user indicate that a user is trending from one diagnosis level to another diagnosis level. For example, the analysis tool can monitor a user's hydration level measurements to determine when a user is trending from a hydrated level to a dehydrated level. In another example, when the analysis tool determines a user is trending in an undesired direction (such as from hydrated to dehydrated), the analysis tool can determine a treatment regimen. For example, when a user is trending from a hydrated state to a dehydrated state, the analysis tool can forecast when the user may switch to a dehydrated state and determine a rehydration treatment regimen for a user. In this example, the UMD can indicate to a user an amount of fluid to intake. The analysis tool can monitor the trending information of a user to determine when the treatment regimen may be completed. For example, when the trending information indicates that the user has rehydrated to his or her original hydration level, the analysis tool can determine that the user has been rehydrated.

The analysis tool can determine a metabolic rate of the user based on profile information and/or measurement data of a user. In one example, the analysis tool can determine a resting metabolic rate (RMR). The analysis tool can determine the RMR of a user using a look-up table at a storage device coupled to the analysis tool. The look-up table can include RMR information associated with different profiles of individuals (such as height, weight, age, and gender). The analysis tool can identify a profile from the different profiles of individuals that match the profile of the user (either an exact match or a match within a matching range). The analysis tool can then set the RMR of the user based on the RMR of the matching individual.

In one example, the analysis tool can adjust the RMR of an individual in view of additional information. The additional information can include: weather information, e.g., living in a cold environment can increase the RMR; frequency of meals consumed, e.g., small regular meals can increase the RMR; pregnancy information, e.g., a pregnancy can increase the RMR; diet change, e.g., a crash-diet or fad diet may decrease the RMR; and dietary or nutritional supplement usage, e.g., dietary or nutritional supplements can raise the RMR.

When the analysis tool has set the RMR for the user, the analysis tool can determine an activity level of the user. For example, the analysis tool can determine a frequency and duration that an individual may physically exert himself or herself. When the analysis tool has determined the RMR and the user activity level, the analysis tool can then use an algorithm, such as a Harris Benedict equation to determine a metabolic rate (e.g., a rate that an individual burns calories) of the user. For example, when the analysis tool determines that a user has a low activity level, the analysis tool can determine the metabolic rate using RMR×1.2=metabolic rate. In another example, when the analysis tool determines that a user has a light activity level, the analysis tool can determine the metabolic rate using RMR×1.375=metabolic rate. When the analysis tool determines that a user has a moderate activity level, the analysis tool can determine the metabolic rate using RMR×1.55=metabolic rate. When the analysis tool determines that a user has a high activity level, the analysis tool can determine the metabolic rate using RMR×1.725=metabolic rate. When the analysis tool determines that a user has a very high activity level, the analysis tool can determine the metabolic rate using RMR*1.9=metabolic rate.

The analysis tool can associate the input data with a user. In one example, the analysis tool can create a user identification (ID) for a user of the UMD. The analysis tool can then associate the user ID with input data (such as measurement data and/or user data) for the user, such as by tagging or appending the user ID to the input data. For example, the input data can be stored in data fields and the user ID tag can be appended to the data fields. In another example, a separate data field can be created for the user ID.

When the user may be associated with a group of individuals, a group ID can also be associated with the input data. In one example, the user ID and the group ID can be included in a combined data field. In another example, the user ID and the group ID can use separate data fields. In one example, the user can be a member of a first sports team. A first group ID can be associated with the first sports team. While the member may be part of the first sports team, the measurement data and/or user data can be tagged with the first group ID for the first sports team. When the member switches or moves to a second sports team, the user ID can remain the same and the first group ID can be switched to a second group ID. An advantage of using different group IDs for different groups of individuals (such as different sports teams) can be to provide data mobility. For example, regardless of which group the user may be part of at a given point in time, the input data can be associated with the user and when the user leaves a group or switches to another group the input data can continue to be associated with the individual (e.g., the input data can follow the user).

In another example, when a user switches groups, the input data collected while the user was part of a first group can continue to be tagged with the first group ID and new data can be tagged with the second group ID. An advantage of maintaining the association of the group ID with the group when the input data was collected can be to enable sorting of the input data based on what group the user was a part of when the input data was collected. For example, when a first set of input data was taken when the user was a member of the Utah Jazz basketball team, the first set of input data can continue to be associated with the Utah Jazz when the user moves to Chicago Bulls basketball team. In this example, an individual (such as a coach or trainer) can use the group IDs for the different teams to sort the input data based on when the member played for each team.

Figure 2A:
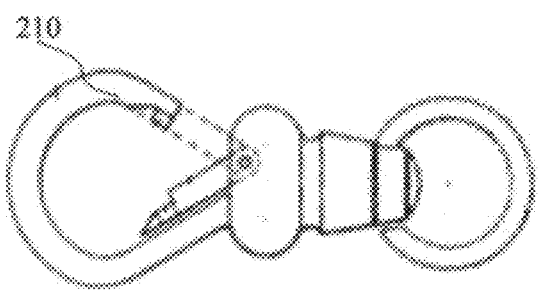
FIG. 2B shows a base station configured as a hanger according to one embodiment.
FIG. 2C shows a base station configured as a holder with a UMD coupled or attached to the holder according to one embodiment.
FIG. 2D shows a base station configured as a plate according to one embodiment.
Figure 2B:
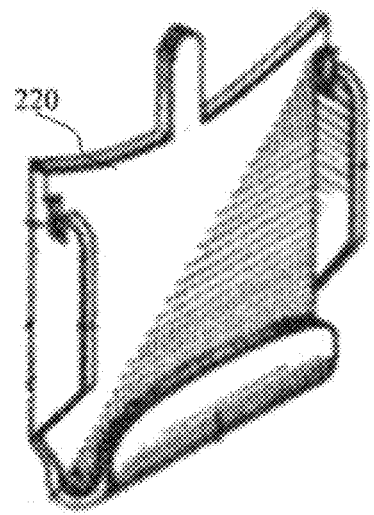
Figure 2C:
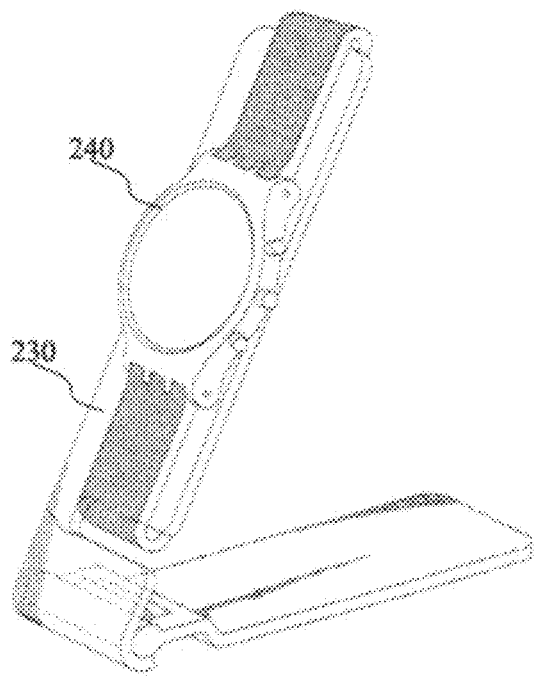
Figure 2D:
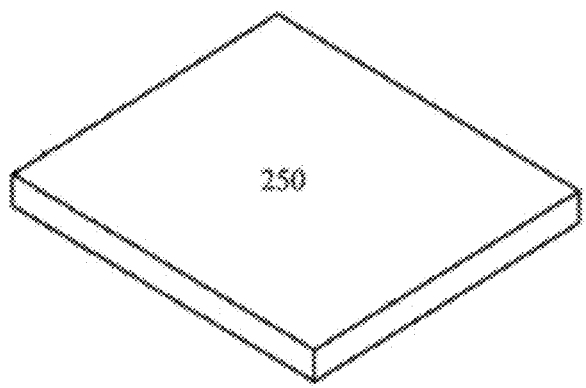

FIGS. 2A-2D show various exemplary embodiments of a base station. FIG. 2A shows a base station configured as a hook 210 according to one embodiment. In one example, a UMD can be hung from the hook. FIG. 2B shows a base station configured as a hanger 220 according to one embodiment. In one example, a UMD can be hung from the hanger. FIG. 2C shows a base station configured as a holder 230 with a UMD 240 coupled or attached to the holder 230 according to one embodiment. FIG. 2D shows a base station configured as a plate 250 according to one embodiment.

In one example, multiple UMDs can communicate with a base station or hub device. For example, multiple members on a sports team can use different UMDs to take measurements. The UMDs of each member can communicate the input data back to the base station or hub device. The base station or hub device can store the information and/or relay the information to an application (such as a cloud-based application) to display to a user. In one example, each UMD can communicate the input data to the base station or hub device in real-time using different communications channels or frequencies. An advantage of communicating the input data in real-time can be to provide a user with the input data as measurements may be taken or other input information may be received.

In another example, the multiple UMDs can communicate using a same channel or frequency and can stagger the communications. For example, each UMD can have an internal clock and each UMD can have different designated times to communicate the measurement data to the base station or hub device. In another example, the UMDs can communicate with each other and can coordinate when to communicate input data to the hub device. The UMDs can coordinate or synchronize an order to communicate the measurement data based on one or more criteria. The criteria can include: an priority level of the input data, a period since the last time a UMD communicated input data to the hub device, an amount of input data the UMD may communicate to the hub device, a bandwidth rate of the UMD to communicate the input data, a location of the UMD in relation to the hub device, a number of UMDs requesting to communicate with the hub device, a type of the UMD requesting to communicate with the hub device, and so forth. In another example, the UMDs can communicate to the hub device in a defined order, such as a first in first out (FIFO) order. In one example, the multiple UMDs can communicate with the hub device in a staggered order. For example, a first UMD can communicate to the UMD within a first period of time and a second UMD can communicate to the hub device within a second period of time, where the first period of time and the second period to time may be different (e.g., staggered periods of time).

In another example, the UMDs can communicate with the hub device based on a location of the UMD. In one example, a UMD can communicate to the hub device based on the location of the UMD. For example, when the UMD comes within a proximity distance or threshold distance of the hub device, the UMD can communicate input data. In one example, the UMD can determine proximity using a location system such as GPS or triangulation. In another example, the UMD can determine the location using a pinging scheme or by sending a message to the hub station to determine its location. For example, when a player on a sports team may be using the UMD, when the UMD determines that the player may be sitting on the bench (e.g., not currently in the game) or at a location for a water break, the UMD can communicate the measurement data.

In another example, the UMD can receive a manual synchronization command. For example, the UMD can include a controller (such as a button, switch, or touch screen icon) on the UMD to receive a command from a user (e.g., the user presses the synchronization button) to communicate the input data. In another example, when the user places the UMD on a charging pad or connect the UMD to a charging cable, the UMD can be activated to communicate the input data.

In another example, the UMD can communicate a portion of information in real time and a portion of information periodically. For example, a portion of measurement data (such as data indicating a user may be dehydrated) can be designated as critical information (e.g., high priority data) and can be communicated to the hub device in real-time. In this example, other non-critical information, such as clock information, user profile updates, and so forth can be communicated on a periodic basis (such as a periodic data dump of non-critical information).

Figure 3A:
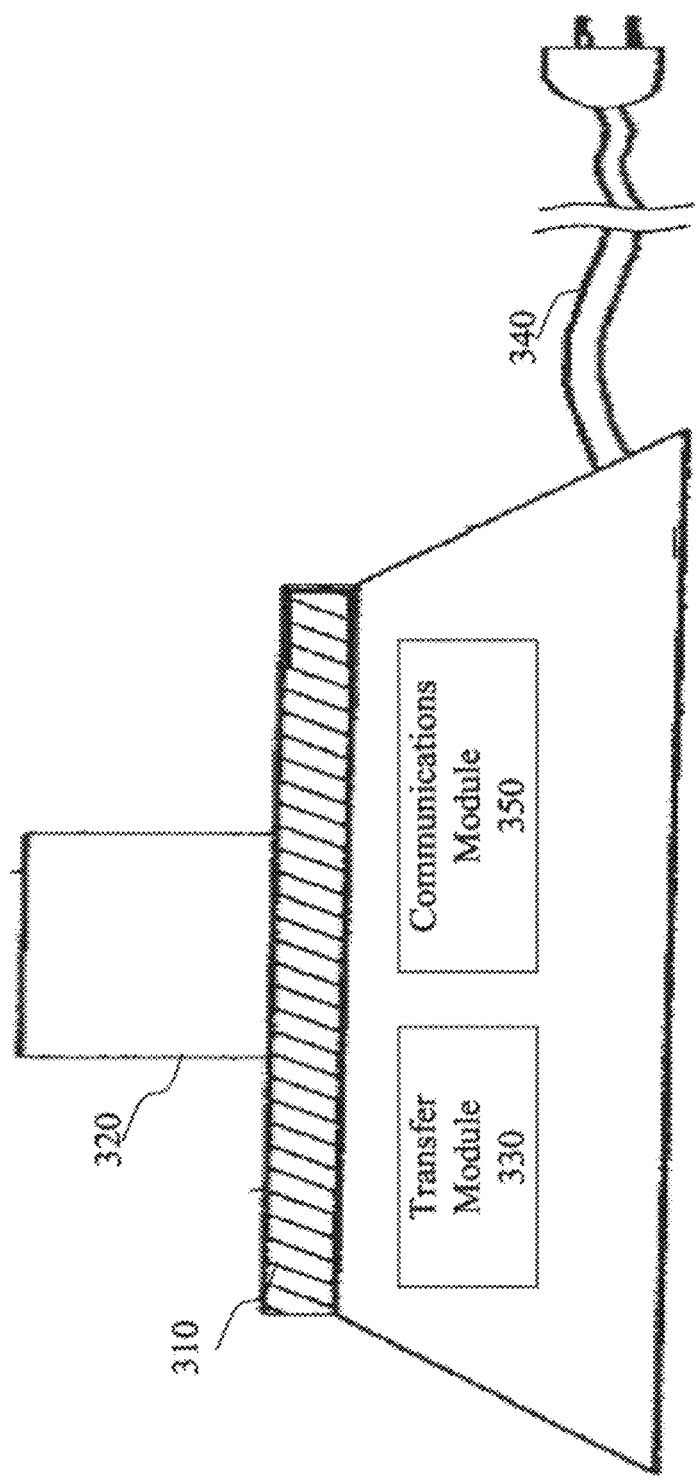
FIG. 3A shows another exemplary embodiment of a base station configured to transfer data and power with a UMD according to one embodiment.

FIG. 3A shows another exemplary embodiment of a base or base station 310 configured to transfer data and/or power with a UMD 320 according to one embodiment. In one embodiment, the base station can be configured to communicate data, such as input data, with the UMD using a transfer module 330. In another embodiment, the base station 310 can be configured to transfer power with the UMD 320 using the transfer module 330. In one example, the base station 310 can transfer power using a physical electrical connection, such as a universal serial bus (USB) connection. In another example, the transfer module 330 and/or the base station 310 can include one or more wireless transfer coils and the base station 310 can be configured to wirelessly transfer power to the UMD 320 using the one or more wireless transfer coils.

In one configuration, the base station 310 can be connected to a power outlet (such as a wall power outlet) and/or a communication port (such as an Ethernet port) using a transfer connector 340. In one embodiment, the base station 310 can receive power from the power outlet using the transfer connector 340. In another embodiment, the base station 310 can communicate data, such as sync data, with another base station or another computing device (such as a server or cloud storage device as discussed in the proceeding paragraphs) using the transfer connector 340. In another embodiment, the base station 310 can communicate data with one or more UMDs, one or more other base stations, and/or other devices using a communication module 350. In one embodiment, the communications module 350 can communicate the data using a cellular network and/or a wireless network.

In one example, the communications network can be a cellular network that may be a third generation partnership project (3GPP) release 8, 9, 10, 11, or 12 or Institute of Electronics and Electrical Engineers (IEEE) 802.16p, 802.16n, 802.16m—2011, 802.16h—2010, 802.16j—2009, 802.16 —2009. In another embodiment, the communications network can be a wireless network (such as a wireless local area network (e.g., network using Wi-Fi® technology) that may follow a standard such as the IEEE 802.11 —2012, IEEE 802.11ac, or IEEE 802.11ad standard. In another embodiment, the communications network can be a PAN connection (e.g., a connection using Bluetooth® technology) such as Bluetooth® v1.0, Bluetooth® v2.0, Bluetooth® v3.0, or Bluetooth v4.0. In another embodiment, the communications network can be a PAN connection (e.g., a connection using the Zigbee® technology), such as IEEE 802.15.4 —2003 (Zigbee® 2003), IEEE 802.15.4 —2006 (Zigbee® 2006), IEEE 802.15.4 —2007 (Zigbee® Pro). In one embodiment, the base station and the UMD can use near-field communication, or induction communication to communicate information between the base station and the UMD.

In one example, the UMD can communicate input data to the base station at selected times of the day. In another example, the UMD can communicate input data with the base station at a selected time when the user wakes up in the morning and at a selected time when the user goes to sleep at night. In another embodiment, the base station can communicate input data with other devices such as computers, phones, tablets, medical equipment, display devices, and so forth.

Figure 3B:
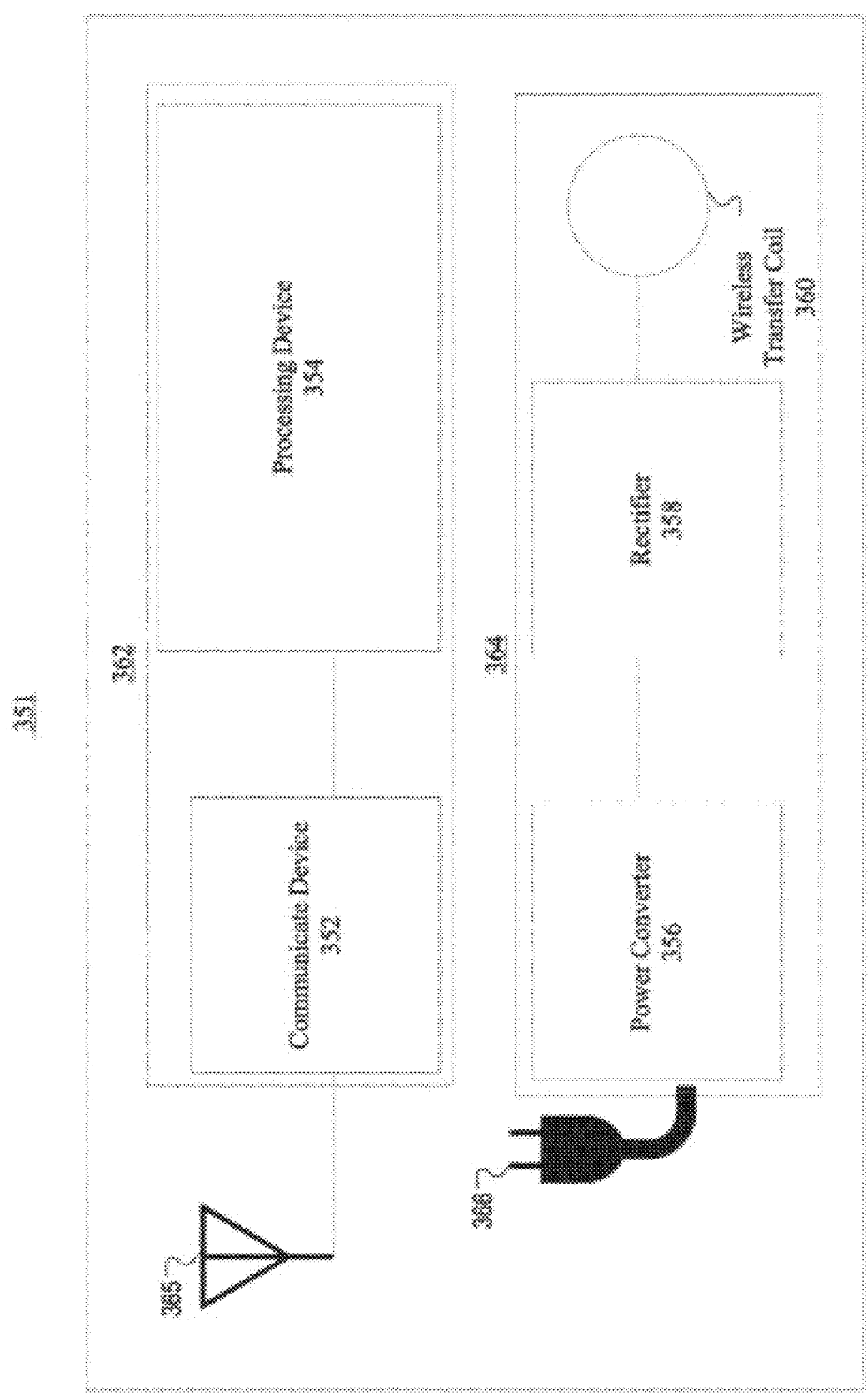
FIG. 3B illustrates a schematic view of the base station according to one embodiment.

FIG. 3B illustrates a schematic view of the base station 351 according to one embodiment. The base station 351 can include a data transfer device 362 and a power management device 364. In one example, the data transfer device 362 can include a communication device 352 and a processing device 354. The communication device 352 can be coupled to an antenna 365, where the antenna can be configured to communicate with another device such as a UMD via a wireless network and/or a cellular network. In one example, the communication device can be a transceiver, communicating data between a processing device 354 coupled to the communication device 352 and another device. In one embodiment, the processing device 354 can include a processor to analyze data received from another device. In another embodiment, the processing device 354 can be connected to the computing device and transfer data between the other device and the computing device, where the computing device can analyze the data. In one example, the computing device can be a server or a cloud-based device. The power management device 364 can include a power converter 356 that can be coupled to a power source 366. In one example, the power source 366 can be an alternating current (AC) power source and the power converter 356 can convert the AC power to DC power. In another embodiment, the power management device 364 can include a rectifier or oscillator 358 to receive the DC power from the power converter can transfer the power to a wireless transfer coil 360 for wireless power transfer. In this example, the rectifier or oscillator 358 can be an impedance matching circuit to match an impedance level of the wireless transfer coil 360 with a wireless transfer coil of another device.

Figure 4A:
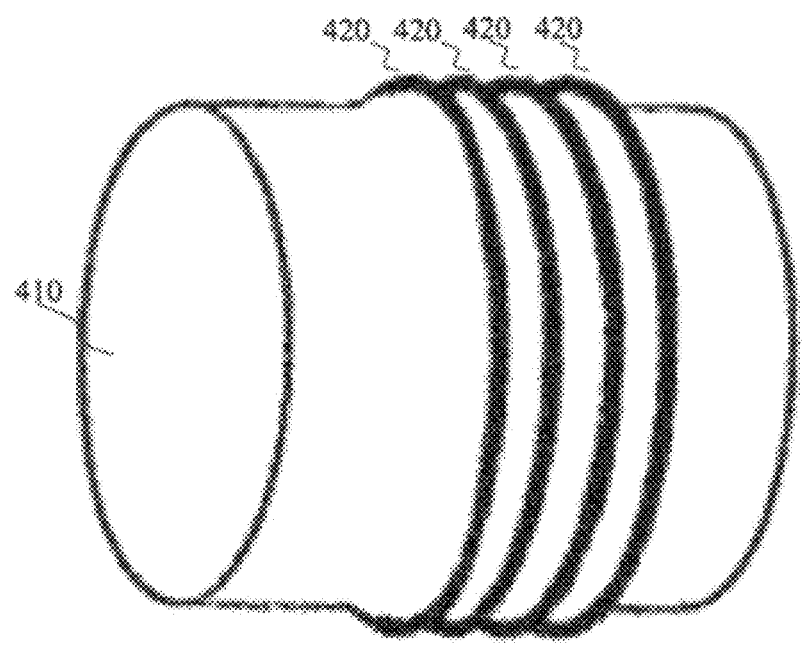
FIG. 4A depicts one exemplary embodiment of the base station sized and shaped as a cylindrical platform coupled to the multiple UMDs according to one embodiment.
Figure 4B:
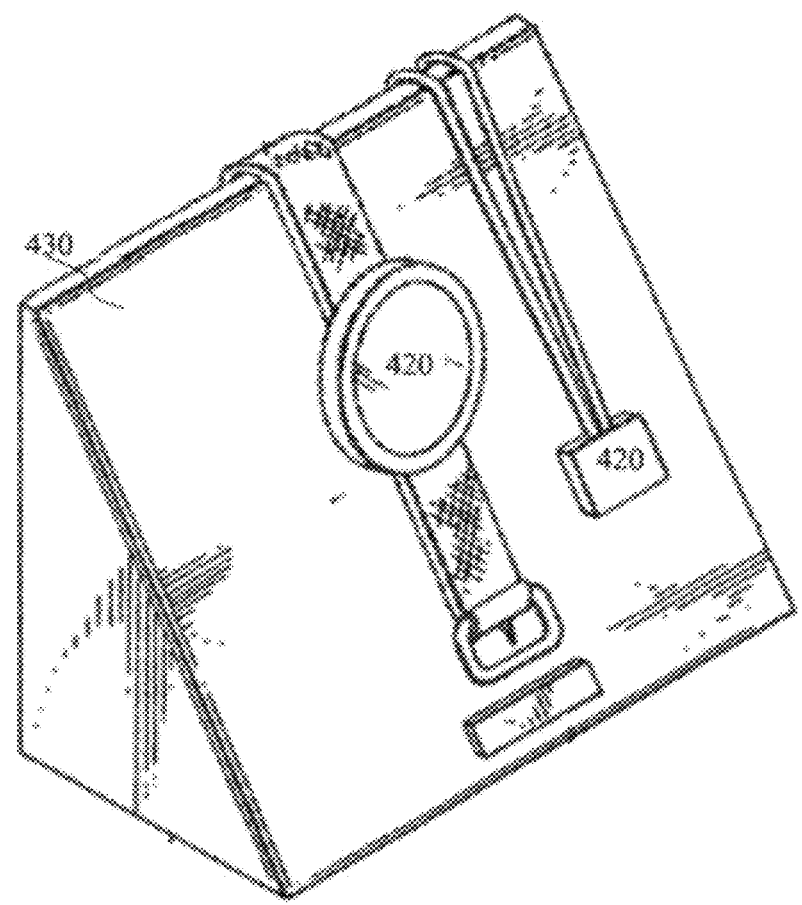
FIG. 4B depicts another exemplary embodiment of the base station sized and shaped as a podium or pedestal platform coupled to the multiple UMDs according to one embodiment.

FIGS. 4A and 4B depict a base station 410 and multiple UMDs 420. FIG. 4A depicts one exemplary embodiment of the base station 410 sized and shaped as a cylindrical platform coupled to the multiple UMDs 420 according to one embodiment. FIG. 4B depicts another exemplary embodiment of the base station 430 sized and shaped as a podium or pedestal platform coupled to the multiple UMDs 420 according to one embodiment.

In one embodiment, the analysis tool can monitor one or more sensors of the UMD to determine when the sensors are no longer taking measurements of the user of the UMD. In another embodiment, the one or more sensors can include: an optical sensor, an impedance sensor, a bioimpedance sensor, an electrocardiogram (ECG) sensor, an accelerometer, an altimeter, a pulse oximeter sensor, a fluid level sensor, an oxygen saturation sensor, a body temperature sensor (e.g., a skin temperature sensor), a plethysmograph sensor, a respiration sensor, a breath sensor, a cardiac sensor, a hydration level sensor, a humidity sensor, ambient temperature sensor, altitude sensor, barometer, a gyroscope sensor, a vibration sensor, an accelerometer sensor, 3d accelerometer sensor, force sensor, pedometer, strain gauge, and so forth. In one example, the sensors may no longer be taking measurements of the user when there is a sudden shift or change in measurement data of one or more sensors of the UMD. In another example, the sensors may no longer be taking measurements of the user when one or more measurements may be zero, near zero, or unknown. In another example, the sensors are no longer taking measurements of the user when one or more measurements are outside a selected threshold measurement range. When the sensors are no longer taking measurements of the user of the UMD, the UMD can determine that the UMD has been removed from the user and can communicate sync data with to the base station or another UMD.

The UMD can be further configured to establish a communication link, such as a cellular network communications link, a wireless network communications link, a device to device (D2D) communications link, a peer-to-peer (P2P) communications link, or a machine type communications link with the base station and/or the other UMD when the circuitry determines that the UMD has been removed from the body of the individual. The circuitry can be further configured to communicate sync data with the base station and/or the other UMD using the communications link.

Figure 5:
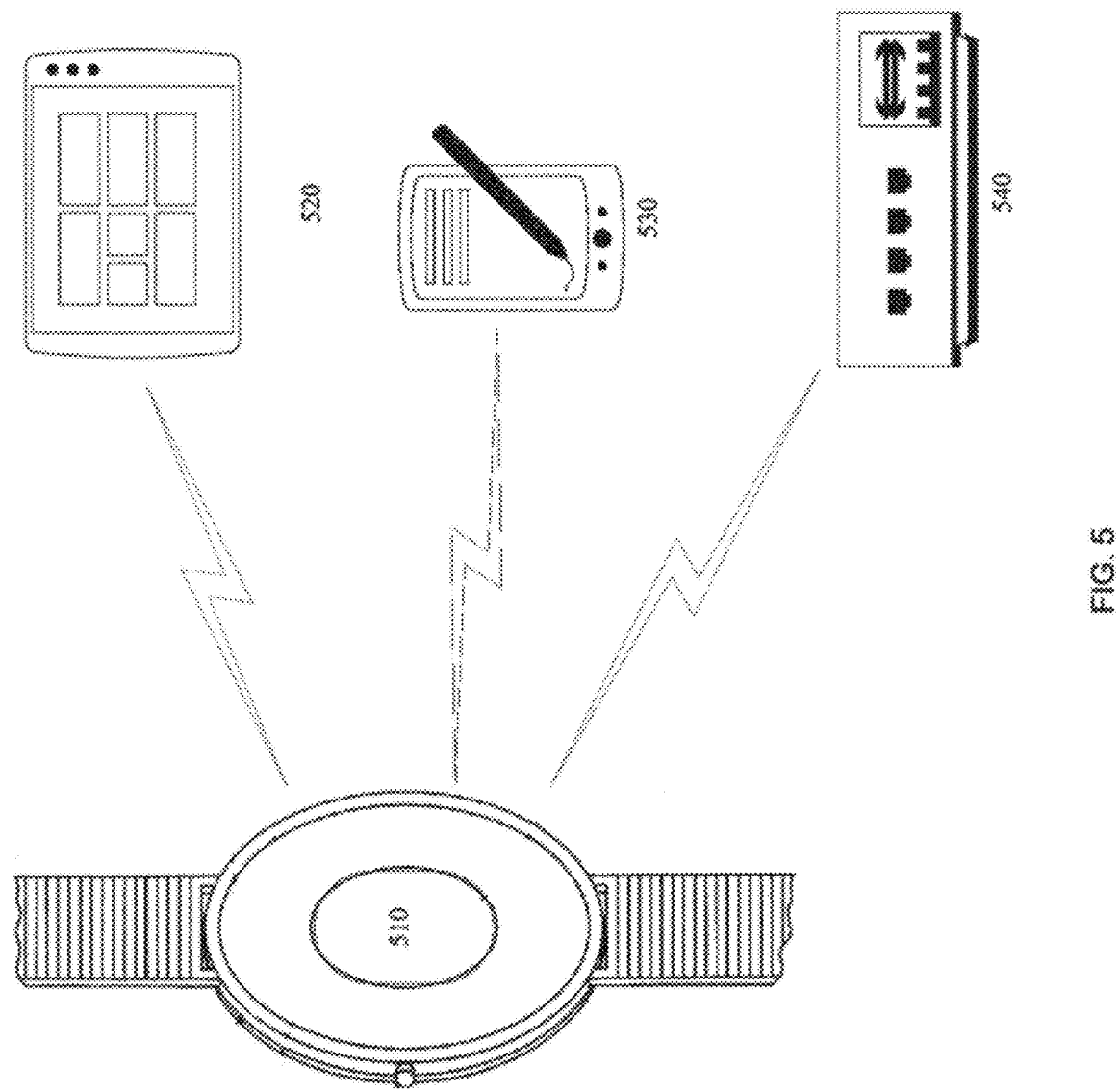
FIG. 5 depicts a base station or a UMD configured to communicate data with one or more other devices according to one embodiment.

FIG. 5 depicts a base station and/or a UMD 510 configured to communicate data, such as input data, with one or more other devices 520, 530, and/or 550 according to one embodiment. In one embodiment, the other devices can be non-wearable and/or non-portable devices, such as a bathroom scale or a bed scale 520, a medical device 530, and/or a continuous positive airway pressure (CPAP) device 550. In another embodiment, the base station and/or the UMD can store and/or analyze the data received from the one or more other devices separately from data of the base station and/or the UMD. In another embodiment, the base station and/or the UMD can aggregate the data received from the one or more other devices with the input data of the base station and/or the UMD. In another embodiment, the base station and/or the UMD can store, synchronize, and/or analyze the aggregated data of the one or more other devices and the base station and/or the UMD.

FIG. 6 illustrates a UMD and/or a base station 610 according to one embodiment. FIG. 6 further illustrates that the UMD and/or the base station 610 can include a wireless transfer coil 620 and a management module 630. In one example, the management module 630 of the UMD and/or the base station 610 can convert energy received at the wireless transfer coil 620 from an energy source, such as an alternating current (AC) energy outlet, to a selected current level, a selected voltage level, and/or a selected wattage level. In another embodiment, the UMD and/or the base station 610 can include one or more batteries 640, such as rechargeable batteries. In one embodiment, the wireless transfer coil can be a transmitting coil and/or a receiving coil (e.g., a transfer coil).

Figure 7:
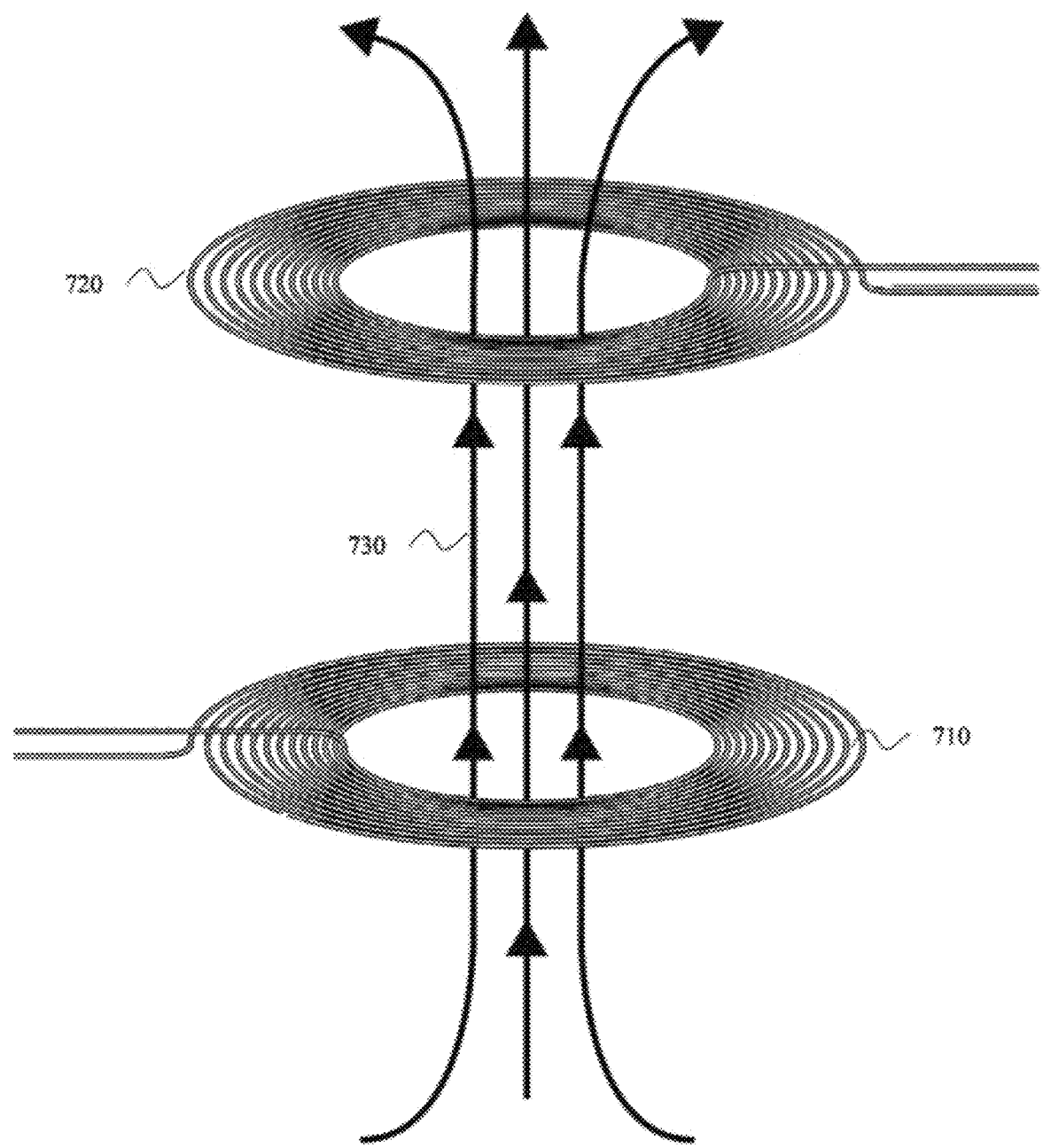
FIG. 7 illustrates transferring energy or data between multiple wireless transfer coils according to one embodiment.

FIG. 7 illustrates an example of transferring energy or data between multiple wireless transfer coils 710 and 720 according to one embodiment. FIG. 7 further illustrates that a first wireless transfer coil 710 can be a transmitting coil and a second wireless transfer coil 720 can be a receiving coil. In one embodiment, energy and/or data can be transferred from the transmitting coil to the receiving coil by coupling the transmitting coil with the receiving coil to enable the energy or data to be transferred over a gap or distance. In one example, wireless energy can be transferred by generating a magnetic field 730 at the transmitting coil and positioning the receiving coil within the magnetic field to induce a current at the receiving coil. In one embodiment, the magnetic field can be an electromagnetic field. Inducing a current at the receiving coil can be a coupling of the receiving coil to the transmitting coil. In one embodiment, the wireless transfer coil coupling for wireless energy or data transfer can be an induction coupling. In another embodiment, the wireless transfer coil coupling for wireless energy transfer can be a resonant coupling.

In one embodiment, the transmitting coil can be a transmitting induction coil and the receiving coil can be a receiving induction coil. The UMD and/or the base station can use a field (such as a magnetic field or a resonance field) to transfer energy between the transmitting coil coupled to a first object (such as a base station) and a receiving coil of a second object (such as a UMD) without any direct contact between the transmitting coil and the receiving coil, e.g. inductive coupling.

In one example, when the transmitting coil and the receiving coil may be within a threshold proximity distance, the transmitting coil and the receiving coil can couple to form an electric transformer. In one embodiment, current from the receiving coil can be transferred to a battery of the UMD or the base station. In one embodiment, an impedance of the transmitting coil can be substantially matched with an impedance of the receiving coil.

In one embodiment, the transmitting coil can be a transmitting resonant coil and the receiving coil can be a receiving resonant coil. A wireless resonant transfer can be a resonant transmission of energy or data between at the transmitting coil and the receiving coil. In another embodiment, the transmitting coil and the receiving coil can be tuned to resonate at a same frequency or a substantially same frequency.

In one example, resonant transmission of wireless energy can occur when the transmitting coil and the receiving coil are constructed to resonate at the same frequency or approximately the same frequency. The transmitting coil can be configured to oscillate current at a resonant frequency of the receiving coil to transfer energy and/or data. The oscillating current of the transmitting coil can generate an oscillating field at the selected resonant frequency of the receiving coil. When the receiving coil is positioned adjacent to the oscillating field and constructed to operate at the same frequency or substantially the same frequency as the transmitting coil, the receiving coil can receive energy and/or data from the oscillating magnetic field.

Figure 8A:
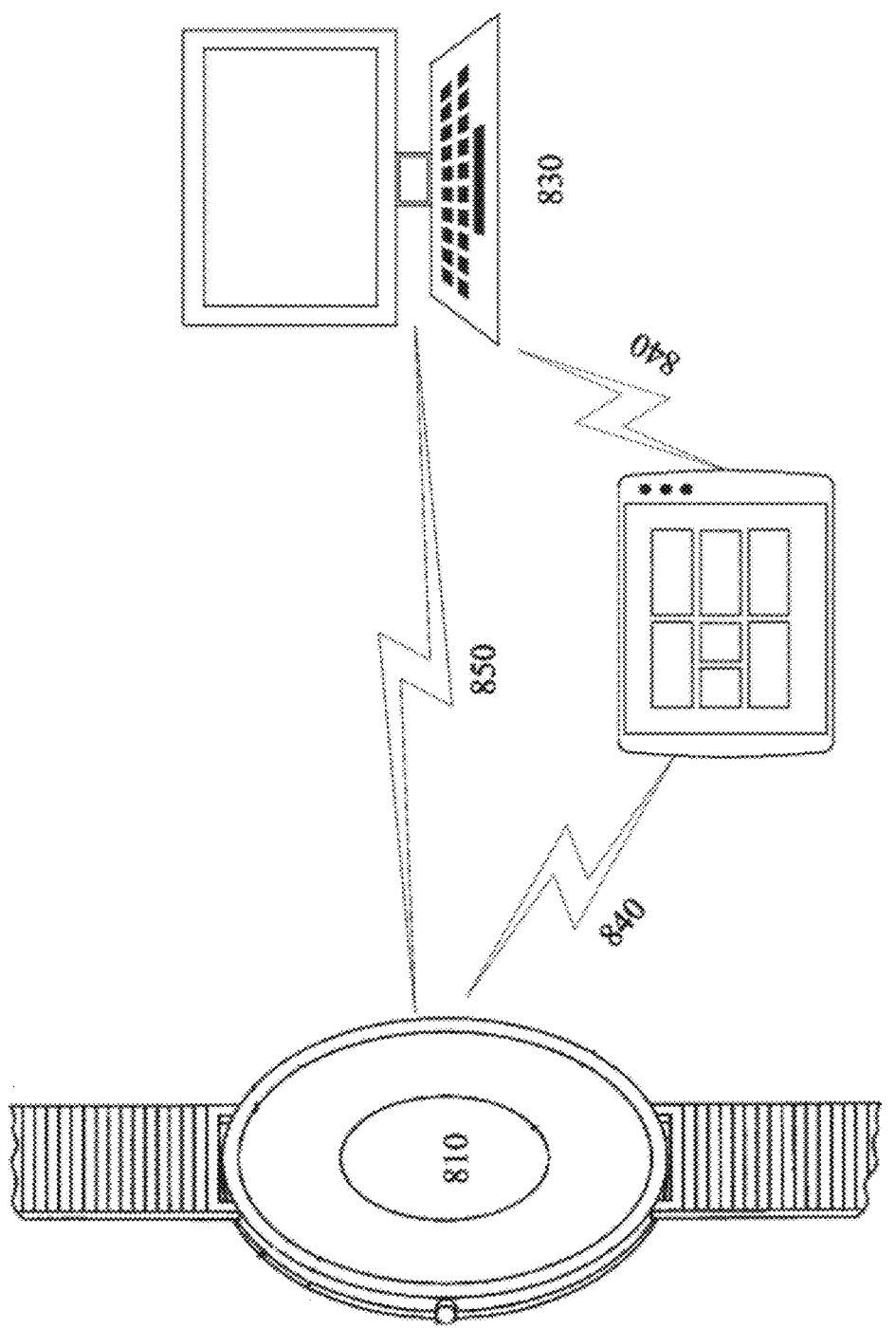
FIG. 8A illustrates a base station or a UMD operable to communicate sync data to a computing device according to one embodiment.

FIG. 8A illustrates a base station and/or a UMD 810 operable to communicate input data to a computing device 830, such as a server according to one embodiment. In one example, the base station and/or the UMD 810 can communicate input data directly to the computing device 830 using a communications connection 850 of a communications network. In another example, the base station and/or the UMD 810 can indirectly communicate the input data to the computing device 830 using another base station or another UMD 820 along communication connections 840.

FIG. 8A further illustrates that the base station and/or a UMD 810 can receive selected data or information, such as input data or other information, from the computing device 830. In one example, the base station and/or a UMD 810 can receive selected data or information for a user of the base station and/or a UMD 810 from a cloud-based server or a server in communication with a cloud-based server.

In one embodiment, the input data can include setting information for the base station and/or a UMD 810. In one example, the setting information can include: measurement data threshold ranges, measurement data threshold values, measurement event triggering values, and so forth. In another example, the input information can include: medical information of the user of a UMD, user condition information, medication regiment information, exercise regimen information, medical risk information, and so forth.

In another embodiment, the base station and/or a UMD 810 can provide a sensory indication (such as a visual, auditory, and/or touch indication) communicating the selected data or information to the user. In one example, the base station and/or a UMD 810 can display a reminder for a user to exercise, take medication, rehydrate, and so forth.

In one embodiment, the base station can analyze received input data and/or stored input data (such as measurement information) to determine selected states or conditions, such as medical conditions, physiological states, and so forth of the user of the UMD. In another embodiment, the base station can aggregate input data received from multiple UMDs. In another embodiment, the base station can aggregate current input data received from one or more UMD or other base station with previous input data stored at the base station or a device in communication with the base station. In another embodiment, the base station can analyze the aggregated sync data.

In one configuration, the base station can communicate other information to one or more UMDs. For example, the base station can receive software and/or firmware update information and relay the software and/or firmware update to the one or more UMDs. In one embodiment, the base station can communicate the other information to the one or more UMDs when the one or more UMDs receive energy (such as wired energy or wireless energy) from the base station.

Figure 8B:
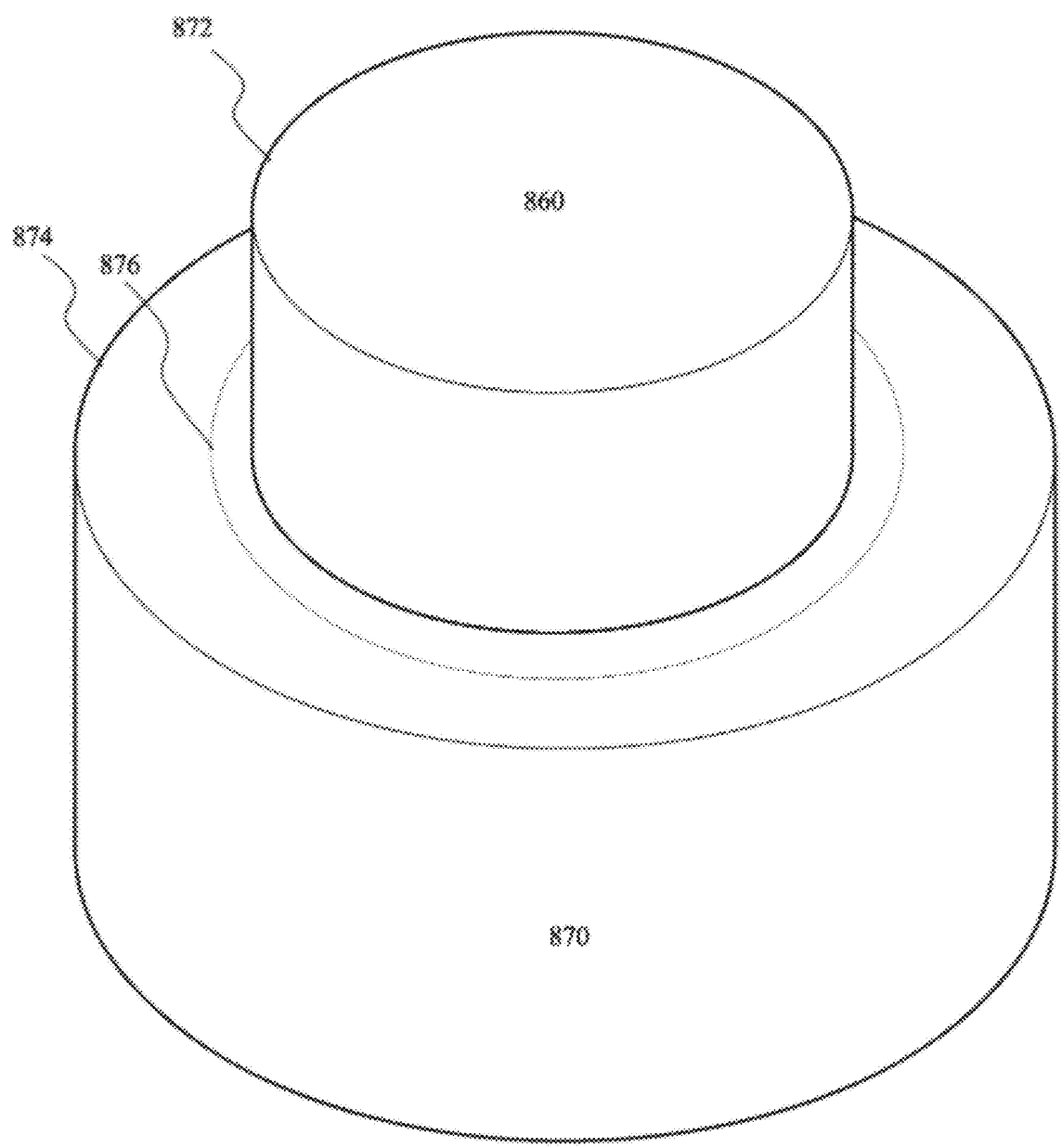
FIG. 8B illustrates a UMD and a base station according to one embodiment.

FIG. 8B illustrates a UMD 860 and a base station 870 according to one embodiment. The UMD 860 can include a wireless induction coil to transfer power and/or data. In one example, the UMD 860 can transfer power and/or data with a base station 870. The base station 870 can be sized and shaped to receive the UMD 860 and align a transfer coil of the UMD 860 with a transfer coil of the base station 870. For example, the UMD 860 can be sized and shaped to be a circular disk with a first radius 872 and the base station 870 can be a circular disk of a second radius 874. In this example, the second radius 874 of the base device can be larger than the first radius 872 of the UMD 860. The base station 870 can have a top surface with indentation or groove 876 that is a third radius and is approximately the same radius as the first radius 872. The UMD 860 can be sized and shaped to fit into the indentation or groove 876 when placed on the top surface of the base station 870. When the UMD 860 may be placed on the indentation 876, the transfer coils of the UMD 860 and the base station 870 can be aligned to enable wireless transfer of power and/or data using induction.

In one example, the UMD can communicate with external or third party equipment (e.g., equipment not integrated into the UMD). In another example, the UMD can receive information from the third party equipment (e.g., external information). In one example, the third party equipment can be a body weight scale that can determine a weight of an individual. In this example, the body weight scale can communicate weight information to the UMD. In another example, the third party equipment can be a smart water bottle that can monitor a fluid consumption of an individual. The UMD can aggregate the information for the third party equipment with the input data (such as measurement data) of the UMD.

In one example, the UMD can store the external information. In another example, the UMD can communicate the external information and the input data to the hub device. In another example, the hub device or the UMD can communicate the external information and/or the measurement data to a cloud-based computing device, where the cloud-based computing device can store and/or analyze the external information and/or the input data. An advantage of storing and/or analyzing the external information and/or the measurement data at the cloud-based computing device can provide the external information and/or the measurement data to a user from any location. For example, the UMD can take measurements of an individual (such as a player on an athletic team) and communicate the information to the cloud-based computing device. In this example, a coach or trainer can access the information from the cloud-based computing device at another location and view the measurement data of the player.

In one example, the UMD can be sealed to prevent fluid (such as water or sweat) or other materials from entering an inner cavity of the UMD. The inner cavity of the UMD can include circuitry, such as power management circuitry, processing circuitry, communication circuitry, and so forth. In one example, where the UMD includes a transfer coil to transfer data and/or power, the UMD may avoid traditional physical ports to transfer power and/or data (such as a USB port). In one example, the UMD can include two halves. The two halves can each include inner cavities to receive the circuitry. When the circuitry is placed inside the inner cavities, the two halves of the UMD can be sealed together to provide a fluid-proof outer surface (e.g., preventing fluid from entering the inner cavities).

In another example, when the UMD is sealed and transfer coils can be used to transfer power and/or data, a durability of the UMD can be increased. For example, by using transfer coils to transfer power and/or data, switches and ports along an external surface of the UMD can be reduced or eliminated. Traditionally, a port or switch can be a weak point in a device. For example, a switch uses mechanical contacts to perform a function, such as turning a device on and off. As the switch is used, the mechanical contacts can be worn out. Where the UMD reduces or eliminates the use of switches and ports, the mechanical contacts can be eliminated (e.g., the weak points of the device) and a durability of the device can be increased.

In one example, the UMD can include sensor devices to provide sensory indications to a user. In one example, the sensory device can be a visual sensory device, such as a display. The UMD can display information to a user using the visual sensory device. In another example, the sensory device can be an auditory sensory device, such as a speaker. The UMD can communicate information to a user using the auditory sensory device, such as communicating information to the user via the speaker. In another example, the sensory device can be a touch sensory device, such as a vibrator. The UMD can communicate information to a user using the touch sensory device. For example, the vibrator can vibrate for different periods of time or at different intervals to indicate different information to a user.

In one example, the UMD can be attached to different locations on a user's body using different UMD holders. For example, the UMD can be coupled with a wristband UMD holder to attach the UMD to a wrist position on the user. In another example, the UMD can be coupled with a headband UMD holder to attach the UMD to a head position (such as the forehead) on the user.

The UMD can determine the location on the user that the UMD may be taking measurements and can adjust the measurements being taken based on the location. For example, when the UMD may be located at a wrist of the user, the UMD can use an impedance spectrometer to take a hydration level measurement. In another example, when the UMD may be located at a forehead of the user, the UMD can use an accelerometer to take impact measurements (such as concussion measurements). The UMD can receive user input from an input device or an input controller that can part of the UMD indicating the location of the UMD on the user. An advantage of different UMD holders positioning the UMD at different locations on a user can be to enable optimal measurement taking for different types of measurements. For example, when a user desires to take a hydration measurement, the wrist may be an optimal location and the UMD can be coupled to the user with a wristband UMD holder. In this example, when a user desires to take an impact measurement, the forehead may be an optimal location and the UMD can be coupled to the user with a forehead UMD holder.

The different UMD holders can position or align the UMD to engage the body differently based on the location of the UMD. For example, a wrist location may be relatively flat for the UMD to engage the wrist and the forehead position may be relatively curved for the UMD to engage the forehead. The wristband UMD holder can align the UMD with the flat wrist or the curved forehead to enable the UMD to engage the body of the user and take measurements.

Figure 9A:
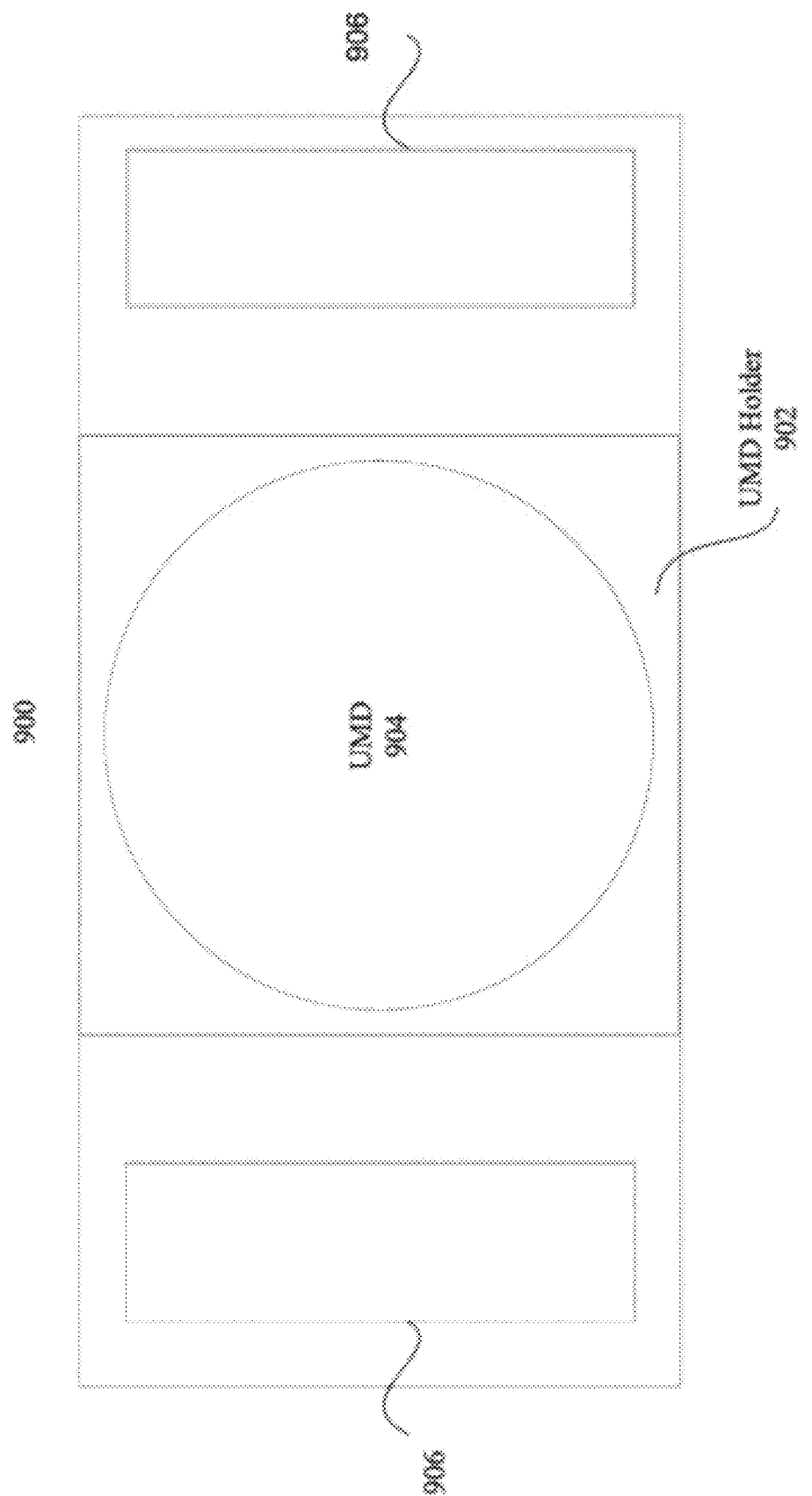
FIG. 9A illustrates a UMD holder according to one embodiment.

FIGS. 9A-9E illustrate various embodiments of UMD holders according to various embodiments. FIG. 9A illustrates a band or harness 900 with a UMD holder 902 formed and shaped to receive a UMD 904 according to one embodiment. In one embodiment, the UMD 904 can snap into an opening or a pocket formed and shaped to receive the UMD. For example, the UMD 904 can be circularly shaped and the UMD holder 902 can have a circular opening to receive the UMD 904. In one embodiment, the band or harness 900 can be a compression sleeve to attach to a body of a user. In another embodiment, the band or harness 900 can include fasteners 906 (such as Velcro®, snap fasteners, hooks, and so forth) to attach together to form a partial or complete band or harness 900 around a body part of a user.

Figure 9B:
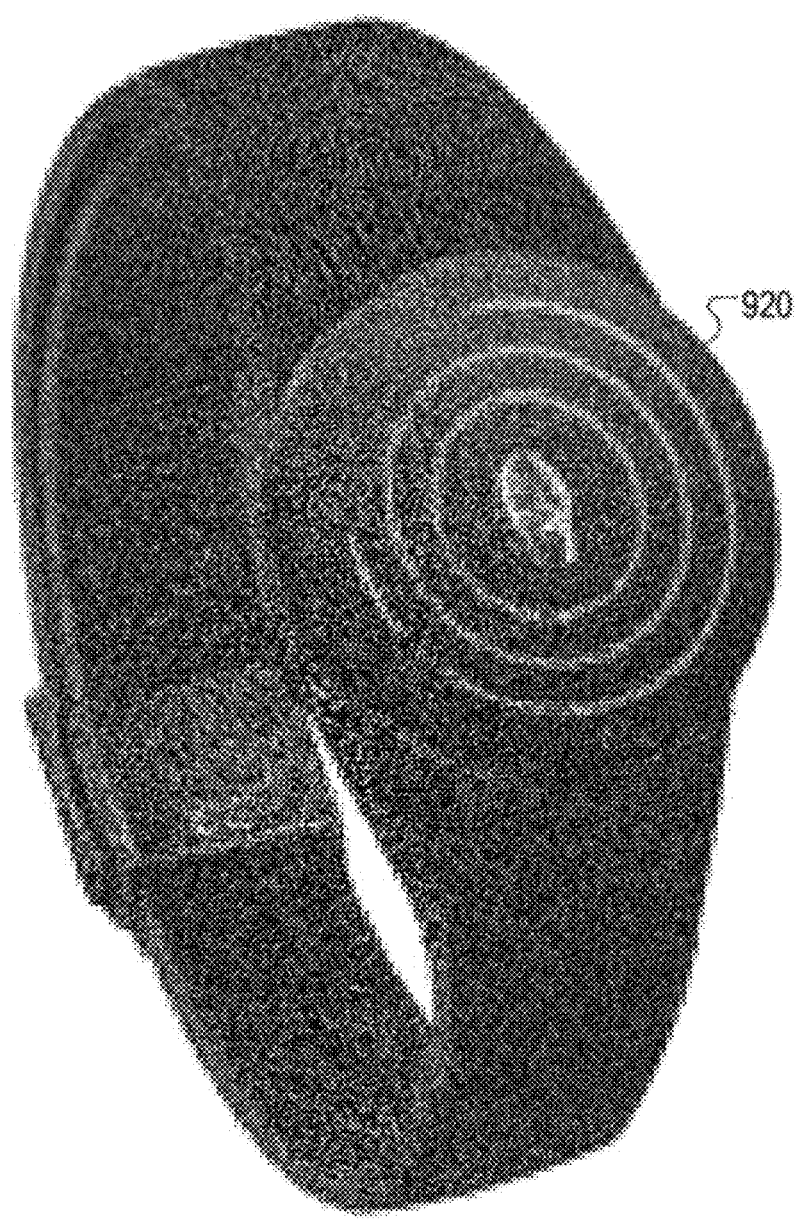
FIG. 9B illustrates a band or harness according to one embodiment.

FIG. 9B illustrates another band or harness 920 according to one embodiment. In one example, the band or harness 920 can be formed and shaped to receive a UMD (such as a circular puck) in a UMD holder. In another example, the UMD can be integrated into the band or harness 920.

Figure 9C:
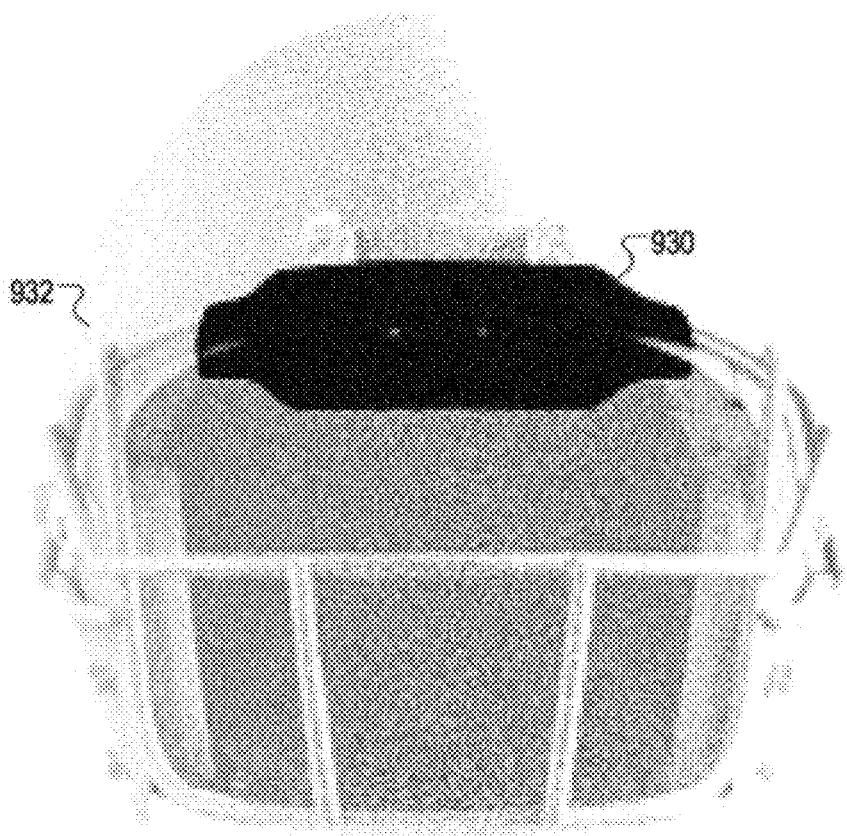
FIG. 9C illustrates another band or harness according to one embodiment.

FIG. 9C illustrates another band or harness 930 attached to an object 932 according to according to one embodiment. FIG. 9C further shows an exemplary embodiment where the band or harness 930 may be attached to an object 932, where the object 932 may be a football helmet. In one example, the band or harness 930 can include a UMD coupled to or integrated into the band or harness 930. In one example, the object 932 can be a helmet (such as a safety helmet or athletic helmet), a hat, clothing, and so forth.

Figure 9D:
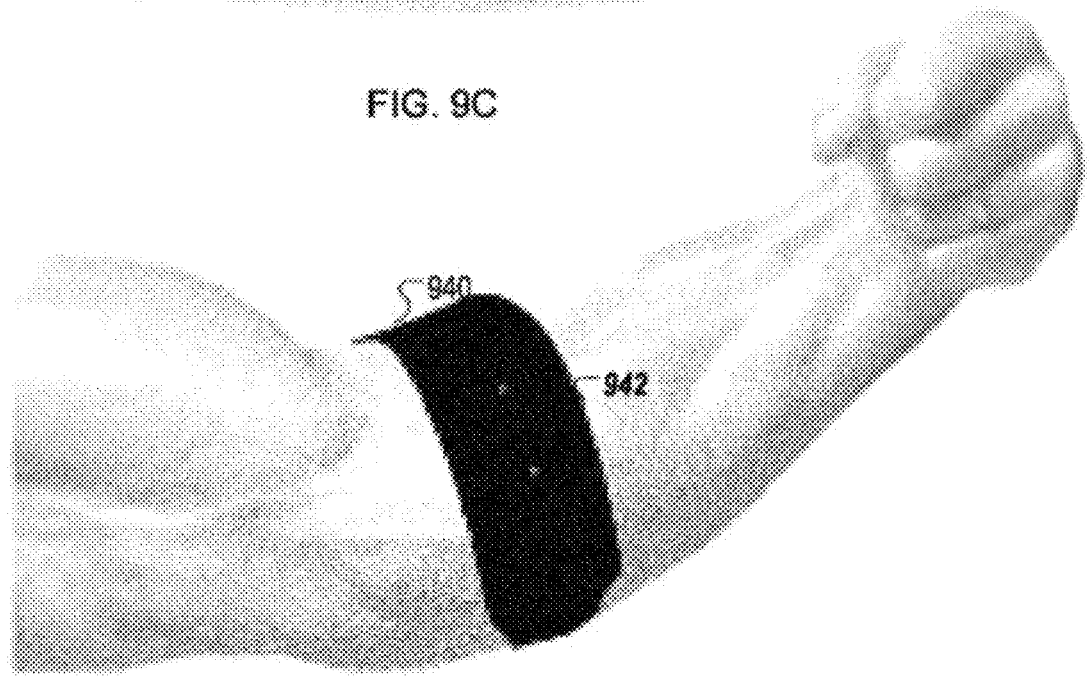
FIG. 9D illustrates a band or harness with an integrated UMD according to one embodiment.

FIG. 9D illustrates a band or harness 940 with an integrated UMD 942 according to one embodiment. FIG. 9D further shows an exemplary embodiment where the band or harness 930 may be integrated into a wristband, compression sleeve, or sweatband.

Figure 10A:
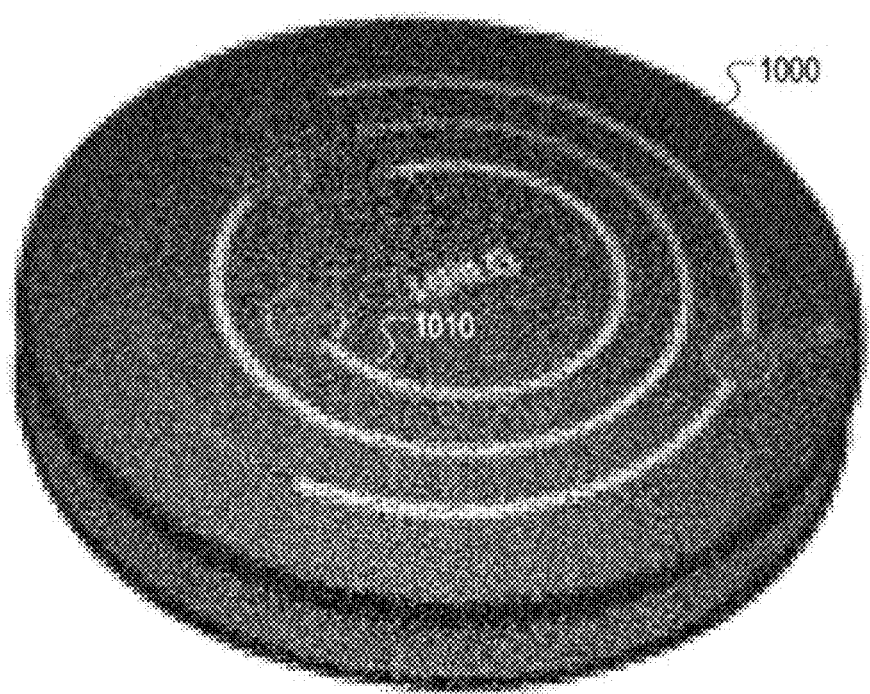
FIG. 10A illustrates a top view of a UMD with a display according to one embodiment.

FIG. 10A illustrates a top view of a UMD 1000 with a display 1010 according to one embodiment. In one example, the UMD 1000 can be a circular shape, a square shape, a rectangular shape, a cylindrical or oval shape, and so forth. In another example, the display 1010 can be a liquid crystal display (LCD) display a light emitting diode (LED) display, a touchscreen display, a backlight display, and so forth.

Figure 10B:
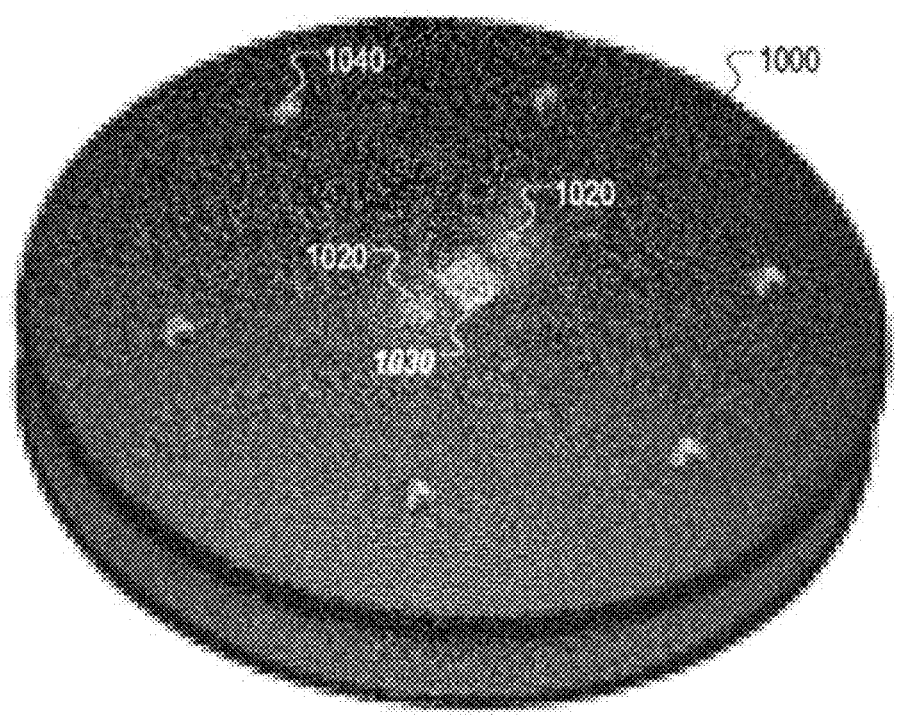
FIG. 10B illustrates a bottom view of a UMD with an optical sensor and electrodes according to one embodiment.

FIG. 10B illustrates a bottom view of the UMD 1000 with an optical sensor 1030 and electrodes 1040 according to one embodiment. In one example, the UMD 1000 can include light sources 1020, such as LED lights or candescent bulbs. When the UMD 1000 may be engaged to a body of a user, the light sources 1020 can illuminate one or more skin layers of the user. In one example, the optical sensor can measure an amount of light reflected by the one or more skin layers of the user. In another example, the optical sensor can measure an amount of light absorbed by the one or more skin layers of the user. When the UMD 1000 may be engaged to a body of a user, the electrodes 1040 can measure an impedance level of one or more skin layers of the user (e.g., measure bio-impedance levels).

In one example, the UMDs may be swappable. For example, a first UMD may be taking measurements of a user at a wrist location using the wristband UMD holder until the UMD runs out of power. When the UMD runs out of power, a user can switch the first UMD with a second UMD. In this example, the wristband UMD holder can maintain the same location to take measurements when the UMDs may be switched out. In this example, when the second UMD is coupled to the wristband UMD holder, the wristband UMD holder can align sensors in the sensor array of the UMD to take measurements at the same location or substantially the same location as the first UMD. An advantage of different UMDs taking measurements at the same location can be to reduce calibration errors and measurement errors. When a UMD engages the body and takes a measurement at different locations, the measurements may be calibrated for the different locations and may introduce errors or differences into measurement data. For example, when a first UMD takes measurements at a first location on the wrist and a second UMD takes measurements at a second location on the wrist, the first and second UMD may be calibrated differently based on the different locations and may provide different measurement information. When the UMD holder enables the first UMD and second UMD to engage the body at the same location or substantially the same location (e.g., a repeatable measurement location), the first and second UMD can use the same calibration information and reduce errors from different calibrations for different locations.

In one example, the UMDs can include one or more electrodes to take impedance spectroscopy measurements. An electrode can be a conductor through which a current can enter or leave the body of the user. In one example, the one or more electrodes can be spring-loaded electrodes (e.g., electrodes with springs to adjust a height of the electrodes). An advantage of spring-loaded electrodes can be to enable the electrodes to engage the body of the user and maintain a comfortable electrode height. For example, when the user places the UMD in a UMD holder, the UMD can have electrodes on a bottom surface of the UMD. When the electrodes engage the body a height of the electrodes can be automatically adjusted using the springs. Another advantage of the spring-loaded electrodes can be to secure the electrodes at a location of the user. For example, the springs can enable the electrodes to apply continuous pressure against the body of the user. In this example, the continuous pressure can secure the UMD at a location and reduce or eliminate movement of the UMD as the user may move around.

In one example, the UMD can include multiple pairs of electrodes to take impedance spectroscopy measurements. A first electrode of an electrode pair can conduct a current to enter the body of a user. A second electrode of the electrode pair can conduct a current to leave the body of the user. The multiple pairs of electrodes can enable the UMD to take multiple impedance spectroscopy measurements using different electrode pairs. An advantage of taking multiple impedance spectroscopy measurements using different electrode pairs can be to take impedance spectroscopy measurements from the user when one or more electrode pairs may not be engaging the body of the user. For example, the UMD can have 4 electrode pairs at different locations on a bottom surface of the UMD. When the UMD engages the body of the user, one or more of the electrode pairs may not properly engage the body of the user. When at least one of the electrode pairs properly engages the body of the user, the UMD can use that electrode pair to take impedance spectroscopy measurements.

In one example, the UMD can be sized and shaped to provide different distances between the first electrode and the second electrode of the electrode pair. In one example, as the distance between the first electrode and the second electrode may be increased or decreased, the amplitude of the current transmitted between the electrode pair can be adjusted. For example, as the distance between the first and second electrode may be decreased, the amplitude of the current between the first and second electrodes may be increased. In another example, as the distance between the first electrode and the second electrode is increased or decreased, a depth that the current may penetrate the body of the user may be adjusted. For example, as the distance between the first and second electrode is increased, the current penetration level between the first and second electrodes may decrease (e.g., the current does not penetrate as far into the body of the user as when the electrodes are closer together).

The electrode pairs of the UMD can be arranged in various arrangements. In one example, the electrodes can be arranged in lines, such as the electrodes where electricity enters the body can be arranged in a first line and the electrodes where the electricity leaves the body can be arranged in a second line. In another example, the electrode pairs can be arranged in a concentric pattern or a circular pattern. In another example, the electrodes can be arranged in a rectangular pattern.

Power management of portable or mobile electronic devices can be used to extend the useful engagement of the devices by reducing the duty cycle of the "on" time period for the device.

The embodiments described herein may address the above-noted deficiency by using user monitoring system to monitor, collect, and/or analyze. The user monitoring system can include a user measurement device (UMD) to monitor, collect, and/or analyze the desired environmental and/or physiological aspects of the user and the user's environment. The UMD can use sensors, stored data, real-time data, received data, and/or algorithms to monitor, collect, and/or analyze environmental and/or physiological information related to an individual, a group of individuals, or a business.

Figure 11:
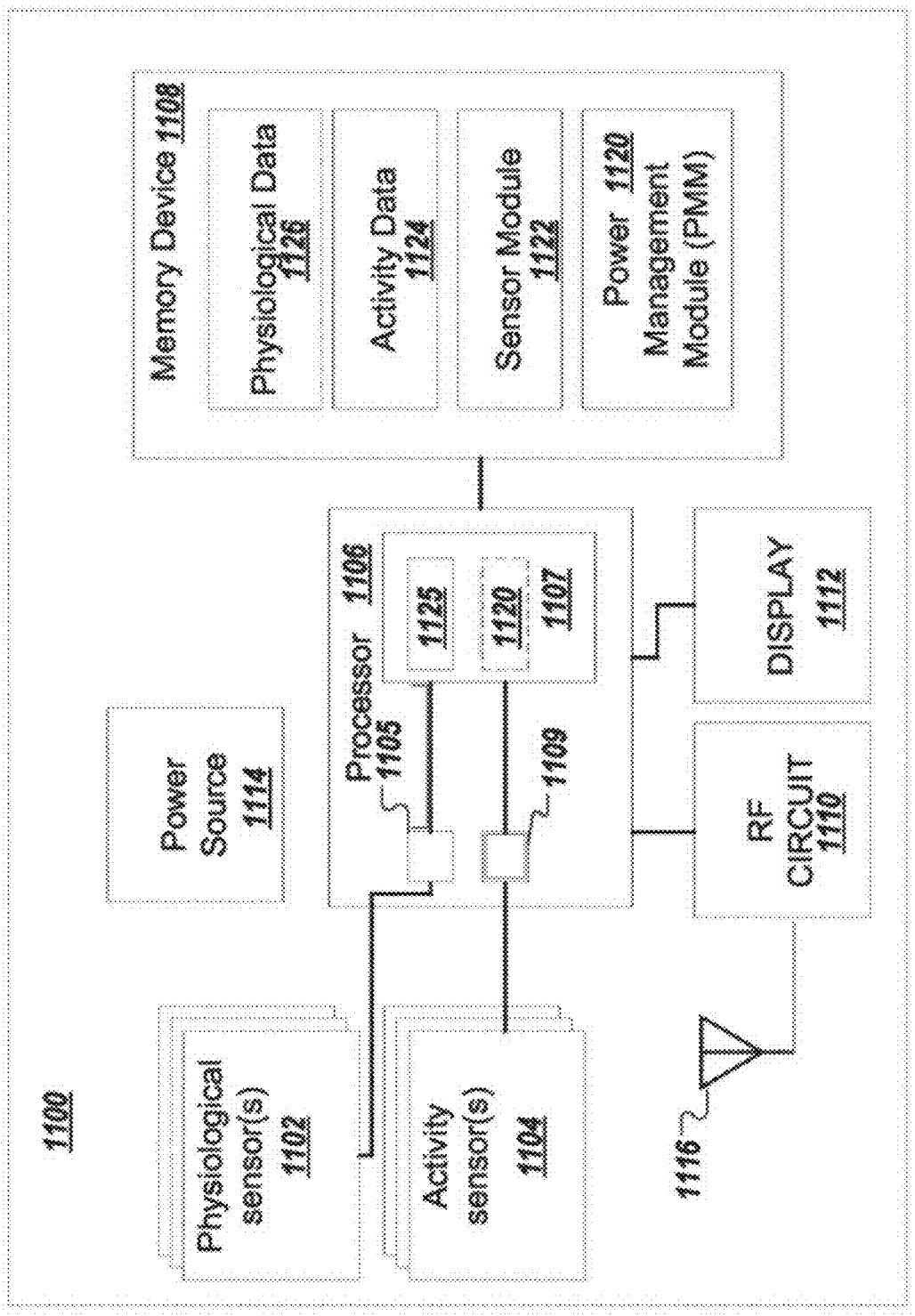
FIG. 11 is a block diagram of a wearable UMD with a power management module according to one embodiment.

FIG. 11 is a block diagram of a wearable UMD 1100 with a power management module 1120 according to one embodiment. The wearable UMD 1100 can include a sensor array with one or more sensors. In the depicted embodiment, the wearable UMD 1100 includes one or more physiological sensors 1102 and one or more activity sensors 1104. In some instances, the activity sensors 1104 may be physiological sensors. That is, in some embodiment, the activity level can be determined from one or more physiological measurements. A physiological measurement may be any measurement related to a living body, such as a human's body or an animal's body. The physiological measurement is a measurement made to assess body functions. Physiological measurements may be very simple, such as the measurement of body or ambient temperature, or they may be more complicated, for example measuring how well the heart is functioning by taking an ECG (electrocardiograph). Physiological measurements may also include motion and/or movement of the body. In some cases, these physiological measurements may be taken to determine an activity level for power management, as described herein. In other instances, separate activity sensors may be used to measure measurements that are specified to activity levels for power management.

The physiological sensors 1102 can include a pulse oximeter sensor, an electrocardiography (ECG) sensor, a fluid level sensor, an oxygen saturation sensor, a body temperature sensor (e.g., a skin temperature sensor), an ambient temperature sensor, a plethysmograph sensor, a respiration sensor, a breath sensor, a cardiac sensor (e.g., a blood pressure sensor, a heart rate sensor, a cardiac stress sensor, or the like), an impedance sensor (e.g., bioimpedance sensor), an optical sensor, a spectrographic sensor, a humidity sensor, an ambient temperature sensor, an altitude sensor, a barometer, a global positioning system (GPS) sensor, a triangulation sensor, a location sensor, a gyroscope sensor, a vibration sensor, an accelerometer sensor, a three dimensional (3D) an accelerometer sensor, a force sensor, a pedometer, a strain gauge, a magnetometer, a geomagnetic field sensor, and the like. The activity sensors 1104 may be any of the physiological sensors described above, but in some cases, the activity sensors 1104 are Newtonian sensors, such as, for example, a gyroscope sensor, a vibration sensor, an accelerometer sensor (e.g., a sensor that measures acceleration and de-acceleration), a three dimensional (3D) accelerometer sensor (e.g., sensor that measure the acceleration and de-acceleration and the direction of such), a force sensor, a pedometer, a strain gauge, a magnetometer, and a geomagnetic field sensor that can be used for activity level measurements; whereas the physiological sensors 1102 may be used for specific physiological measurements.

In another embodiment, the physiological sensors 1102 and activity sensors 1104 can be categorized into physiological sensors, environmental sensors, and Newtonian sensors. The one or more physiological sensors may be a pulse oximeter sensor, an electrocardiography (ECG) sensor, a fluid level sensor, an oxygen saturation sensor, a body temperature sensor, an ambient temperature sensor, a plethysmograph sensor, a respiration sensor, a breath sensor, a cardiac sensor, a heart rate sensor, an impedance sensor, an optical sensor, a spectrographic sensor, or the like. The one or more environmental sensors may be, for example, a humidity sensor, an ambient temperature sensor, an altitude sensor, a barometer, a global positioning system (GPS) sensor, a triangulation sensor, a location sensor, or the like. The one or more Newtonian sensors may be, for example, a gyroscope sensor, a vibration sensor, an accelerometer sensor, a three dimensional (3D) accelerometer sensor, a force sensor, a pedometer, a strain gauge, a magnetometer, a geomagnetic field sensor, or the like. Alternatively, other types of sensors may be used to measure physiological measurements, including measurements to determine activity levels of the wearable UMD for power management. It should be noted that in some cases, power management activities may be performed to reduce the power consumption of the wearable UMD 1100 in response to the determination of the activity level. In other cases, the power management activities may be performed to increase measurement granularity or increase accuracy, precision, or resolution of the measurements by the wearable UMD 1100.

The wearable UMD 1100 includes a processor 1106 having a first sensor interface 1105 coupled to the one or more physiological sensors 1102 and a second sensor interface 1109 coupled to the one or more activity sensors 1104. The processor 1106 includes a processing element that is operable to execute one or more instructions stored in the memory device 1108, which is operatively coupled to the processor 1106. In some cases, the processing element and memory device 1108 may be located on a common substrate or on a same integrated circuit die. Alternatively, the components described herein may be integrated into one or more integrated circuits as would be appreciated by one having the benefit of this disclosure. The memory device 1108 may be any type of memory device, including non-volatile memory, volatile memory, or the like. Although not separately illustrated the memory device may one or more types of memory configured in various types of memory hierarchies. The memory device 1108 may store physiological data 1126, such as current and past physiological measurements, as well as user profile data, bibliographic data, demographic data, or the like. The physiological data 1126 may also include processed data regarding the measurements, such as statistical information regarding the measurements, as well as data derived from the measurements. The memory device 1108 may also store activity data 1124. The activity data 1124 may be current and past measurements, as well as predictive data for predictive modeling of the activity level. In one embodiment, the memory device 1108 may store instructions of the sensor module 1122 and power management module (PMM) 1120, which perform various operations described herein. In particular, the sensor module 1122 can perform operations to control the physiological sensors 1102 and activity sensors 1104, such as when to turn them on and off, when to take a measurement, how many measurements to take, how often to perform measurements, etc. For example, the sensor module 1122 can be programmed to measure a set of physiological measurement according to a default pattern. The default pattern may be the frequency, granularity, and power used for measurements by the physiological sensors. In another embodiment, the PMM 1120 may be implemented as processing logic in the processor 1106. As described herein, the PMM 1120 can determine an activity level based on an activity level (e.g., an activity-based PMM) and can adjust the default pattern in various ways as described in more detail below. For example, the pattern may be adjusted by adjusting a sampling rate; adjusting a number of sensors to take physiological measurements; adjusting a number of different physiological measurements to take; adjusting a frequency or granularity of taking physiological measurements; turning off one or more systems of the apparatus; adjusting a type of communication channel to transmit or receive data; adjusting a frequency at which to transmit or receive data; adjusting a power level to transmit or receive data; adjusting a data rate to transmit or receive data; adjusting a number of different channels to transmit or receive data, or the like.

In the depicted embodiment, the processing element 1107 (e.g., a processor core, a digital signal processor, or the like) executes the instructions of the sensor module 1122 and PMM 1120, as well as possibly other modules, routines. Alternatively, the operations of the sensor module 1122 and PMM 1120 can be integrated into an operating system that is executed by the processor 1106. In one embodiment, the processing element 1107 measures a physiological measurement via the first sensor interface 1105. The processing element 1107 measures an amount of activity of the wearable UMD 1100 via the second sensor interface 1109. The amount of activity could be movement or motion of the wearable UMD 1100, as well as other measurements indicative of the activity level of a user, such as heart rate, body temperature, or the like. The processing element 1107 performs a power adjustment activity in view of the amount of activity. As described above, the physiological measurements may be stored in the memory device 1108 as physiological data and the activity measurements (indicative of the activity level) may be stored in the memory device 1108 as the activity data 1124. When determining the activity level, the processing element (or PMM 1120) may process the activity data 1124 to determine an activity level and the appropriate power adjustment activity, as described herein.

In one embodiment, the PMM 1120 measure a first set of physiological measurements using a first sensor at a first sampling rate. To perform the power adjustment activity when appropriate, the PMM 1120 adjusts the first sampling rate to a second sampling rate in view of the amount of activity and measures measure a second set of physiological measurements using the first sensor at the second sampling rate. In some cases, the second sampling rate is less than the first sampling rate. In other cases, the second sampling rate is greater than the first sampling rate. In another embodiment, the activity-based PMM calculates a rate of change of two or more physiological measurements in a period of time to determine an amount of activity of the wearable UMD.

In another embodiment, a first set of sensors are coupled to the first sensor interface 1105 and a second sensor, designated as an activity sensor, is coupled to the second sensor interface 1109. The PMM 1120 measures a first set of physiological measurements using the first set of sensors. To perform the power adjustment activity, the PMM 1120 determines a subset of less than all of the first set of sensors for a second set of physiological measurements and measures the second set using the subset, instead of the entire first set. In another embodiment, the PMM 1120 turns off at least one of the first set of sensors that is not in the subset to further reduce power consumption by the wearable UMD 1100, for example. In another embodiment, the PMM 1120 adjust a sampling rate of at least one of the first set of sensors that is not in the subset in order to reduce power consumption by the wearable UMD 1100. In another embodiment, the PMM 1120 measures a first set of physiological measurements using a first set of sensors. To perform the power adjustment activity, the PMM 1120 determines a subset of less than all of the first set of sensors based on at least one of an activity type of the user or a selected physiological output and measures a second set of physiological measurements using the subset. In another embodiment, the PMM 1120 measures a first set of physiological measurements using a first set of sensors. To perform the power adjustment activity, the PMM 1120 adjusts at least one of the first set of sensors to a higher granularity to measure a first type of physiological measurements based on at least one of an activity type of the user or a selected physiological output. For example, when the user wants a hydration measurement, the device may only use a certain subset or may adjust a sample rate of one sensor to have higher granularity when measuring hydration.

In another embodiment, the PMM 1120 is able to turn off other components of the wearable UMD 1100, such as an RF circuit Ill 0 used to communicate data via antenna 1116 or display 1112. Alternatively, the PMM 1120 may activate, de-activate, turn on, turn-off, enable, or disable other components of the wearable UMD 1100 according to the measurement pattern defined for the activity level. Alternatively, the PMM 1120 may perform one or more of the power adjustment activities described herein. The wearable UMD 1100 also includes one or more power sources 1114, such as batteries, to supply power to the various components. The power consumed by the wearable UMD 1100 can be adjusted up or down based on the activity level according to some embodiments as described herein.

In one embodiment, the PMM 1120 is considered an activity-based PMM where the activity-based PMM, when executed by the processor 1106, identifies default sample rates at which the sensor module 1125 takes a first set of physiological measurements with multiple sensors (1102, 1104). The activity-based PMM determines an amount of activity of the wearable UMD 1100 based on at least one of the first set of physiological measurements. For example, the first set of physiological measurements may include measurements from the activity sensor(s) 1104 that are primarily used to determine an activity level. The activity-based PMM 1120 may compare the determined activity level against one or more threshold levels to determine an activity level and corresponding power adjustment activity. In one embodiment, the activity-based PMM 1120 determines a second sample rate for at least one of the multiple sensors (1102, 1104) using the determined amount of activity and instructs the sensor module 1125 to adjust the at least one of the multiple sensors to the second sample rate for a second set of physiological measurements. In some cases, the second sample rate is less than the corresponding one of the default sample rates. A lower sampling rate may cause the wearable UMD 1100 to consume less power when taking the second set of physiological measurements than when using the default sample rates to take the first set of physiological measurements. In other cases, the second sample rate is more than the corresponding one of the default sample rates. The higher sampling rate may cause the wearable UMD 1100 to measure the second set of physiological measurements at a higher fidelity than the first set of physiological measurements. It could be higher fidelity, as well as higher accuracy, higher precision, or higher resolution.

In another embodiment, the default sample rates is a first combination of different rates for different ones of the multiple sensors and the activity-based PMM can instruct the sensor module 1122 to adjust the default sample rates to a second combination of different rates for the different ones of the multiple sensors.

In one embodiment, the multiple sensors include a hardware motion sensor to measure at least one of movement or motion of the wearable UMD 1100. The activity-based PMM 1120 can determine the amount of activity based at least in part on the at least one of the movement or motion of the wearable UMD 110. The hardware motion sensor may be an accelerometer sensor, a gyroscope sensor, a magnetometer, a GPS sensor, a location sensor, a vibration sensor, a 3D accelerometer sensor, a force sensor, a pedometer, a strain gauge, a magnetometer, and a geomagnetic field sensor. The multiple sensors may be from the following types of sensors: a physiological sensor, an environmental sensor, and a Newtonian sensor. The hardware motion sensor may be considered the activity sensor and other sensors may be used for physiological measurements, such as one or more of the following types of sensors: a pulse oximeter sensor, an ECG sensor, a fluid level sensor, an oxygen saturation sensor, a body temperature sensor, an ambient temperature sensor, a plethysmograph sensor, a respiration sensor, a breath sensor, a cardiac sensor, a heart rate sensor, an impedance sensor, an optical sensor, a spectrographic sensor, a humidity sensor, an ambient temperature sensor, an altitude sensor, a barometer, a GPS sensor, a triangulation sensor, a location sensor, a gyroscope sensor, a vibration sensor, an accelerometer sensor, a three dimensional (3D) accelerometer sensor, a force sensor, a pedometer, a strain gauge, a magnetometer, and a geomagnetic field sensor. In other embodiments, the measurements may be any one or more of the following types of measurements: a hydration level measurement, a heart rate measurement, a blood pressure measurement, an oxygen level measurement, and a temperature measurement. In some cases, a sensor may be used to take a temperature measurement at an inner ear region, such as in connection with a headphone that can be placed in an ear cavity. Alternatively, other types of measurements can be taken.

In another embodiment, a first sensor of multiple sensors in the UMD 110 can take a first set of physiological measurements at a first sampling rate. The activity-based PMM calculates a rate of change of at least two of the first set of physiological measurements measured in a period of time and instructs the sensor module 1122 to adjust the first sensor to a second sampling rate for a second set of physiological measurements in view of the rate of change. In a further embodiment, the activity-based PMM 1120 calculates a second rate of change of at least more of the first set of physiological measurements measured in the period of time and instructs the sensor module 1122 to adjust the first sensor to the second sampling rate for the second set of physiological measurements in view of the rate of change and the second rate of change. In some cases, the rate of change may be indicative of an amount of activity of the wearable UMD 110. In other cases, the amount of activity can be defined using the rate of change, as well as other physiological measurements or calculations made using the physiological measurements, like the rate of change.

Although the embodiment illustrated in FIG. 11 illustrates and describes the power management being managed by the PMM 1120 as executable instructions by the processor 1106, in other embodiments, the power management operations may be performed may be performed in a power management system comprising hardware (circuitry, dedicated logic, etc.), software (such as is run on a general purpose computing system or a dedicated machine), firmware (embedded software), or any combination thereof. In some embodiments, a separate controller could be coupled to the processor 1106 and the controller includes circuitry and/or instructions or microinstructions to perform the power management operations described herein.

In another embodiment, a portable electronic device (e.g., wearable UMD 1100) includes one or more sensors to integrated or coupled to the portable electronic device. In one example, the portable electronic device or a power management system of the portable electronic device can use the one or more sensors to manage power consumption of the portable electronic device. In one example, the portable electronic device may include an activity sensor, such as an accelerometer, a gyroscope, a 3D accelerometer, and so forth. In one example, the power management system can adjust an amount of power consumed by the portable electronic device in view of an amount of activity detected or measured by the activity sensor. In one example, the portable electronic device can be a wearable device, such as a wristband or a fitness band. In this example, the wearable device can use the activity sensor to measure an amount of activity (such as movement or motion) of the wearable device and communicate the amount of activity of the wearable device to the power management system. The power management system can adjust an amount of power used by the wearable device in view of the amount of activity measured by the activity sensor. For example, when the power management system determines that an activity rate of the user is relatively low (such as the user sitting down or resting), the power management system can reduce a sample rate duty cycle to provide a low power "sleep mode" during the lower activity level periods. An advantage of adjusting the sample rate duty cycle based on an activity level of the user can be to reduce a power consumption of the device during lower activity periods while maintaining high fidelity measurements during periods of relatively high activity.

In one example, the wearable device can include multiple sensors used to take different measurements, such as a heart rate sensor, a bio-impedance sensor, an optical sensor, a skin temperature sensor, an ambient temperature sensor, a humidity sensor, a global position system (GPS) sensor, a pulse oximeter sensor, an accelerometer, a 3D accelerometer, a gyroscope, and so forth. The wearable device can use the multiple sensors to make one or more measurements, such as a hydration level measurement, a heart rate measurement, a blood pressure measurement, an oxygen level measurement, a temperature measurement (skin temperature and/or ambient temperature). In one example, the power management system can use the activity sensor to measure an activity level of the user and perform a power adjustment activity in view of the measured activity level.

In one example, the power adjustment activities can include: adjusting a number of sensors used to take the different measurements, adjusting a number of different measurements to take, adjusting a frequency or granularity of one or more measurements (e.g. how often one or more measurements are taken), turning on or off one or more systems of the wearable device (such as a display or communications system), and so forth. The portable device (such as a wearable device) can include a communication module to transceive data (e.g., send and receive data). In another example, the power adjustment activities can include: adjusting a type of communication channel used to transceive data, such as via the Bluetooth®, Wi-Fi®, cellular technologies and so forth; a frequency in time or rate that the portable device sends or receives data; an amount of power used to send or receive data, such as adjusting a broadcast power used, an amount of power used to receive a signal, a data rate that data can be sent or received; a number of different channels or communication types the portable device may use, such as dual-band or multi-band communications; and so forth.

In one example, when the wearable device uses the activity sensor to determine that an activity level of the user of the wearable device is below a threshold level (such as when the user is resting or sitting down), the wearable device can reduce a frequency of the number of times the wearable device take measurements using the one or more sensors of the wearable device. In another example, when the wearable device uses the activity sensor to determine that an activity level of the user of the wearable device exceeds a threshold level (such as when the user exercising or moving), the wearable device can increase a frequency of the number of times the wearable device take measurements using the one or more sensors of the wearable device. An advantage of the power management system performing a power adjustment activity in view of the measured activity level can be to adjust a measurement granularity in view of the activity of the user of the wearable device. For example, when a user is inactive (e.g. the activity level of the user is below a threshold level) then a rate of change in the one or more measurements taken by the wearable device is lower relative to when the user is active (e.g. the activity level of the user exceeds a threshold level). In this example, the power management system can preserve power by reducing the frequency of the number of times the wearable device take measurements when the user is inactive without reducing or substantially reducing a quality of the measurements because the lower rate of change in the measurements. Alternatively, the power management system can increase the power consumption of the wearable device to maintain a quality of the measurements by increasing the frequency of the number of times the wearable device take measurements when the user is active.

The power management system can use a predictive algorithm to when a probability of an activity level of a user changing exceeds a threshold level (e.g., predict a transition for a current activity level to a new activity level). In one example, the predictive algorithm can be a regression algorithm such as a linear regression model, a discrete choice model, a logistic regression model, a multinomial logistic regression model, a probit regression model, a time series model, and so forth. In another example, the predictive algorithm can be a machine learning technique such as neural network, a multilayer perceptron (MLP), a radial basis function, a support vector machine, a Naive Bayes, a geospatial predictive model, and so forth.

In one example, the power management system can use the predictive algorithm to determine when an activity level of a user may transition from a relatively high activity level to a relatively low activity level. For example, the power management system can use the predictive algorithm to determine when a user may finish a labor-intensive task (such as a labor-intensive job) and return home to relax. In one example, the predictive algorithm can use data from the GPS sensor or triangulation sensor to predict a transition from the relatively high activity level to the relatively low activity level. For example, the GPS sensor or triangulation data can indicate that a user may be moving from a work location to a home location and the predictive algorithm can determine that the user may be transitioning from the relatively high activity level to the relatively low activity level based on the change in location. In another example, the predictive algorithm can use scheduling information (such as a schedule of the user received from an input device) or a time of day to determine a transition in the activity level. In another example, the power management system can store previous activity information and analyze the previous activity information to predict patterns or trends in the previous activity information. The predictive algorithm can forecast or predict a transition in activity level based on the predicted patterns or trends in the previous activity information. For example, the power management system can use the predictive algorithm to determine that, based on a trend in the previous activity information, a user has a 90 percent probability of going to a gym after work at 7 PM on Wednesdays before going home. In this example, the power management system can transition to a high activity level while the user is at the gym and then transition to a low activity level when the user leaves the gym to go home.

In another example, the power management system can use the predictive algorithm to determine when a user may switch from sleeping to awake. When the power management system predicts a transition for a current activity level to a new activity level, the power management system can adjust a sample rate duty cycle or measurement granularity. For example, when the power management system predicts a transition for a high activity level to a low activity level, the power management system can reduce the sample rate duty cycle or the measurement granularity. In another example, when the power management system predicts a transition for a low activity level to a high activity level, the power management system can increase the sample rate duty cycle or the measurement granularity. An advantage of the power management system using the predictive algorithm to determine a transition or change in activity level can be to reduce or eliminate using background monitoring (e.g., a full sleep mode) of an activity level to determine when to adjust the sample rate duty cycle or the measurement granularity. The predictive algorithms can also be used to adjust a length of the sleep mode. For example, when the device is in sleep mode, the device may only check every 5 minutes to see if it should wake up. This can be problematic when that 5 minutes of data may be desirable to be captured or to avoid the user having to wait minutes before the device may respond to user input. Using the predictive algorithm, the device can shorten or lengthen a frequency at which the device checks if it should wake up. When the background monitoring is reduced or eliminated, a power consumption of the portable device can be reduced because the portable device may not periodically use sensors for background monitoring.

In another example, the portable device can monitor one or more measurement to determine a change or a rate of change of measurement data or data. In one example, the power management system can perform a power adjustment activity in view of the change or a rate of change of the measurement data or data. In one example, the portable device can take a measurement using a sensor of the portable device and store previous measurement data in a memory of the portable device. In one example, the portable device can compare the current measurement data to previous measurement data to determine an amount of change between the current measurement data and the previous measurement data. In another example, the portable device can compare the current measurement data to previous measurement data to determine a rate of change between the current measurement data and the previous measurement data. In another example, when the amount of change or the rate of change of the measurement data is below a threshold value, the power management system can perform a power adjustment activity to reduce a power consumption level of the portable device. In another example, when the amount of change or the rate of change of the measurement data exceeds a threshold value or score, the power management system can perform a power adjustment activity to increase the sample rate (power consumption level) of the portable device to maintain a measurement granularity.

In another example, the power management system can perform a power adjustment activity in view of time, such as the time of day, day of the week, week of the month, or month of the year. In one example, the power management system can select a first measurement or data granularity threshold for the portable device during a first selected period of time and a second measurement or data granularity threshold for the portable device during a second selected period of time. For example, the portable device can be a portable device with multiple sensors (e.g. a sensor array) to take selected measurement. In this example, a user of the portable device may desire to have a higher measurement or data granularity threshold during a period when the user is exercising or working out (such as in the evening between 6 pm to 9 pm) and a lower measurement or data granularity threshold (relative to the higher measurement or data granularity threshold) when the user is not working out (such as when the user is eating, working, or sleeping). In one example, the portable device can use predefined schedule information of the user (such as a predefined daily routine of the user). In another example, the portable device can communicate with another device (such as a smartphone or computer) to receive schedule information example (such as an electronic calendar or appointment information) to determine when the user may desire to have a measurement or data granularity thresholds for different periods of time. In another example, the portable device can use a smart algorithm to track daily, weekly, and/or monthly activities of the user. In this example, the portable device can iteratively update an activity log of the user based on current and/or recent activity information. The portable device can use the information stored in the activity log to determine when the user may desire to have a measurement or data granularity thresholds for different periods of time In another example, the portable device can measure a hydration level of the user. In one example, during a first period of time, the user may typically or habitually be outside where a temperature is higher or a humidity level is higher and during a second period of time the user may be in an air-conditioned indoor location where the temperature is lower or the humidity is lower than the outdoor location. In this example, a hydration level measurement or data granularity threshold may be higher during a scheduled or typical period when the user is outdoors and the hydration level measurement or data granularity threshold may be lower (relative to the outdoor threshold) during a scheduled or typical period when the user is indoors.

In another example, the portable device can measure stress to the physiological or physical body of the user. Similarly, the user may be indoors during winter months of the year for longer periods of time (the portable device using a lower measurement or data granularity threshold) and outdoors during summer months of the year for longer periods of time (the portable device using a higher measurement or data granularity threshold). In one example, during a first period of time, the user may typically or habitually be at a lower stress level (such as when the individual is sleeping) and during a second period of time the user may be at a higher stress level relative to the lower stress level (such as when the user first awakes in the morning or when the individual is working out). In this example, a stress level measurement or data granularity threshold may be lower during a scheduled or typical low-stress period and the stress level measurement or data granularity threshold may be higher (relative to the low-stress period) during a scheduled or typical period when the user is more stressed.

In another example, the power management system can perform a power adjustment activity in view of the location of the user or the portable device. In one example, the portable device can determine the location of the user or the portable device using a global positioning system (GPS) sensor or a triangulation system (such as a wireless fidelity or cellular triangulation system). In one example, the power management system can select or set a first power consumption threshold and/or measurement or data granularity threshold for a first location and a second power consumption threshold and/or measurement or data granularity threshold for a second location. For example, the first location can be a location of a fitness facility and the second location can be a home location of the user. In this example, when the portable device determines that the user is at the home location, the power management system can decrease the power consumption threshold and/or measurement or data granularity. Additionally, when the portable device determines that the user is at the fitness facility location, the power management system can increase the power consumption threshold and/or measurement or data granularity.

In one example, the portable device can determine the location of the user or the portable device using an altimeter. In one example, the power management system can select or set a first power consumption threshold and/or measurement or data granularity threshold for a first altitude and a second power consumption threshold and/or measurement or data granularity threshold for a second altitude. For example, the first altitude can be at an altitude above 1000 feet above sea level and the second altitude can be at an altitude between 0 and 999 feet above sea level. In this example, when the portable device determines that the user is at the first altitude, the power management system can increase the power consumption level and/or measurement or data granularity as the physical system of the user may be at a higher stress level or at a higher dehydration rate. Additionally, when the portable device determines that the user is at the second altitude, the power management system can decrease the power consumption level and/or measurement or data granularity as the physical system of the user may be at a lower stress level or at a lower dehydration rate.

In one example, the portable device can determine when the portable device may be in proximity or within a threshold distance of one or more other portable devices. The portable device can use a beacon signal or a heartbeat signal via a communication network (such as networks using the Bluetooth®, RFID, or Zigbee® technologies) to determine when another portable device may be in proximity or within a threshold distance In this example, when the portable device may be in proximity or within a threshold distance of one or more other portable devices, the power management system may determine that the user may be located at an area where the user may physically exert himself or herself (such as a gym, playing field, bicycle path, and so forth). The power management system may increase the power consumption threshold and/or measurement or data granularity based on the one or more other portable devices being in proximity or within the threshold distance.

In another example, the power management system may increase the power consumption threshold and/or measurement or data granularity when a threshold level of other portable devices may be in proximity or within the threshold distance. For example, the threshold level can be set to the proximity of 3 other devices. In this example, when one or two other devices may be in proximity or within the threshold distance, the power management system may maintain a current power consumption threshold and/or measurement or data granularity. When 3 or more other devices may be in proximity or within the threshold distance, the power management system may increase a current power consumption threshold and/or measurement or data granularity. An advantage of using a proximity or threshold distance of other devices when determining when to adjust a current power consumption threshold and/or measurement or data granularity can be to a low power consumption determination. For example, determining a location of the portable device using GPS can be higher in power consumption than using a personal area network (e.g., Bluetooth® technology). Determining the location from the PAN may consume a relatively lower amount of power. Another advantage of using a proximity or threshold distance of other devices when determining when to adjust a current power consumption threshold and/or measurement or data granularity can be when the portable device may be located in a building or other location where GPS or triangulation may not be available.

In another example, the power management system can perform a power adjustment activity in view of manual user settings. The manual user setting can include: a selected battery usage life (e.g. how long the user desires the battery of the portable device to last); a measurement or data granularity, a display brightness level, a power source recharge rate (e.g. how often the portable device is recharged); a data communication frequency level (e.g. how frequently the portable device communicates data to another device); a communication network type (e.g. whether the portable device uses a cellular network, a wireless local area network (WLAN) (e.g., network using the Wi-Fi® technology), a PAN (e.g., Bluetooth® or Zigbee® technologies); one or more type of measurements the portable device can take using one or more sensors or the portable device; one or more types of sensors the portable device can use to make one or more measurements; a type or frequency of a sensory alert from the portable device (e.g. a vibration alert, a visual alert, an auditory alert; and so forth. In one example, a user of the portable management system can select or adjust one or more of the manual user settings to adjust a power consumption rate and/or a measurement or data granularity of the portable device.

In one example, the portable device can receive the manual user setting from another device (such as a USB connection or a PAN connection with a computing device). In another example, the portable device can receive the manual user setting from a graphical user interface (such as via a touch screen integrated into the portable device). In one example, the graphic user interface an display an power usage level, power consumption rate, an approximated usage time period remaining for the portable device, and/or a measurement or data granularity level in view of different manual user settings. For example, the portable device can have an approximate usage period of two days when the portable device is initially be set to a data measurement frequency of once every minute, a display brightness of 2 lumens, and a have 2 sensors selected to take measurements. In this example, the user of the portable device can adjust the manual settings of the portable device to a data measurement frequency of once every 10 minutes, a display brightness of 1 lumen, and a have 1 sensor selected to take measurements to increase the usage period of the portable device to 4 days. In another example, the portable device can have presets or predefined settings that a user can select to adjust the power consumption threshold and/or measurement or data granularity. In another example, the portable device can have a series of selectable configurations that a user can select (via an input device) to adjust the power consumption threshold and/or measurement or data granularity.

In one example, the power source of the portable device can be a battery power source, a solar power source, a kinetic or motion power source, an induction power source, a wired or physical contact power source, and so forth.

In another example, the power management system can perform a power adjustment activity in view of a user profile or demographic information of a user. In one example, the user profile or demographic information of the user can comprise of: an age of the user; a gender of the user; a physical weight of the user; a body mass of the user; a health level of the user (such as if the user has any diseases, chronic conditions, is currently sick, and so forth); a body fat percentage of the individual; a health risk level of the individual (such as if the user smokes cigarettes, drinks alcohol, is pregnant); a race of the individual; a fitness level or activity level of the user (e.g. how often and for how long does the individual exercise); and so forth.

In one example, when the physical weight of a user is lower than a threshold physical weight (for example 140 pounds) then the number of measurements taken by the portable device is set at a first number of measurements for a given time period and when the physical weight of a user is higher than the threshold physical weight then the number of measurements taken by the portable device is set at a second number of measurements for the time period. In one example, the first number of measurements for the time period is greater than the second number of measurements for the time period. For example, when a hydration level female that weighs 100 pounds (lbs.) decreases by 5% the effects of the hydration level decrease may be larger than a 5% hydration level decrease for a female that weighs 300 pounds. In this example, where the effects of the hydration level are greater for the female that weighs 100 lbs. the portable device can increase the number of measurements taken for the period (increasing the power consumption level) to provide the female with a greater measurement granularity level (such as a sample rate) to offset the increased sensitivity to a hydration level change.

The power management system can adjust a power consumption level and/or adjust the measurement granularity level differently for different sensors of the sensor array, e.g., different sensors have different power consumption or measurement granularity priorities or weights. In one example, the power management system assigns a first weight to a first sensor of a sensor array (such as a bio-impedance sensor) and a second weight to a second sensor of the sensor array (such as a heart rate sensor). When the first sensor takes measurements, the power management system can increase the power consumption level and/or increase the measurement granularity level. When the second sensor takes measurements, the power management system can decrease the power consumption level and/or decrease the measurement granularity level.

In another example, the measurement granularity level (which correlates with the power consumption level) can be adjusted in view of the fitness level of the individual using the portable device. For example, when the fitness level of a user is high (e.g. a marathon runner or professional athlete) then the measurement granularity level can be decreased as the rate of change in measurements taken by portable device can be lower than a rate of change in measurements taken by portable device when the user has a low fitness level (e.g. an individual that works out once a week). In this example, because the body of the user with a high fitness level has acclimated to a higher level of physical exertion before the rate of change in measurements shows a threshold rate of change, the number of measurement granularity level can be decreased compared to the user with a lower fitness level.

In one example, the power management system can adjust a power consumption level of the portable device in view of a health level of the individual. For example, the portable device can monitor an oxygen consumption level of a user to determine that the user is sick. When the user is sick the portable device can increase a sensor measurement granularity to capture more measurement details while the user is sick.

In another example, the power management system can perform a power adjustment activity in view of multiple user profile or demographic information of a user. For example, the power management system can select of first measurement granularity level for a user that is 20, a female, has a high fitness level, weighs 100 lbs., and is healthy. In this example, the power management system can select of a second measurement granularity level for a user that is 50, a male, has a low fitness level, weighs 250 lbs., and is unhealthy. In one example, the first measurement granularity level can be lower than the second measurement granularity level.

In another example, the power management system can perform a power adjustment activity in view of a type of activity the portable device is used for. In one example, the type of activity can be a sports or athletic activity, such as running, football, basketball, soccer, baseball, hockey, and so forth. In another example, the type of activity can be a type of work of the user, such as an office work environment, a police officer work environment, a construction worker work environment, a military or soldier work environment, and so forth. In one example, the power management system can perform a power adjustment activity, such as adjusting a measurement granularity level, in view of the type of activity. For example, when the portable device is used for football, the measurement granularity level can be adjusted to a first measurement granularity level and when the when the portable device is used for baseball, the measurement granularity level can be adjusted to a second measurement granularity level. In another example, when the portable device is used by an individual in an office work environment the measurement granularity level can be adjusted to a third measurement granularity level and when the portable device is used by an individual in a military or soldier work environment the measurement granularity level can be adjusted to a fourth measurement granularity level.

In another example, the power management system can perform a power adjustment activity in view of a calibration level of the portable device or one or more sensors of the portable device. In one example, when the calibration level of the portable device is below a threshold value an amount of power provided to a sensor of the portable device can be increased to provide a high amplitude to the sensor to enable a higher power measurement. In another example, when the calibration level of the portable device is below a threshold value a measurement granularity level can be increased to enable more measurements to be taken by the sensor to provide more data points to counterbalance for a lower calibration level. In another example, when the calibration level of the portable device exceeds a threshold value, an amount of power provided to a sensor of the portable device can be decreased to provide a lower amplitude to the sensor to enable a power consumption saving.

In another example, the power management system can perform a power adjustment activity in view of an amount of power remaining for the power source of the portable device. For example, when the power source of the portable device has a remaining power level that exceeds a threshold amount, amplitude and or measurement granularity level of one or more sensors of the portable device can be at a first threshold power consumption level. In this example, when the power source of the portable device decreases below a threshold remaining power level, an amplitude and or measurement granularity level of one or more sensors of the portable device can be switched to a second threshold power consumption level. In another example, the power management system may use be a multiple threshold power consumption levels to increase an adjustability of the power consumption levels. In another example, the power management system may use a power consumption level ratio or an adjustment value to continuously adjust the power consumption level based on the amount of power remaining. In another example, the power management system can perform a power adjustment activity automatically (such as reducing a sample rate of one or more sensors) when the amount of power remaining or the state of charge decreases below a threshold level.

In another example, the power management system can perform a power adjustment activity in view of a health level of the power source of the portable device, such as a battery health level. As a battery ages, an amount of power that the battery can store can decrease, e.g. an amount of time between when the battery needs to be recharged decreases. In one example, when the health level of the battery progressively decreases to different battery health levels, the power management system can adjust a power consumption level of the portable device to maintain an approximate same usable period between recharging of the portable device. In another example, the power management system can adjust a power consumption level of the portable device in view of a state of charge (e.g., a remaining amount of power) and a battery health level. The power management system can determine a capacity of the battery and expected duration the battery can provide power based on state of charge and the power management system. The power management system can adjust a power consumption level (such as a duty cycle) based on an expected duration the battery can provide power until a next recharging.

In one example, when the portable device has new (e.g. hasn't been used) a battery of the portable device can have a 100% battery health level and the portable device can have a first power consumption level that enables the portable device to have a usage period of time, such as 24 hours. In this example, when the portable device has been used for a period of time, such as for 1 year, the battery health can decrease to 50% battery health. When the battery health decreases to 50% the power management system can adjust a power consumption level of the portable device (such as a measurement granularity level or power amplitude of a sensor) to a second power consumption level to enable the portable device to maintain the usage period of time. In another example, the health of the battery can be determined based on a remaining capacity of the battery cells. As a number of times a battery has been charged and discharged increases, the remaining capacity of the cells can decrease (such as for a lithium-ion battery). In this example, the portable device battery health can be associated with a number of charge and discharge cycles of the battery.

In one example, the power management system can perform a power adjustment activity in view of a type of communication network the portable device is using to communicate data. In one example, the communications network can be a cellular network. The cellular network can be configured to operate based on a cellular standard, such as the third generation partnership projection (3GPP) long-term evolution (LTE) Rel. 8, 9, 10, 11, or 12 standard, or the Institute of Electronic and Electrical Engineers (IEEE) 802.16p, 802.16n, 802.16m—2011, 802.16h—2010, 802.16j—2009, or 802.16 —2009 standard.

In another example, the communications network can be a wireless local area network (such as the Wi-Fi® technology) that can be configured to operate using a standard such as the IEEE 802.11 —2012, IEEE 802.11ac, or IEEE 802.11ad standard. In another example, the communications network can be configured to operate using the Bluetooth® standard such as Bluetooth® v1.0, Bluetooth® v2.0, Bluetooth® v3.0, or Bluetooth® v4.0. In another example, the communications network can be configured to operate using the ZigBee® standard, such as the IEEE 802.15.4 —2003 (ZigBee® 2003), IEEE 802.15.4 —2006 (ZigBee® 2006), or IEEE 802.15.4 —2007 (ZigBee® Pro) standard.

In one example, when the portable device uses a cellular network to communicate data the power management system can adjust a power consumption level to a first power consumption level and when the portable device uses a wireless local area network (WLAN) to communicate data the power management system can adjust a power consumption level to a second power consumption level. In this example, for the portable device to communicate data over a cellular network, the portable device may consume more power than when the portable device communicates data using the WLAN. Accordingly, when the portable device communicates data using the cellular network the power management system can provide an increased amount of power to enable the portable device to communicate the data. In another example, when the portable device determines that the data is communicated using the cellular network, the portable device can adjust a measurement granularity level. For example, when communicating the data may use an increased amount of power, the portable device can decrease the number of measurements taken for a period of time (i.e. decreasing an amount of data to communicate) to adjust for the increased power consumption when using the cellular network.

In one example, the power management system can use a non-communication setting to turn off the communications or data transfer by the portable device (e.g., an airplane mode). In this example, the communications and data transfer of the portable device can be turned off to conserve power.

In one example, a user or a third party (i.e. an individual that is not a user of the portable device) can adjust one or more settings of the power management system. In one example, the user can be an athlete on a professional sports team and the 3rd party can be a trainer of the athlete. In this example, the trainer of the athlete can adjust a setting of the power management system, such as a measurement granularity level, when the athlete is training with the trainer. When the athlete has completed training with the trainer, the setting of the power management system can return to an initial setting, the setting remains at the settings selected by the trainer, or the athlete can select a new setting. In another example, the user can be a medical patient and the 3rd party can be a medical professional, such as a doctor monitoring the patient. In one example, the doctor can adjust different sensors of the portable device in view of a medical diagnosis or symptoms of the patient. For example, the doctor can increase an amount of power and measurement granularity for a heart rate sensor or a blood pressure sensor and decrease an amount of power to other sensors of the portable device (such as put the sensors in sleep mode or turn the sensors off) when the patient is being monitored for a heart condition (such as a heart attack).

In another example, a user can use multiple portable devices at the same time or substantially the same time. For example, the portable device can be a monitoring device that can be coupled to different locations of the body of the user. In one example, the multiple portable devices can communicate with each other. In one example, the power management system can adjust the power consumption level of one or more of the portable device in view of the number of devices being used at the same time. For example, when a user is using five different portable devices at different locations on the body of the user, the power management system can decrease the power consumption level of each portable device compared to a power consumption level when only one portable device is used. In this example, the power management system can decrease the power consumption level of each portable device because the granularity of the overall measurement data can increase as the number of portable devices being used by the user increases.

In another example, the power management system can adjust the power consumption level of each of the multiple devices to different power consumption levels based on device criteria. In one example, the device criteria can include: a battery capacity level, a type of measurement the device is taking, a battery power remaining level, an approximate usage period of the device, and so forth. In this example, each of the multiple devices can have different device criteria. For example, a first portable device can have a battery power remaining level of 30 minutes and a second portable device can have a battery power remaining level of 24 hours. In this example, the power management system can decrease a power consumption level of the first portable device and increase a power consumption level of the second portable device to maintain an overall measurement granularity level while extending the battery power remaining period of the first portable device.

In one example, the portable device can include a swappable battery pack. In one example, the portable device can be a wearable wristband to measure hydration. In this example, when a power remaining level of the portable device decreases below a threshold level, the portable device can indicate to the user to switch a first battery that is depleted with a second battery that is fully charged. In another example, the portable device can have an internal battery to provide power to the wearable wristband while the first battery is switched with the second battery.

In one example, the portable device can alert the user to recharge a power source of the portable device or switch the power source of the portable device when a power remaining level of the current power source of the device decreases below a threshold level. In another example, when the remaining power level decreases below a threshold level, the portable device can provide the user with a different power consumption options. In one example, the power consumption options can include: a power off mode, where the device is turned off; a heartbeat mode, where the device runs on minimal power and wakes up to take measurements at selected periods of time or at selected events; a minimum power mode, where the portable device can continue to monitor the user but turn on one or more options on the portable device (such as a display screen, a speaker) and/or reduce the measurement granularity of the sensor measurements; a full power mode, where the portable device will continue to operate at full power until the power source is fully depleted. In another example, the portable device can operate in different modes in view of the remaining power level. For example, when the remaining power level is between 40% and 100% the portable device can function in full power mode, when the remaining power level is between 20% and 39% the portable device can operate in minimum power mode, and when the remaining power level is between 1% and 19% the portable device can operate in heartbeat mode. This example is not intended to be limiting and the remaining power levels and modes can vary. In one example, the modes can be predetermined for the remaining power levels. In one example, the portable device can have an override mode, where the user can select to continue to operate in a first mode when the portable device reaches a remaining power level that the portable device would normally switch at. In another example, a user can select different modes and/or remaining power levels using an input device such as a GUI.

In another example, the portable device can determine a power consumption rates based on an amount different systems and sensors of the portable device may consume for different settings. In one example, the portable device can display to the user different operating time and/or different system and sensor settings and a user can select an operating time and/or different system and sensor settings in view of the power consumption rate of the portable device.

In another example, the power management system or the portable device can increase or decrease a number of sensors of the portable device taking the measurement and/or the frequency that one or more of the sensors is taking measurements. For example, if a first sensor (such as an impedance spectroscopy sensor) consumes a power at a first rate and a second sensor (such as a heart rate monitor) consumes power at a second rate that is lower than the first rate, when the remaining power level of the power management system decrease below a threshold level, the power management system can adjust the first sensor and/or the second sensor. In one example, the power management system can turn off the first sensor. In another example, the power management system can decrease a measurement granularity of the first sensor. In another example, the power management system can turn off the second sensor. In another example, the power management system can decrease a measurement granularity of the second sensor.

In another example, the power management system or the portable device can adjust one or more sensors in view of a rate of change in the measurements of the one or more sensors. For example, if a rate of change in measurements of a first sensor (such as an impedance spectroscopy sensor) is at a first rate and a rate of change in measurements of a second sensor (such as a heart rate monitor) is at a first rate, the power management system can adjust one or more settings of the first sensor and/or the second sensor. For example, when the first rate of the first sensor is below a threshold value (such as nearly stagnant), then the power management system may decrease a measurement granularity of the first sensor. In another example, when the second rate of change in measurements of the second sensor is above a threshold value (such as nearly stagnant), then the power management system may increase a measurement granularity of the second sensor. In another example, the power management system can adjust a power consumption mode of the portable device in view of the first rate and/or the second rate. In one example, when the first rate and/or the second rate is below a threshold value the power management system can switch the portable device to a heartbeat mode to conserve power. In another example, when the first rate and/or the second rate is above a threshold value the power management system can switch the portable device to a full power mode to capture a finer detail level for the measurements of the first sensor and/or the second sensor.

In one example, the portable device can communicate with other devices, such as other measurement devices. The other measurement device can include: a heart rate monitor, a pulse oximeter sensor, a body weight measurement scale, a sleep tracker, a glucose meter, and so forth. In one example, the portable device can determine when the other device can take the same or similar measurements to the sensors attached to the portable device. When the other devices can take the same or similar measurements to the sensors attached to the portable device, the power management system can decrease the measurement granularity of that sensor of the portable device or turn the sensor of the portable device off. For example, the portable device can have a heart rate sensor and a chest strap can also have a heart rate sensor. In this example, the portable device can communicate with the chest strap to receive measurements from the chest strap and turn off the heart rate sensor of the portable device.

In another example, the portable device can include one or more environmental sensors, such as an ambient temperature sensor, a humidity sensor, a weather sensor, an altitude sensor, a barometer, and so forth. In one example, the portable device can use one or more of the environmental sensors to adjust one or more settings of the physiological sensors of the portable device. For example, the portable device can use the humidity sensor to detect when the humidity level of the location where the user is located increases above a threshold humidity level. When the humidity level increase above the threshold, the portable device can increase a measurement granularity of one or more of the sensor to provide a more detailed measurement scope. In another example, when an ambient temperature sensor determines that the temperature decreases below a threshold temperature, the power management system can decrease a measurement granularity of one or more sensors of the portable device to conserve power as a rate of change in the measurements of the sensors may decrease as the temperature decreases (such as when the temperature decrease a rate of change of hydration measurements may also decrease). In one example, the environmental sensors can be attached to the portable device or integrated into the portable device. In another example, the environmental sensors can be at different locations, such as an environmental monitoring station that communicates with the portable device. In another example, the portable device can receive environmental information from another source, such as a weather monitoring website or an application on a smartphone in communication with the portable device.

The portable device can include a processor to execute computer programs or applications. In one example, the power management system can use the algorithms, techniques, and/or methods discussed in the proceeding paragraphs to adjust power consumption activities based on applications that may be running on the portable device. For example, when the portable device is running an application that may consume power at a consumption level, the power management system may adjust a display of the portable device, a processing speed of the portable device, and so forth. In another example, the portable device can perform power consumption adjustment activities, such as adjusting a power consumption level or measurement granularity level, for one or more sensors based on an application running or executing on the portable device. For example, when the portable device is running an application that may consume a relatively large amount of power (such as an application with heavy computational or processing requirements) the power management system can perform power consumption adjustment activities to reduce power consumption.

Figure 12:
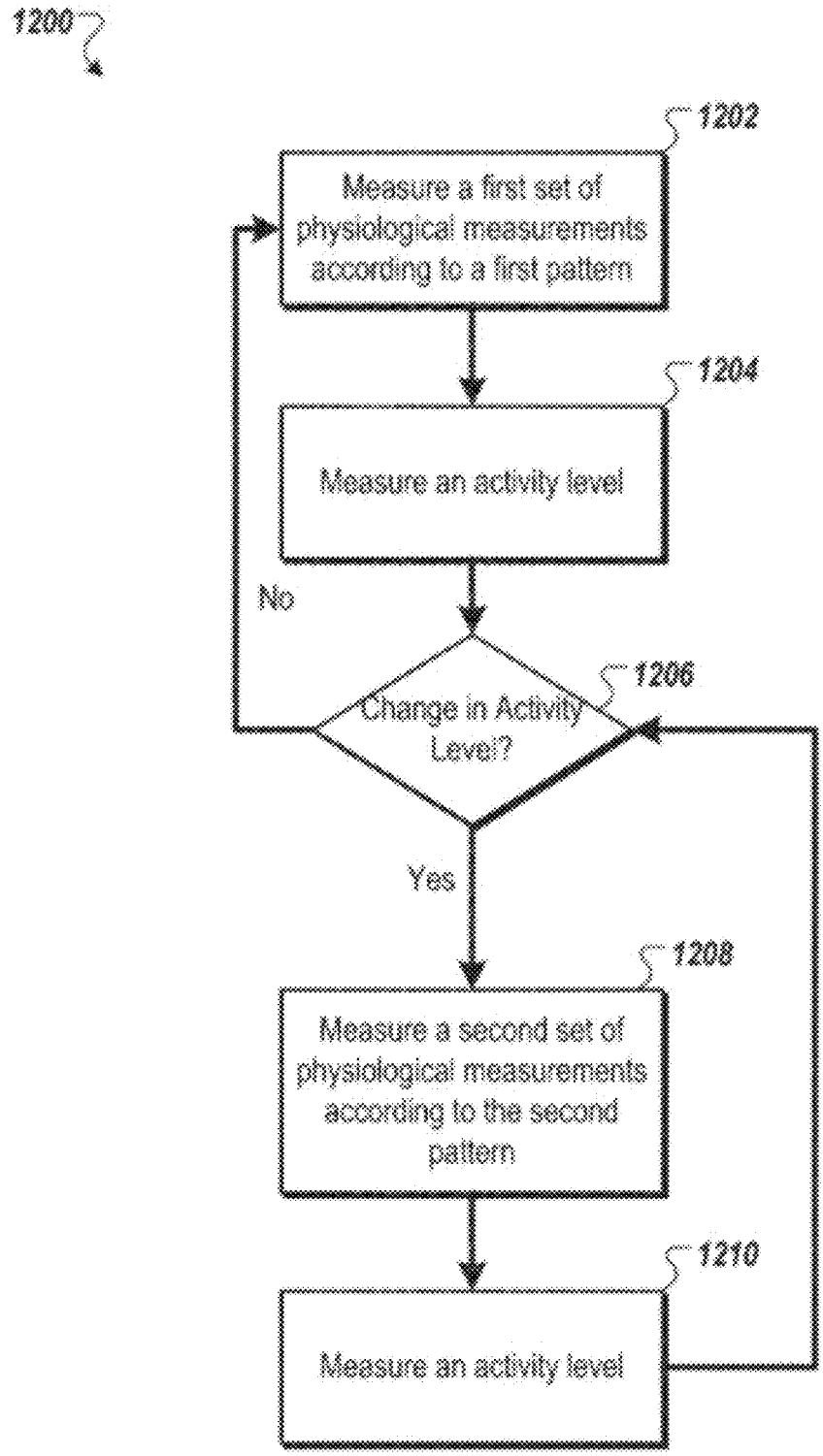
FIG. 12 is a flow diagram of a method of power management of a wearable UMD according to one embodiment.

FIG. 12 is a flow diagram of a method 1200 of power management of a wearable UMD according to one embodiment. The method 1200 is performed by processing logic that may comprise hardware (circuitry, dedicated logic, etc.), software (such as is run on a general purpose computing system or a dedicated machine), firmware (embedded software), or any combination thereof. In one embodiment, the PMM 1120 of FIG. 11 performs the method 1200. In another embodiment, the PMS 140 of FIG. 1A performs the method 1200. Alternatively, other components of the UMDs, as described herein, can perform some or all of the operations of method 1200.

Referring to FIG. 12, processing logic begins with measuring a first set of physiological measurements of a user using a physiological sensor (one or more sensors) according to a first pattern (block 1202). The processing logic measures an activity level of the user using an activity sensor of the wearable hardware device (block 1204). The processing logic determines when there is a change in activity level (as defined by the power management system) (block 1206). If there is no change, no power adjustment activity is performed, and the processing logic returns to block 1202 to measure additional physiological measurements according to the first pattern. If there is a change, a power adjustment activity may be performed to change the first pattern to a second pattern, and the processing logic measures a second set of physiological measurements of the user using the physiological sensor according to the second pattern (block 1208). The processing logic can measure an activity level using the activity sensor (block 1210) and return to block 1206. In this embodiment, there are two patterns, however, in other embodiments, more than two patterns are possible. For example, the activity levels can be separated by multiple thresholds and depending on the measured activity level, corresponding patterns may be selected. In one embodiment, the different patterns are different sampling rates used to take physiological measurements. Alternatively, the different patterns can have any combination of the following: different numbers of sensors being used to take physiological measurements; different number of different physiological measurements to take; different frequency or different granularity of taking physiological measurements; different combination of other components being turned on or off during a period; different combinations of permitted communication types, frequencies, power levels, data rates, communication channels to transmit or receive data using one or more RF circuits components of the system.

In another embodiment, the processing logic measures a first set of physiological measurements of a user using a physiological sensor according to a first pattern. The processing logic measures an activity level of the user using an activity sensor of the wearable hardware device. Processing logic adjusts the first pattern to a second pattern to take a second plurality of physiological measurement of the user in view of the activity level. The processing logic measures a second set of physiological measurements using the physiological sensor according to the second pattern. In a further embodiment, the processing logic determines that the activity level is below a threshold level. The processing logic adjusts to the second pattern accordingly where the second pattern includes a lower sampling rate than a sampling rate at which the first set of physiological measurements are taken with the first pattern. In another embodiment, when the processing logic determines that the activity level is above a threshold level, the processing logic adjusts to the second pattern accordingly where the second pattern includes a higher sampling rate than a sampling rate at which the first set of physiological measurements are taken with the first pattern.

In other embodiments, the processing logic can use one or more predictive algorithms to determine a probability of change in the activity level over time.

Figure 13:
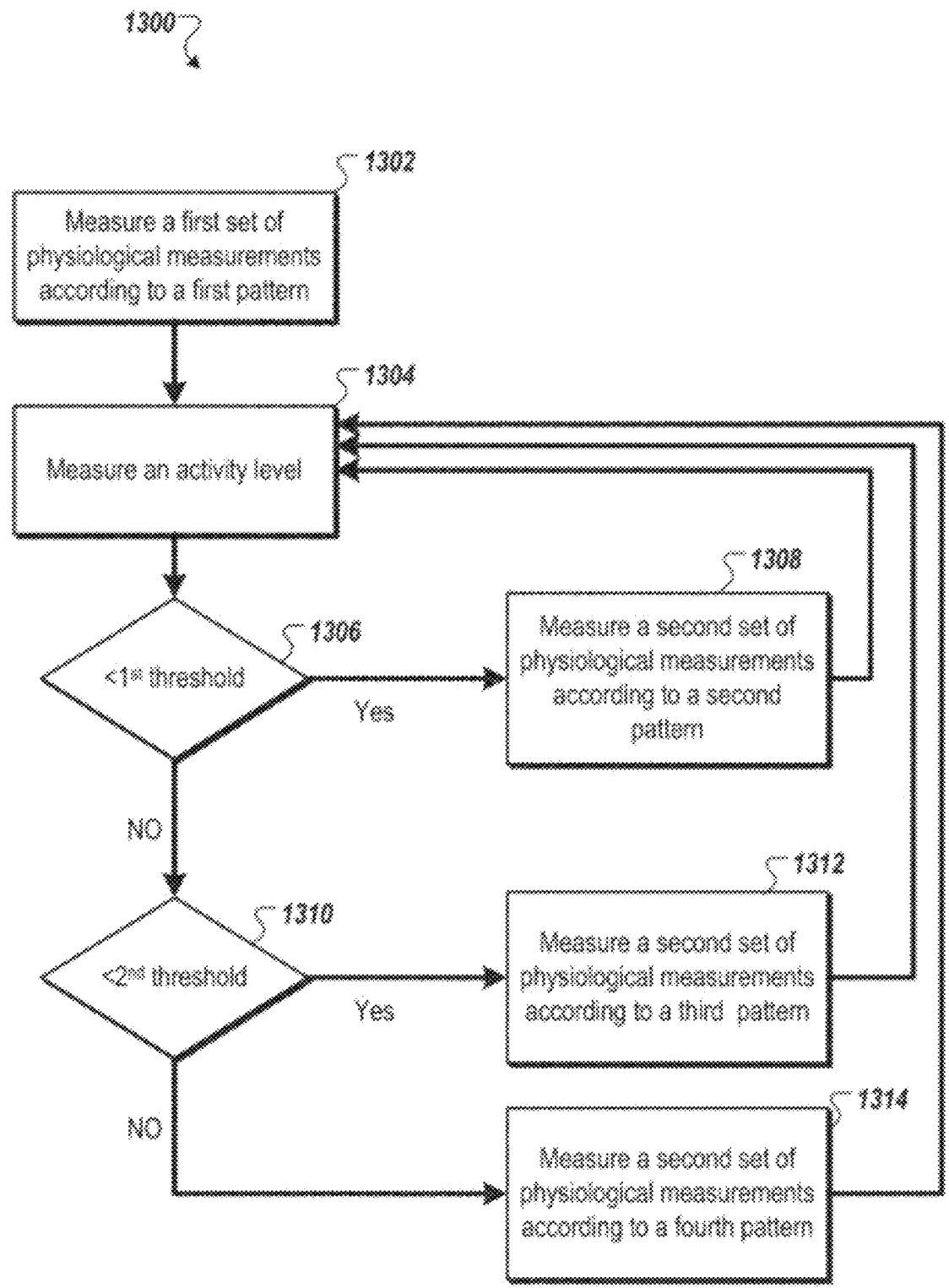
FIG. 13 is a flow diagram of a method of power management of a wearable UMD according to another embodiment.

FIG. 13 is a flow diagram of a method 1300 of power management of a wearable UMD according to another embodiment. The method 1300 is performed by processing logic that may comprise hardware (circuitry, dedicated logic, etc.), software (such as is run on a general purpose computing system or a dedicated machine), firmware (embedded software), or any combination thereof. In one embodiment, the PMM 1120 of FIG. 11 performs the method 1300. In another embodiment, the PMS 140 of FIG. 1A performs the method 1300. Alternatively, other components of the UMDs, as described herein, can perform some or all of the operations of method 1300.

Referring to FIG. 13, processing logic begins with measuring a first set of physiological measurements of a user using a physiological sensor (one or more sensors) according to a first pattern (block 1302). The processing logic measures an activity level of the user using an activity sensor of the wearable hardware device (block 1304). The processing logic determines whether the activity level is less than a first threshold (block 1306). If so, the processing logic measures a second set of physiological measurements of the user using the physiological sensor according to a second pattern (block 1308). For example, the second pattern may be a lower sampling rate than a first sampling rate of the first pattern. If at block 1306 the activity level is not less than the first threshold, the processing logic determines if the activity level is less than a second threshold level (block 1310). If so, the processing logic measures a second set of physiological measurements of the user using the physiological sensor according to a third pattern (block 1312). For example, the third pattern may be a higher sampling rate than the first sampling rate of the first pattern. If at block 1310 the activity level is not less than the second threshold, the processing logic measures a second set of physiological measurements of the user using the physiological sensor according to a fourth pattern (block 1314). For example, the fourth pattern may be a higher sampling rate than the first sampling rate of the first pattern and the second sampling rate of the second pattern. The processing logic at blocks 1308, 1312, and 1314 may return to block 1304 to measure an activity level or determine whether the activity level is changed and proceed accordingly. In other embodiments, more than two threshold levels may be used. Also, in other instances, the threshold levels can be different conventions and the comparison can be whether the activity level meets and/or exceeds the threshold level.

In this embodiment, there are four patterns, however, in other embodiments, different combinations of patterns can be used. In one embodiment, the different patterns are different sampling rates used to take physiological measurements. Alternatively, the different patterns can have any combination of the following: different numbers of sensors being used to take physiological measurements; different number of different physiological measurements to take; different frequency or different granularity of taking physiological measurements; different combination of other components being turned on or off during a period; different combinations of permitted communication types, frequencies, power levels, data rates, communication channels to transmit or receive data using one or more RF circuits components of the system.

In other embodiments, a hardware state machine may be used to determine which state the wearable UMD is in and perform the appropriate power adjustment activities corresponding to the state. The hardware state machine can also build in timers to prevent quick switching in some circumstances.

Figure 14:
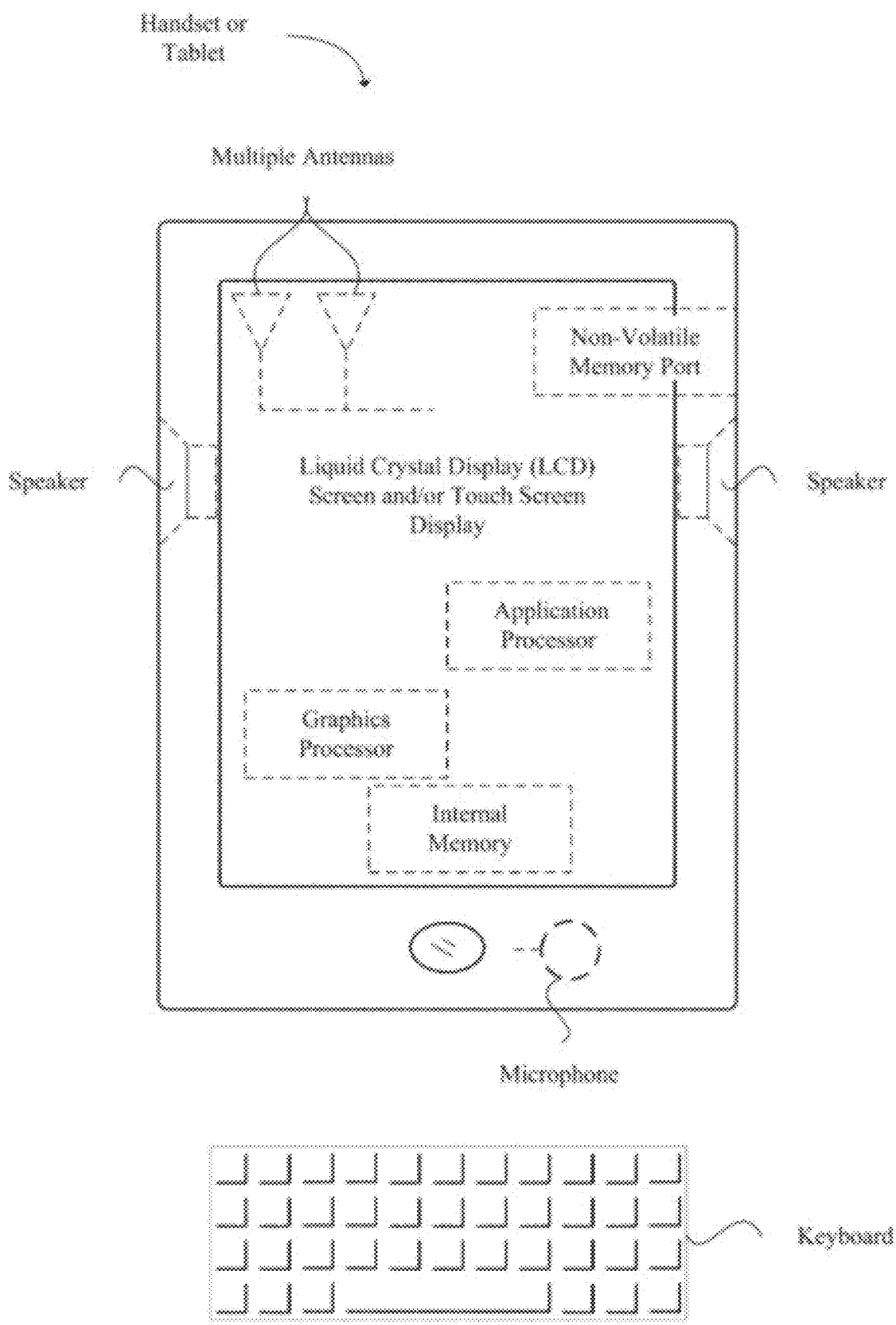
FIG. 14 illustrates a diagrammatic representation of a machine in the example form of a computer system within which a set of instructions, for causing the machine to perform any one or more of the methodologies discussed herein, may be executed.

FIG. 14 provides an example illustration of the device, such as a user equipment (UE), a base station, a UMD, a mobile wireless device, a mobile communication device, a tablet, a handset, or another type of wireless device according to one embodiment. The device can include one or more antennas configured to communicate with different devices. The device can be configured to communicate using at least one wireless communication standard including 3GPP LTE, WiMAX, High-Speed Packet Access (HSPA), Bluetooth®, and Wi-Fi® technologies. The device can communicate using separate antennas for each wireless communication standard or shared antennas for multiple wireless communication standards. The device can communicate in a wireless local area network (WLAN), a wireless personal area network (WPAN), and/or a WWAN.

FIG. 14 also provides an illustration of a microphone and one or more speakers that can be used for audio input and output from the device. The display screen may be a liquid crystal display (LCD) screen, or another type of display screen such as an organic light emitting diode (OLED) display. The display screen can be configured as a touchscreen. The touch screen may use capacitive, resistive, or another type of touch screen technology. An application processor and a graphics processor can be coupled to the internal memory to provide processing and display capabilities. A non-volatile memory port can also be used to provide data input/output options to a user. The non-volatile memory port may also be used to expand the memory capabilities of the wireless device. A keyboard may be integrated with the wireless device or wirelessly connected to the wireless device to provide additional user input. A virtual keyboard may also be provided using the touchscreen.

Various techniques, or certain aspects or portions thereof, may take the form of program code (i.e., instructions) embodied in tangible media, such as floppy diskettes, CD-ROMs, hard drives, non-transitory computer readable storage medium, or any other machine-readable storage medium wherein, when the program code is loaded into and executed by a machine, such as a computer, the machine becomes an apparatus for practicing the various techniques. In the case of program code execution on programmable computers, the computing device may include a processor, a storage medium readable by the processor (including volatile and non-volatile memory and/or storage elements), at least one input device, and at least one output device. The volatile and non-volatile memory and/or storage elements may be a RAM, EPROM, flash drive, optical drive, magnetic hard drive, or another medium for storing electronic data. The base station and mobile station may also include a transceiver module, a counter module, a processing module, and/or a clock module or timer module. One or more programs that may implement or utilize the various techniques described herein may use an application programming interface (API), reusable controls, and the like. Such programs may be implemented in a high level procedural or object-oriented programming language to communicate with a computer system. However, the program(s) may be implemented in assembly or machine language, if desired. In any case, the language may be a compiled or interpreted language and combined with hardware implementations.

It should be understood that many of the functional units described in this specification have been labeled as modules, in order to more particularly emphasize their implementation independence. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in software for execution by various types of processors. An identified module of executable code may, for instance, comprise one or more physical or logical blocks of computer instructions, which may, for instance, be organized as an object, procedure, or function. Nevertheless, the executables of an identified module need not be physically located together but may comprise disparate instructions stored in different locations which, when joined logically together, comprise the module and achieve the stated purpose for the module.

Indeed, a module of executable code may be a single instruction, or many instructions, and may even be distributed over several different code segments, among different programs, and across several memory devices. Similarly, operational data may be identified and illustrated herein within modules and may be embodied in any suitable form and organized within any suitable type of data structure. The operational data may be collected as a single data set, or may be distributed over different locations including over different storage devices, and may exist, at least partially, merely as electronic signals on a system or network. The modules may be passive or active, including agents operable to perform desired functions.

Reference throughout this specification to "an example" means that a particular feature, structure, or characteristic described in connection with the example is included in at least one embodiment of the present invention. Thus, appearances of the phrases "in an example" in various places throughout this specification are not necessarily all referring to the same embodiment.

As used herein, multiple items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. In addition, various embodiments and example of the present invention may be referred to herein along with alternatives for the various components thereof. It is understood that such embodiments, examples, and alternatives are not to be construed as de facto equivalents of one another, but are to be considered as separate and autonomous representations of the present invention.

Furthermore, the described features, structures, or characteristics may be combined in any suitable manner in one or more embodiments. In the foregoing description, numerous specific details are provided, such as examples of layouts, distances, network examples, etc., to provide a thorough understanding of embodiments of the invention. One skilled in the relevant art will recognize, however, that the invention can be practiced without one or more of the specific details, or with other methods, components, layouts, etc. In other instances, well-known structures, materials, or operations are not shown or described in detail to avoid obscuring aspects of the invention.

While the foregoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

Figure 15:
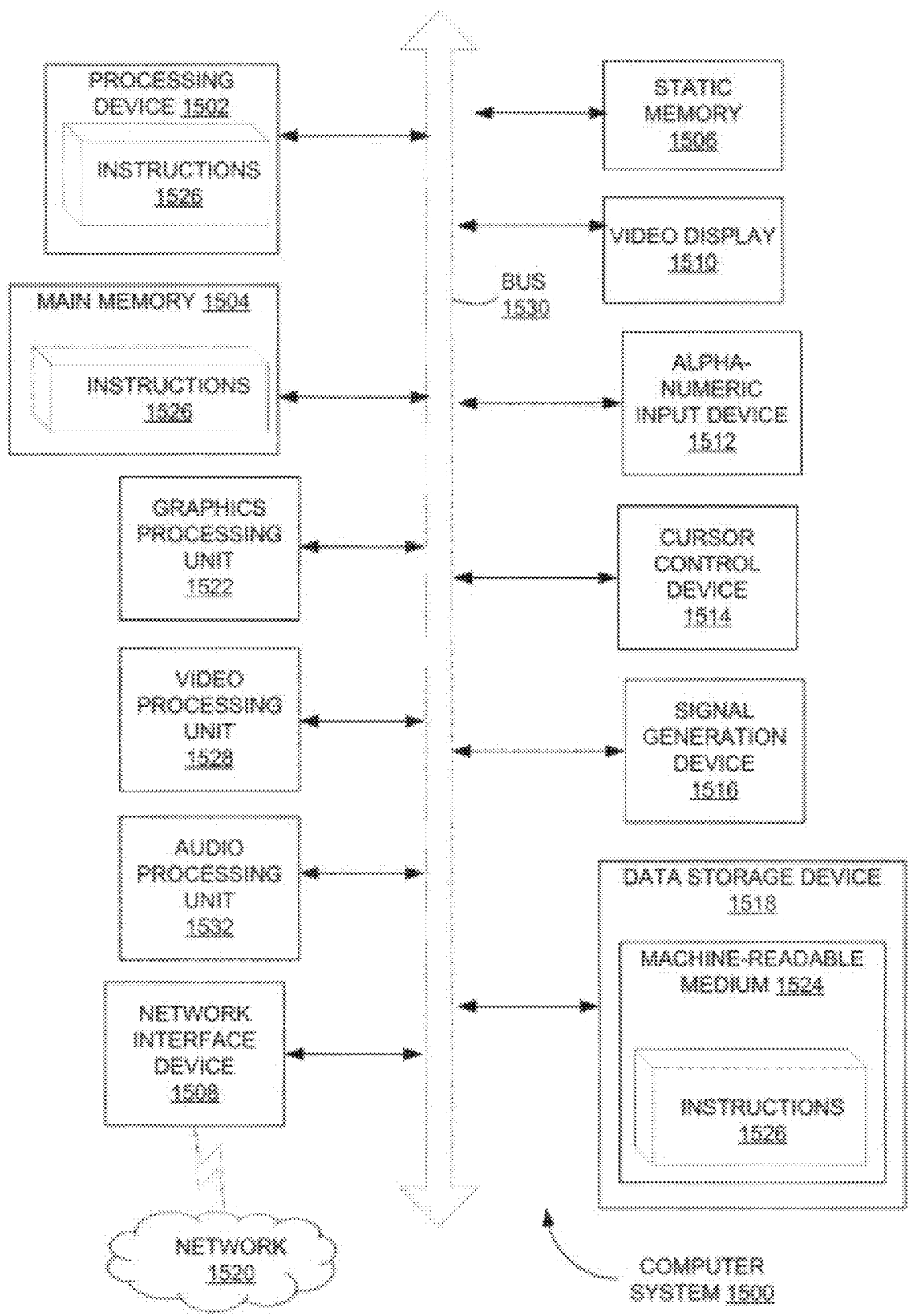
FIG. 15 illustrates a block diagram of one implementation of a computer system.

FIG. 15 illustrates a diagrammatic representation of a machine in the exemplary form of a computer system 1500 within which a set of instructions for causing the machine to perform any one or more of the methodologies discussed herein, may be executed. In alternative implementations, the machine may be connected (e.g., networked) to other machines in a LAN, an intranet, an extranet, or the Internet. The machine may operate in the capacity of a server or a client machine in a client-server network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The exemplary computer system 1500 includes a processing device (processor) 1502, a main memory 1504 (e.g., read-only memory (ROM), flash memory, dynamic random access memory (DRAM) such as synchronous DRAM (SDRAM) or Rambus DRAM (RDRAM), etc.), a static memory 1506 (e.g., flash memory, static random access memory (SRAM), etc.), and a data storage device 1518, which communicate with each other via a bus 1530.

Processing device 1502 represents one or more general-purpose processing devices such as a microprocessor, central processing unit, or the like. More particularly, the processing device 1502 may be a complex instruction set computing (CISC) microprocessor, reduced instruction set computing (RISC) microprocessor, very long instruction word (VLIW) microprocessor, or a processor implementing other instruction sets or processors implementing a combination of instruction sets. The processing device 1502 may also be one or more special-purpose processing devices such as an application specific integrated circuit (ASIC), a field programmable gate array (FPGA), a digital signal processor (DSP), network processor, or the like. The processing device 1502 is configured to execute instructions 1526 for performing the operations and steps discussed herein.

The computer system 1500 may further include a network interface device 1522. The computer system 1500 also may include a video display unit 1510 (e.g., a liquid crystal display (LCD), a cathode ray tube (CRT), or a touch screen), an alphanumeric input device 1512 (e.g., a keyboard), a cursor control device 1514 (e.g., a mouse), and a signal generation device 1516 (e.g., a speaker). The computer system 1500 may further include a video processing unit 1528 and an audio processing unit 1532.

The data storage device 1518 may include a machine-readable storage medium 1524 on which is stored one or more sets of instructions 1526 (e.g., software) embodying any one or more of the methodologies or functions described herein. The instructions 1526 may also reside, completely or at least partially, within the main memory 1504 and/or within the processing device 1502 during execution thereof by the computer system 1500, the main memory 1504 and the processing device 1502 also constituting computer-readable storage media. The instructions 1526 may further be transmitted or received over a network 1520 via the network interface device 1522.

While the machine-readable storage medium 1524 is shown in an exemplary implementation to be a single medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium that is capable of storing, encoding or carrying a set of instructions for execution by the machine and that cause the machine to perform any one or more of the methodologies of the present disclosure. The term "computer-readable storage medium" shall accordingly be taken to include, but not be limited to, solid-state memories, optical media, and magnetic media.

In the foregoing description, numerous details are set forth. It will be apparent, however, to one of ordinary skill in the art having the benefit of this disclosure, that the present disclosure may be practiced without these specific details. In some instances, well-known structures and devices are shown in block diagram form, rather than in detail, in order to avoid obscuring the present disclosure.

Some portions of the detailed description have been presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms such as "segmenting", "analyzing", "determining", "enabling", "identifying," "modifying" or the like, refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices.

The disclosure also relates to an apparatus for performing the operations herein. This apparatus may be specially constructed for the required purposes, or it may include a general purpose computer selectively activated or reconfigured by a computer program stored in the computer. Such a computer program may be stored in a computer-readable storage medium, such as, but not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions.

The words "example" or "exemplary" are used herein to mean serving as an example, instance, or illustration. Any aspect or design described herein as "example' or "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from context to be directed to a singular form. Moreover, use of the term "an embodiment" or "one embodiment" or "an implementation" or "one implementation" throughout is not intended to mean the same embodiment or implementation unless described as such.

Reference throughout this specification to "one embodiment" or "an embodiment" means that a particular feature, structure, or characteristic described in connection with the embodiment is included in at least one embodiment. Thus, the appearances of the phrase "in one embodiment" or "in an embodiment" in various places throughout this specification are not necessarily all referring to the same embodiment. In addition, the term "or" is intended to mean an inclusive "or" rather than an exclusive "or."

It is to be understood that the above description is intended to be illustrative, and not restrictive. Many other implementations will be apparent to those of skill in the art upon reading and understanding the above description. The scope of the disclosure should, therefore, be determined with reference to the appended claims, along with the full scope of equivalents to which such claims are entitled.

The invention claimed is:

1. A system comprising:
   a wearable device comprising:
      an activity sensor configured to measure an activity level of a user;
      a physiological sensor configured to measures a physiological parameter of the user;
      a processing device communicatively coupled to the activity sensor, and the physiological sensor; and
      a memory device configured to store data comprising:
         physiological data;
         activity data;
         instructions for an activity sensor module;
         instructions for a physiological sensor module; and
         instruction for a power management module;
      wherein the processing device is further communicatively coupled to the memory device and configured to:
         predict a future activity based on a correlation of data received from the activity sensor or the physiological sensor and data stored in the memory device; and
         recommend a course of action based on the predicted activity.

2. The system of claim 1, wherein:
   the processing device is configured to:
      compare the activity of the user to the activity data stored in the memory device;
      determine a change in activity;
      predict an event in view of the change in activity; and
      recommend:
         a change in activity for the user,
         an increase in activity sensor measurement granularity, or
         a treatment regimen.

3. The system of claim 2, wherein the processing device is configured to analyze user profile data comprising:
   scheduling information of the user;
   dietary information of the user;
   ethnic or race information of the user;
   weight information of the user;
   gender information of the user;
   physical performance of the user;
   injury information of the user;
   hydration information of the user;
   heart rate information of the user; or
   oxygen saturation level information of the user.

4. The system of claim 3, wherein activity sensor comprises:
   a global positioning system sensor;
   a triangulation sensor;
   a location sensor;
   a vibration sensor;
   a gyroscope sensor;
   an accelerometer sensor;
   a three-dimensional accelerometer sensor;
   a force sensor;
   a pedometer;
   a strain gauge;
   a magnetometer; or
   a geomagnetic field sensor.

5. The system of claim 1, wherein the processing device is configured to:
   compare data provided by the physiological sensor and physiological data stored in the memory device;
   predict a health event in view of a comparison of the data provided by the physiological sensor and the physiological data stored in the memory device; and
   recommend:
      a change in activity for the user;
      an increase in physiological sensor measurement granularity; or
      a treatment regimen.

6. The system of claim 1, wherein the physiological sensor comprises:
   a pulse oximeter sensor;
   an electrocardiography sensor;
   a fluid level sensor;
   an oxygen saturation sensor;
   a body temperature sensor;
   an ambient temperature sensor;
   a plethysmograph sensor;
   a respiration sensor;
   a breath sensor;
   a cardiac sensor;
   a bioimpedance sensor;
   an optical sensor;
   a spectrographic sensor; or
   a humidity sensor.

7. The system of claim 1, wherein the processing device is configured to compare the user profile data with the physiological sensor data to predict an event.

8. The system of claim 1, further comprising:
   an environmental sensor configured to measure:
      humidity,
      ambient temperature,
      altitude,
      barometric pressure, or
      location;
   wherein the memory device is configured to store environmental data based on one or more measurements from the environmental sensor; and
   wherein the processing device is configured to:
      predict an event based on a correlation of data received from:
         the activity sensor,
         the physiological sensor,
         the environmental sensors, and
         data stored in the memory device; and
      recommend a course of action based on the predicted event.

9. A system comprising:
   a wearable device comprising:

an activity sensor configured to take an activity measurement;
a physiological sensor configured to take a physiological measurement; and
a processing device communicatively coupled to the activity sensor and the physiological sensor, wherein the processing device is configured to:
control the activity sensor and the physiological sensor;
identify a first user via a first individual indicator;
identify a second user via a second individual indicator;
identify a third user via a third individual indicator;
identify a group comprising the first user, the second user and the third user via a group indicator; and
analyze data from the first user, the second user, the third user, and the group; and
a graphical user interface configured to represent the data in view of the first individual indicator, the second individual indicator, the third individual indicator, and the group indicator.

10. The system of claim 9, wherein:
the graphical user interface is configured to overlay the data in view of the individual indicators or the group indicators,
information for the group indicators is a first layer of information, and information for the individual indicators is a second layer of information, and
the second layer of information is displayed in a box or field overlaid on top the first layer of group information, and the second layer of information is partially transparent or semi-transparent.

11. The system of claim 10, wherein:
the graphical user interface is configured to display the first layer of information or the second layer of information in response to an input device; and
the input device comprises:
a touch screen;
a mouse;
a stylus; or
a keyboard.

12. The system of claim 9, further comprising:
a memory device configured to store data comprising:
physiological data; and
activity data;
wherein the processing device is communicatively coupled to the memory device and configured to:
predict an event based on a correlation of data received from:
the activity sensors of the individual users;
the physiological sensor of the individual users;
data stored in the memory device for the individual users and the group; and
recommend a course of action based on the predicted event.

13. A system comprising:
a wearable device comprising:
an activity sensor configured to measure an activity level of a user;
a physiological sensor configured to measures a physiological parameter of the user;
a processing device communicatively coupled to the activity sensor, and the physiological sensor; and
a memory device configured to store data comprising:
physiological data;
activity data;
instructions for an activity sensor module;
instructions for a physiological sensor module; and
instruction for a power management module;
wherein the processing device is further communicatively coupled to the memory device and the processing device is configured to:
predict a future activity based on a correlation of data received from the activity sensor or the physiological sensor and data stored in the memory device;
recommend a course of action based on the predicted activity;
control the activity sensor and the physiological sensor;
identify a first user via a first individual indicator;
identify a second user via a second individual indicator;
identify a third user via a third individual indicator;
identify a group comprising the first user, the second user and the third user via a group indicator;
analyze data from the first user, the second user, the third user, and the group; and
represent the data in an individual format and in a group format;
wherein the power management module is configured to:
adjust a sampling rate of the activity sensor or the physiological senor;
adjust measurements of the activity sensor or the physiological sensor;
adjust a frequency of the activity sensor or the physiological sensor;
adjust a granularity of the activity sensor or the physiological sensor;
turn off the activity sensor or the physiological sensor;
adjust a communication channel configured to transmit or receive data from the activity sensor or the physiological sensor;
adjust a frequency to transmit or receive data from the activity sensor or the physiological sensor;
adjust a power consumption level to transmit or receive data from the activity sensor or the physiological sensor; or
adjust a data rate to transmit or receive data from the activity sensor or the physiological sensor; and
a graphical user interface configured to represent the data in view of the group indicators and individual indicators.

14. The system of claim 13, wherein the power management module is configured to:
measure a first set of measurements using a first sensor at a first sampling rate;
adjust the first sampling rate to a second sampling rate in view of an amount of activity; and
measure a second set of measurements using the first sensor at the second sampling rate.

15. The system of claim 14, wherein the power management module is configured to:
calculate a rate of change of two measurements in a period of time to determine an amount of activity of the wearable device; and
adjust the wearable device in view of the rate of change of the two measurements.

16. The system of claim 13, wherein the power management module is configured to:
turn off a circuit configured to send data to an antenna or display;
turn off and turn on a circuit configured to send data to an antenna or display; or
adjust a time a circuit configured to send data to an antenna or display is turned on.

17. The system of claim 13, wherein the power management module is configured to
measure a health level of a power source of the wearable device via:
measuring the health level of the power source;
comparing the health level of the power source to health level data stored in the memory device;
measuring a time required to charge the power source;
comparing the time required to change the power source to power source charging data stored in the memory device; and
adjusting a power consumption level in view of the health level or charging time.

18. The system of claim 13, wherein the wearable device further comprises a hardware motion sensor configured to measure movement or motion of the wearable device, wherein the power management module is configured to determine an amount of activity in view of the amount of activity of the wearable device.

19. The system of claim 18, wherein the hardware motion sensor comprises:
an accelerometer sensor;
a gyroscope sensor;
a magnetometer;
a GPS sensor;
a location sensor;
a vibration sensor;
a 3D accelerometer sensor;
a force sensor;
a pedometer;
a strain gauge;
a magnetometer; or
a geomagnetic field sensor.

20. The system of claim 13, wherein the power management system is configured to:
determine an activity rate from the activity sensor;
compare the activity rate to threshold activity rate data stored in the memory device;
determine the activity rate is below the threshold activity rate and reduce the power consumption levels of the wearable device; or
determine that the activity rate is above the threshold activity rate and maintain power consumption levels of the wearable device.

* * * * *